United States Patent [19]
Bryan et al.

[11] Patent Number: 6,054,313
[45] Date of Patent: Apr. 25, 2000

[54] NUCLEIC ACID AND AMINO ACID SEQUENCES FOR MAMMALIAN SULFONYLUREA RECEPTOR

[75] Inventors: Joseph Bryan; Lydia Aguilar Bryan, both of Houston, Tex.; Daniel Nelson, Charlotte, N.C.

[73] Assignee: Baylor College of Medicine, Houston, Tex.

[21] Appl. No.: 08/488,546

[22] Filed: Jun. 7, 1995

Related U.S. Application Data

[60] Division of application No. 08/404,531, Mar. 15, 1995, Pat. No. 5,863,724, which is a continuation-in-part of application No. 08/226,972, Apr. 13, 1994, abandoned.

[51] Int. Cl.[7] .............................. C12N 5/00; C12N 15/00; C07H 21/04; C07K 1/00
[52] U.S. Cl. ........................ 435/325; 435/361; 435/375; 435/69.1; 435/455; 435/320.1; 536/23.5; 530/350
[58] Field of Search ....................... 536/23.5; 435/320.1, 435/69.1, 172.1, 172.3, 325, 361, 375, 252.3, 455; 530/350

[56] References Cited

U.S. PATENT DOCUMENTS

| | | | |
|---|---|---|---|
| 4,237,224 | 12/1980 | Cohen et al. | 435/68 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,883,750 | 11/1989 | Whiteley et al. | 435/6 |
| 4,965,188 | 10/1990 | Mullis et al. | 435/6 |

FOREIGN PATENT DOCUMENTS

| | | |
|---|---|---|
| 0 329 822 A2 | 8/1988 | European Pat. Off. . |
| 2 202 328 | 3/1988 | United Kingdom . |
| WO 87/06270 | 4/1987 | WIPO . |
| WO 88/10315 | 6/1988 | WIPO . |
| WO 89/06700 | 1/1989 | WIPO . |
| WO 89/09284 | 3/1989 | WIPO . |

OTHER PUBLICATIONS

C. Groman et al. PNAS 79:6777–81, '82.

L. Aguilar–Bryan et al. Science 268:423–426, '95.

P. Thomas et al. Science 268:426–429, '95.

Nelson et al. The High Affinity HIT Cell Sufonylurea Receptor Intern'l Conference on ATP–Senstivie K⁻Channels and Sulfonylurea Receptors, Houston TX, Sep. 30–Oct. 1, 1993.

Vu et al. Pancreatic β–Cell Ion Channels: Role in Diabetes Pathogenesis and Therapy, Amer. Diab. Assoc. 24th Internat'l Res. Symp., Oct. 27, 1989, Marco Island, Florida.

Aguilar–Bryan Synthesis and Characterization of an Iodinated Sulfonylurea *J. Cell Biol* 1988 107:561.

Aguilar–Bryan Photoaffinity Labeling of the β cell sulfonylurea Receptor Using a Novel Glyburide Analog Clinical Research National Meeting Apr. 1989 vol. 37.

Aguilar–Bryan Co–Expression of Sulfonylurea Receptors and $K_{ATP}$ Channels: Evidence that a 140 kDA Protein is an Integral Part of this Channel Biophysical Soc. Houston Texas 1992.

Aguilar–Bryan Photoaffinity Labeling and Partial Puriciation of the β Call Sufonylurea Receptor Using a Novel Biologically Active Glyburide Analogs *J. Biol. Chem.* 1990 265:8218.

Aguilar–Bryan Cloning of a High Affinity Sulfonylurea Receptor From Rodent α– and β– Cells *J. Cell. Biochem. Suppl.* 1994 18:133.

Aguilar–Bryan et al. Co–Expression of Sulfonylurea Receptors and $K_{ATP}$ Channels in Hamster Insulinoma Tumor (HIT) Cells *JBC* 1992 267:14934.

Ashcroft et al. Properties and Functions of ATP–Sensitive K–Channels *Cell Signal.* 1990 2:197–214.

Ashcroft et al. The Sulfonylurea Receptor *Biochim. Biophys. Acta* 1992 1175:45–49.

Ashford et al. Tolbutamide excites rat glucoreceptive ventromedial hypothallamic neurones by indirect inhibition of ATP–K⁺channels *Br. J. Pharmac.* 1990 101:531–540.

Bernardi et al. ATP/ADP Binding Sites are Present in the Sulfonylurea Binding Protein Associated with Brain ATP–Sensitive K⁺Channels *Biochemistry* 1992 31:6328–6332.

Boyle et al. Electrophysiological Expression of Ion Channels in Xenopus Oocytes *Methods in Neuroscience* 1991 4:157–173.

Bryan et al. Cloning of a Sulfonylurea Receptor (ATP–Sensitive K⁻ Channel?) From Rodent α– and β–Cells Intern'l Conference on ATP–Sensitive K⁻ Channels and Sulfonylurea Receptors, Houston, Tx 1993.

Cole et al. Overexpression of a Transporter Gene in a Multidrug–Resistant Human Lung Cancer Cell Line *Science* 1992 258:1650–1654.

de Weille et al. Activation and Inhibition of APT–Sensitive K⁺Channels By Fluorescein Derivatives *J. Biol. Chem* 1992 267:4557–4563.

Edwards et al. The Pharmacology of ATP–Sensitive Potassium Channels *Annu. Rev. Pharmacol. Toxicol.* 1993 33:597–637.

Eisenberg et al. Analysis of Membrane and Surface Protein Sequence with the Hydrophobic Moment Plot *J. Mol. Biol.* 1984 179:125.

Feng et al. Progressive Sequence Alignment as a Prerequisite to Correct Phylogenetic Trees *J. Mol. Evol.* 1987 25:351.

Gerich J.E. Oral Hypoglycemic Agents *New Engl. J. Med.* 1989 321:1231–1245.

(List continued on next page.)

*Primary Examiner*—Deborah Crouch
*Assistant Examiner*—Jill D. Martin
*Attorney, Agent, or Firm*—Woodcock Washburn Kurtz MacKiewicz & Norris, LLP

[57] ABSTRACT

Sulfonylurea receptor nucleic acid and amino acid sequences are disclosed. The invention is also directed to expression vectors comprising the nucleic acid sequences and to isolated host cells that express the nucleic acid sequences.

9 Claims, 13 Drawing Sheets

OTHER PUBLICATIONS

Gregory et al. Expression and characterization of the cystic fibrosis transmembrane conductance regulator *Nature* 1990 347:382–386.

Ho et al. Cloning and Expression of an inwardly rectifying ATP–regulated Potassium Channel *Nature* 1993 362:31–38.

Hopkins et al. Two Sites for Adenine–Nucleotide Regulation of ATP–Sensitive Potassium Channels in Mouse Pancreatic β–Cells and HIT Cells *J. Membrane Biol.* 1992 129:287–295.

Hyde et al. Structural Model of ATP–Binding Proteins Associated with Cystic Fibrosis, multidrug resistance and bacterial transport *Nature* 1990 346:362–365.

Kelly et al. Cloning and Expression of A Novel Inward Rectifier K+ Channel HRK1 From Human Hippocampus *Biophysical J.* 1994 66(2) :A109.

Khan et al. Dissociation of $K_{ATP}$ channel and sulphonylurea receptor in the rat clonal insulin–secreting cell line, CR1–D11 *Proc. R. Soc. Lond. B* 1993 253:225–231.

Kozak M. Point Mutations Define a Sequence Flanking the AUG Initator Codon That Modulates Traslation by Eukaryotic Ribosomes *Cell* 1986 44:283.

Kramer et al. Direct Photoaffinity labeling of the putative sulfonylurea receptor in rat β–Cell tumor membranes by [H3] glibenclamide *FEBS Lett.* 1988 229:355–359.

Kyte et al. A simple method for displaying the hydropathic Character of a Protein *J. Mol. Biol.* 1982 157:105–132.

Nelson et al. Evidence that a 140 kDa Protein Contains the β–Cell High Affinity Sulfonylurea Binding Site and is an Integral Part of the ATP–Sensive Potassium Channel *Amer. Diab. Assoc. Diabetes* 1992 41:78A.

Nelson et al. The High Affinity HIT Cell Sufonylurea Receptor Intern'l Conference on ATP–Sensitive K⁻ Channels and Sulfonylurea Receptors, Houston Tx.

Nelson et al. Photolabeling of β–Cell Membrane Proteins with an $^{125}$I–Labeled Glyburide Analog: The High Affinity Sulfonylurea Binding Site Residesona 140kDa Polypeptide Houston Tx.

Nelson et al. Purification and Characterization of the High Affinity Sulfonylurea Receptors *Biophys. J.* 1993 64:311.

Nelson et al. Purification of the 140 kDa High Affinity Sulfonylurea Recptor *Diabetes* 1993 42:129.

Nelson et al. Specificity of Photolabeling of β–Cell Membrane Proteins with an $^{125}$I–Labeled Glyburide Analog *JBC* 1992 267:14928.

Nichols et al. Adenosine triphosphate–sensitive potassium channels in the cardiovascular system *Am. J. Physiol.* 1991 261:H1675–H1686.

Panten et al. Pancreatic and Extrapancreatic Sulfonylurea Receptors *Horm. Metab. Res.* 1992 24:549–554.

Panten et al. Control of Insulin Secetion by Sulfonylureas, Meglitinide and Diazoxide in Relation to Their Binding to the Sulfonylurea Receptor in Pancreatic Islets *Biochem. Pharm.* 1989 38:1217–1229.

Posnett et al. A Novel Method for Producing Anti–peptide Antibodies *J. Biol. Chem.* 263:1719–1725.

Rajan et al. Sulfonylurea Receptors and ATP–Sensitive K⁺Channels in a Glucagon Secreting Pancreatic Alpha Cell Line *Diabetes* 1992 41:47A.

Rajan et al. ATP–Sensitive K+ Channels in Pancreatic Alpha Cells *Biophys J.* 64:A311.

Rajan et al. Ion Channels and Insulin Secretion *Diabetes Care* 1990 13:340–363.

Rajan et al. Sulfonylurea Receptors and ATP–sensivitive K⁺Channels in Clonal Pancreatic α Cells *J. Biol. Chem.* 1993 268:15221–15228.

Riordan et al. Identification of the Cystic Fibrosis Gene: Cloning and Characterization of Complementary DNA *Science* 1989 245:1066–1073.

Sanger et al. DNA sequencing with chain–terminating inhibitors *Proc. Nat'l. Acad. Sci USA* 1977 74:5463.

Schmid–Antomarchi et al. The Receptor for Antidiabetic Sulfonylureas Controls the Activity of ATP–modulated K⁺Channel in Insulin–secreting Cells *J. Biol. Chem.* 1987 262:15840–15844.

Schwanstecher et al. The Binding Properties of the Solubilized Sulfonylurea Receptor from a Pancreatic B–Cell Line are Modulated by the $Mg^{++}$–Complex of $ATP^1$ *J. Phar. Exper. Ther.* 1992 262:495–502.

Schwanstecher et al. *Br. J. Pharm.* 1992 107:87–94.

Takano et al. The ATP–Sensitive K⁺ Channel *Progress in Neurobiology* 1993 41:21–30.

Vu et al. Functional Solubilization of the HIT Cell SUlfonylurea Receptor *Diabetes* 1989 38:178a.

Vu et al. Pancreatic β–Cell Ion Channels: Role in Diabetes Pathogenesis and Therapy Amer. Diab. Assoc. 24th Internat'l Res. Symp. 1989.

Vu et al. Partial Purification of the HIT Cell SUlfonylurea Receptor *J. Cell BIol.* 1989 109:102.

Walker et al. *EMBO Jour.* 1982 1:945–951.

Aynsley–Green et al. Nesidioblastosis of the pancreas: definitionof the syndrome and the Management of the severe neonatal hyperinsulinaemic hyppoglycaemia *Arch. Dis. Child.* 1981 56:496.

Kaiser et al. Regulation of insulin release in persistent hyperinsulinaemic hypoglycaemia of infancy Studied in long–term culture of pancreatic tissue *Diabetologia* 1990 33:482.

Bruining, Recent advances in hyperinsulinism and the pathogenesis of diabetes mellitus *Curr. Opin. Pediatr.* 1990 2:758.

Mathew et al. Persistent Neonatal Hyperinsuinism *Clin. Pediatr.* 1988 27:148.

Glaser et al. Familial hyperinsulinism maps to chromosome 11p14–15.1, 30 cM centromeric to the insulin gene *Nature Genet.* 1994 7:185.

Thomas et al. Homozygosity Mapping, to Chromosome 11p, of the Gene for Familial Persistent Hyperinsulinemic Hypoglycemia of Infancy *Am. J. Hum. Genet.* 1995 56:416–421.

Kohler et al. Continuous Cultures of fused cells secreting antibody of predefined specificity *Nature* 1975 256:495–497.

Cline M. J. Perspectives for Gene Therapy: Inserting New Genetic Information Into Mammalian Cells by Physical Techniques and Viral Vectors *Pharmac. Ther.* 1985 29:69–92.

Walker G.T. et al. Isothermal in vitro amplification of DNA by a restriction enzyme/DNA polymerase system *Proc. Natl. Acad. Sci. (U.S.A.)* 1992 89:392–396.

Kwoh et al. Transcription–based amplification system and detection of amplified human immunodeficiency virus type 1 with a bead–based sandwich hybridization format *Proc. Natl. Acad. Sci. (U.S.A.)* 1989 86:1173.

Ohara et al. One–sided polymerase chain reaction: The amplification of cDNA *Proc. Natl. Acad. Sci. (U.S.A.)* 1989 86:5673–5677.

Wu et al. The Ligation Amplification Reaction (LAR)–Amplification of Specific DNA Sequences Using Sequential Rounds of Template–Dependent Ligation *Genomics* 1989 4:560.

Maxam et al. A new method for sequencing DNA *Proc. Natl. Acad. Sci. USA* 1977 74:560–564.

Aguilar–Bryan et al. Photoaffinity Labeling and Partial Purification of the β Cell Sulfonylurea Receptor Using a Novel, Biologically Active Glyburide Analog *J. Biol. Chem.* 1990 265:8218–8224.

Thomas et al. Mutations in the Sulfonylurea Receptor Gene in Familia Persistent Hyperinsulinemic Hypoglycemia of Infancey *Science* 1995 268:426–429.

Lichter et al. High–Resolution Mapping of Human Chromosome 11 by in Situ Hybridization with Cosmid Clones *Science* 1990 247:64.

Ijdo et al. Multiple Variants in Subtelomeric Regions of Normal Karyotypes *Genomics* 1992 14:1019.

Weish et al. Molecular Mechanisms of CFTR chloride Channel Dysfunction in Cystic Fibrosis *Cell* 1993 73:1251.

Khorana et al. Direct sequencing of PCR products in agarose gel slices *Nucleic Acids Res.* 1994 22:3425.

Lou et al. The Calcitonin Exon and its Flanking Intronic Sequences Are Sufficient for the Regulation of Human Calcitonin/Calcitonin Gene–Related Peptide Alternative RNA Splicing *Mol. Endo.* 1994 8:1618.

Takahashi et al. A null mutation in the human CNTF gene is not causally related to neurological diseases *Nature Genet.* 1994 7:79.

Satokata et al. Characterizationof a splicing mutation in group A *xeroderma pigmentosum Proc. Natl. Acad. Sci.* 1990 87:9908.

Higashi et al. Aberrant splicing and missense, mutations cause steroid 21–hydroxylase [P–450 (C21)] deficiency in humans: Possible gene conversion products *Proc. Natl. Acad. Sci., USA* 85, 7486 1988.

Philipson et al. Pas de Deux or More: The Sulfonylurea Receptor and K+ Channels *Science* 1995 268:372–373.

Aguilar–Bryan et al. Cloning of the βCell High–Affinity Sulfonylurea Receptor: A Regulator of Insulin Secretion *Science* 1995 268:423–425.

Scangos et al. Gene Transfer into Mice *Advance In Genetics: Molecular Genetics of Development* 1987 24:285–323.

Virsolvy–Vergine et al. Endosulfine, an endogenous kpeptidic ligand for the sulfonylurea receptor: Purification and partial characterization from ovine brain *Proc. Natl. Acad. Sci. USA* 1992 89:6629–66363.

FIG. 1B

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 1308 base pairs (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:1:

```
GGACCTGCAG CAGCTGGATG ACACCACCCA GCTTCCACTT CTCTCACACT TTGCCGAAAC        60
CGTAGAAGGA CTCACCACCA TCCGGGCCTT CAGGTATGAG GCCCGGTTCC AGCAGAAGCT       120
TCTCGAATAC ACAGACTCCA ACAACATTGC TTCCCTCTTC CTCACAGCTG CCAACAGATG       180
GCTGGAAGTC CGAATGGAGT ACATCGGTGC ATGTGTGGTG CTCATCGCAG CGGTGACCTC       240
CATCTCCAAC TCCCTGCACA GGGAGCTCTC TGCTGGCCTG GTGGGCCTGG GCCTTACCTA       300
CGCCCTAATG GTCTCCAACT ACCTCAACTG GATGGTGAGG AACCTGGCAG ACATGGAGCT       360
CCAGCTGGGG GCTGTGAAGC GCATCCATGG GCTCCTGAAA ACCGAGGCAG AGAGCTACGA       420
GGGACTCCTG GCACCATCGC TGATCCCAAA GAACTGGCCA GACCAAGGGA AGATCCAGAT       480
CCAGAACCTG AGCGTGCGCT ACGACAGCTC CCTGAAGCCG GTGCTGAAGC ACGTCAATGC       540
CCTCATCTCC CCTGGACAGA AGATCGGGAT CTGCGGCCGC ACCGGCAGTG GGAAGTCCTC       600
CTTCTCTCTT GCCTTCTTCC GCATGGTGGA CACGTTCGAA GGGCACATCA TCATTGATGG       660
CATTGACATC GCCAAACTGC CGCTGCACAC CCTGCGCTCA CGCCTCTCCA TCATCCTGCA       720
GGACCCCGTC CTCTTCAGCG GCACCATCCG ATTTAACCTG GACCCTGAGA GGAAGTGCTC       780
AGATAGCACA CTGTGGGAGG CCCTGGAAAT CGCCCAGCTG AAGCTGGTGG TGAAGGCACT       840
GCCAGGAGGC CTCGATGCCA TCATCACAGA AGGCGGGGAG AATTTCAGCC AGGGACAGAG       900
GCAGCTGTTC TGCCTGGCCC GGGCCTTCGT GAGGAAGACC AGCATCTTCA TCATGGACGA       960
GGCCACGGCT TCCATTGACA TGGCCACGGA AAACATCCTC CAAAAGGTGG TGATGACAGC      1020
CTTCGCAGAC CGCACTGTGG TCACCATCGC GCATCGAGTG CACACCATCC TGAGTGCAGA      1080
CCTGGTGATC GTCCTGAAGC GGGGTGCCAT CCTTGAGTTC GATAAGCCAG AGAAGCTGCT      1140
CAGCCGGAAG GACAGCGTCT TCGCCTCCTT CGTCCGTGCA GACAAGTGAC CTGCCAGAGC      1200
CCAAGTGCCA TCCCACATTC GGACCCTGCC CATACCCCTG CCTGGGTTTT CTAACTGTAA      1260
ATCACTTGTA AATAAATAGA TTTGATTATT TCCTAAAAAA AAAAAAAA                   1308
```

(2) INFORMATION FOR SEQ ID NO:2:

(i) SEQUENCE CHARACTERISTICS:
        (A) LENGTH: 1308 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 2..1186

(xi) SEQUENCE DESCRIPTION: SEQ ID NO:2:

```
G GAC CTG CAG CAG CTG GAT GAC ACC ACC CAG CTT CCA CTT CTC TCA         46
  Asp Leu Gln Gln Leu Asp Asp Thr Thr Gln Leu Pro Leu Leu Ser
```

```
       1                   5                  10                 15
CAC TTT GCC GAA ACC GTA GAA GGA CTC ACC ACC ATC CGG GCC TTC AGG       94
His Phe Ala Glu Thr Val Glu Gly Leu Thr Thr Ile Arg Ala Phe Arg
                    20                  25                  30

TAT GAG GCC CGG TTC CAG CAG AAG CTT CTC GAA TAC ACA GAC TCC AAC      142
Tyr Glu Ala Arg Phe Gln Gln Lys Leu Leu Glu Tyr Thr Asp Ser Asn
                35                  40                  45

AAC ATT GCT TCC CTC TTC CTC ACA GCT GCC AAC AGA TGG CTG GAA GTC      190
Asn Ile Ala Ser Leu Phe Leu Thr Ala Ala Asn Arg Trp Leu Glu Val
            50                  55                  60

CGA ATG GAG TAC ATC GGT GCA TGT GTG GTG CTC ATC GCA GCG GTG ACC      238
Arg Met Glu Tyr Ile Gly Ala Cys Val Val Leu Ile Ala Ala Val Thr
        65                  70                  75

TCC ATC TCC AAC TCC CTG CAC AGG GAG CTC TCT GCT GGC CTG GTG GGC      286
Ser Ile Ser Asn Ser Leu His Arg Glu Leu Ser Ala Gly Leu Val Gly
80                  85                  90                  95

CTG GGC CTT ACC TAC GCC CTA ATG GTC TCC AAC TAC CTC AAC TGG ATG      334
Leu Gly Leu Thr Tyr Ala Leu Met Val Ser Asn Tyr Leu Asn Trp Met
                100                 105                 110

GTG AGG AAC CTG GCA GAC ATG GAG CTC CAG CTG GGG GCT GTG AAG CGC      382
Val Arg Asn Leu Ala Asp Met Glu Leu Gln Leu Gly Ala Val Lys Arg
            115                 120                 125

ATC CAT GGG CTC CTG AAA ACC GAG GCA GAG AGC TAC GAG GGA CTC CTG      430
Ile His Gly Leu Leu Lys Thr Glu Ala Glu Ser Tyr Glu Gly Leu Leu
        130                 135                 140

GCA CCA TCG CTG ATC CCA AAG AAC TGG CCA GAC CAA GGG AAG ATC CAG      478
Ala Pro Ser Leu Ile Pro Lys Asn Trp Pro Asp Gln Gly Lys Ile Gln
145                 150                 155

ATC CAG AAC CTG AGC GTG CGC TAC GAC AGC TCC CTG AAG CCG GTG CTG      526
Ile Gln Asn Leu Ser Val Arg Tyr Asp Ser Ser Leu Lys Pro Val Leu
160                 165                 170                 175

AAG CAC GTC AAT GCC CTC ATC TCC CCT GGA CAG AAG ATC GGG ATC TGC      574
Lys His Val Asn Ala Leu Ile Ser Pro Gly Gln Lys Ile Gly Ile Cys
                180                 185                 190

GGC CGC ACC GGC AGT GGG AAG TCC TCC TTC TCT CTT GCC TTC TTC CGC      622
Gly Arg Thr Gly Ser Gly Lys Ser Ser Phe Ser Leu Ala Phe Phe Arg
            195                 200                 205

ATG GTG GAC ACG TTC GAA GGG CAC ATC ATC ATT GAT GGC ATT GAC ATC      670
Met Val Asp Thr Phe Glu Gly His Ile Ile Ile Asp Gly Ile Asp Ile
        210                 215                 220

GCC AAA CTG CCG CTG CAC ACC CTG CGC TCA CGC CTC TCC ATC ATC CTG      718
Ala Lys Leu Pro Leu His Thr Leu Arg Ser Arg Leu Ser Ile Ile Leu
225                 230                 235

CAG GAC CCC GTC CTC TTC AGC GGC ACC ATC CGA TTT AAC CTG GAC CCT      766
Gln Asp Pro Val Leu Phe Ser Gly Thr Ile Arg Phe Asn Leu Asp Pro
240                 245                 250                 255

GAG AGG AAG TGC TCA GAT AGC ACA CTG TGG GAG GCC CTG GAA ATC GCC      814
Glu Arg Lys Cys Ser Asp Ser Thr Leu Trp Glu Ala Leu Glu Ile Ala
                260                 265                 270

CAG CTG AAG CTG GTG GTG AAG GCA CTG CCA GGA GGC CTC GAT GCC ATC      862
Gln Leu Lys Leu Val Val Lys Ala Leu Pro Gly Gly Leu Asp Ala Ile
            275                 280                 285

ATC ACA GAA GGC GGG GAG AAT TTC AGC CAG GGA CAG AGG CAG CTG TTC      910
Ile Thr Glu Gly Gly Glu Asn Phe Ser Gln Gly Gln Arg Gln Leu Phe
        290                 295                 300

TGC CTG GCC CGG GCC TTC GTG AGG AAG ACC AGC ATC TTC ATC ATG GAC      958
Cys Leu Ala Arg Ala Phe Val Arg Lys Thr Ser Ile Phe Ile Met Asp
305                 310                 315

GAG GCC ACG GCT TCC ATT GAC ATG GCC ACG GAA AAC ATC CTC CAA AAG     1006
```

```
Glu Ala Thr Ala Ser Ile Asp Met Ala Thr Glu Asn Ile Leu Gln Lys
320                 325                 330                 335

GTG GTG ATG ACA GCC TTC GCA GAC CGC ACT GTG GTC ACC ATC GCG CAT      1054
Val Val Met Thr Ala Phe Ala Asp Arg Thr Val Val Thr Ile Ala His
                340                 345                 350

CGA GTG CAC ACC ATC CTG AGT GCA GAC CTG GTG ATC GTC CTG AAG CGG      1102
Arg Val His Thr Ile Leu Ser Ala Asp Leu Val Ile Val Leu Lys Arg
            355                 360                 365

GGT GCC ATC CTT GAG TTC GAT AAG CCA GAG AAG CTG CTC AGC CGG AAG      1150
Gly Ala Ile Leu Glu Phe Asp Lys Pro Glu Lys Leu Leu Ser Arg Lys
        370                 375                 380

GAC AGC GTC TTC GCC TCC TTC GTC CGT GCA GAC AAG TGACCTGCCA           1196
Asp Ser Val Phe Ala Ser Phe Val Arg Ala Asp Lys
    385                 390                 395

GAGCCCAAGT GCCATCCCAC ATTCGGACCC TGCCCATACC CCTGCCTGGG TTTTCTAACT    1256

GTAAATCACT TGTAAATAAA TAGATTTGAT TATTTCCTAA AAAAAAAAAA AA            1308

(2) INFORMATION FOR SEQ ID NO:3:

(i) SEQUENCE CHARACTERISTICS:
        (A) LENGTH: 395 amino acids
        (B) TYPE: amino acid
        (D) TOPOLOGY: linear (ii) MOLECULE TYPE: protein (xi) SEQUENCE DESCRIPTION: SEQ ID NO:3:

Asp Leu Gln Gln Leu Asp Asp Thr Thr Gln Leu Pro Leu Leu Ser His
1               5                   10                  15

Phe Ala Glu Thr Val Glu Gly Leu Thr Thr Ile Arg Ala Phe Arg Tyr
            20                  25                  30

Glu Ala Arg Phe Gln Gln Lys Leu Leu Glu Tyr Thr Asp Ser Asn Asn
        35                  40                  45

Ile Ala Ser Leu Phe Leu Thr Ala Ala Asn Arg Trp Leu Glu Val Arg
    50                  55                  60

Met Glu Tyr Ile Gly Ala Cys Val Val Leu Ile Ala Ala Val Thr Ser
65                  70                  75                  80

Ile Ser Asn Ser Leu His Arg Glu Leu Ser Ala Gly Leu Val Gly Leu
                85                  90                  95

Gly Leu Thr Tyr Ala Leu Met Val Ser Asn Tyr Leu Asn Trp Met Val
            100                 105                 110

Arg Asn Leu Ala Asp Met Glu Leu Gln Leu Gly Ala Val Lys Arg Ile
        115                 120                 125

His Gly Leu Leu Lys Thr Glu Ala Glu Ser Tyr Glu Gly Leu Leu Ala
    130                 135                 140

Pro Ser Leu Ile Pro Lys Asn Trp Pro Asp Gln Gly Lys Ile Gln Ile
145                 150                 155                 160

Gln Asn Leu Ser Val Arg Tyr Asp Ser Ser Leu Lys Pro Val Leu Lys
                165                 170                 175

His Val Asn Ala Leu Ile Ser Pro Gly Gln Lys Ile Gly Ile Cys Gly
            180                 185                 190

Arg Thr Gly Ser Gly Lys Ser Ser Phe Ser Leu Ala Phe Phe Arg Met
        195                 200                 205

Val Asp Thr Phe Glu Gly His Ile Ile Ile Asp Gly Ile Asp Ile Ala
    210                 215                 220

Lys Leu Pro Leu His Thr Leu Arg Ser Arg Leu Ser Ile Ile Leu Gln
225                 230                 235                 240
```

```
Asp Pro Val Leu Phe Ser Gly Thr Ile Arg Phe Asn Leu Asp Pro Glu
            245                 250                 255

Arg Lys Cys Ser Asp Ser Thr Leu Trp Glu Ala Leu Glu Ile Ala Gln
        260                 265                 270

Leu Lys Leu Val Val Lys Ala Leu Pro Gly Gly Leu Asp Ala Ile Ile
        275                 280                 285

Thr Glu Gly Gly Glu Asn Phe Ser Gln Gly Gln Arg Gln Leu Phe Cys
        290                 295                 300

Leu Ala Arg Ala Phe Val Arg Lys Thr Ser Ile Phe Ile Met Asp Glu
305                 310                 315                 320

Ala Thr Ala Ser Ile Asp Met Ala Thr Glu Asn Ile Leu Gln Lys Val
                325                 330                 335

Val Met Thr Ala Phe Ala Asp Arg Thr Val Val Thr Ile Ala His Arg
                340                 345                 350

Val His Thr Ile Leu Ser Ala Asp Leu Val Ile Val Leu Lys Arg Gly
        355                 360                 365

Ala Ile Leu Glu Phe Asp Lys Pro Glu Lys Leu Leu Ser Arg Lys Asp
        370                 375                 380

Ser Val Phe Ala Ser Phe Val Arg Ala Asp Lys
385                 390                 395

(2) INFORMATION FOR SEQ ID NO:4:

(i) SEQUENCE CHARACTERISTICS:
        (A) LENGTH: 5110 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:4:

CCCTTGTGAC AGGTCAGTCT TACGAGAATA TGGTAACTGA GATCATGTCA ATGGGCTATG      60

AACGAGAACA AGTAATTGCA GCCCTGAGAG CCAGCTTCAA CAACCCTGAT AGAGCTGTGG     120

AATATCTTCT AATGGGAATC CCTGGAGACT GAGGAGTTCC AGTACTCACA GCCTGTGGAG     180

GAGGATCAAC CACGGCCTGA CTTTCGCGGC CGCCGCGGGA GGCGCGCGGA GCCGGAGCCG     240

AGCCCGTGCG CGCGCCACCA TGCCTTTGGC CTTCTGCGGC ACCGAGAACC ACTCGGCCGC     300

CTACCGGGTG GACCAAGGCG TCCTCAACAA CGGCTGCTTC GTGGACGCGC TCAATGTGGT     360

GCCACATGTC TTTCTGCTCT TCATCACCTT CCCCATCCTC TTCATCGGAT GGGGCAGCCA     420

GAGCTCCAAG GTGCACATTC ACCACAGCAC CTGGCTCCAT TTCCCGGGGC ACAACCTGCG     480

CTGGATCCTG ACCTTCATAC TGCTCTTCGT CCTCGTGTGT GAGATCGCTG AGGGTATCCT     540

GTCTGACGGG GTGACAGAAT CCCGCCACCT CCACTTATAC ATGCCAGCTG GGATGGCATT     600

CATGGCTGCC ATCACCTCTG TGGTCTACTA CCATAACATT GAGACCTCTA ACTTTCCCAA     660

GCTGCTGATT GCTCTGCTCA TCTACTGGAC CCTGGCCTTC ATCACGAAGA CCATCAAGTT     720

CGTCAAGTTC TACGACCACG CCATTGGCTT CTCTCAGCTG CGCTTCTGCC TCACGGGGCT     780

TCTGGTGATC CTCTACGGGA TGCTGCTGCT TGTGGAGGTC AATGTCATCC GGGTGAGGAG     840

ATACGTCTTC TTCAAGACAC CAAGGGAAGT AAAGCCCCCC GAGGACCTAC AGGACCTGGG     900

TGTGCGCTTT CTGCAGCCCT TCGTTAACCT GCTATCAAAG GGGACCTACT GGTGGATGAA     960
```

```
TGCCTTCATC AAGACTGCTC ACAAGAAGCC CATCGACCTG CGGGCCATCG GAAGCTGCC     1020

CATTGCCATG AGAGCCCTCA CCAACTACCA GCGACTCTGC TTGGCCTTCG ATGCCCAGGC    1080

GCGGAAGGAC ACACAGAGCC AGCAGGGTGC CCGGGCCATC TGGAGGGCTC TCTGTCATGC    1140

CTTTGGGAGA CGGCTGGTCC TCAGCAGCAC ATTCCGTATC CTGGCCGACC TCCTGGGCTT    1200

TGCTGGGCCA CTCTGCATCT TCGGGATCGT GGACCACCTC GGGAAGGAGA ACCACGTCTT    1260

CCAGCCCAAG ACACAGTTTC TTGGAGTTTA CTTTGTCTCA TCCCAAGAGT TCCTCGGCAA    1320

TGCCTATGTC TTGGCTGTTC TTCTGTTCCT TGCCCTCCTG CTGCAAAGGA CCTTTCTACA    1380

AGCCTCGTAC TACGTTGCCA TTGAAACTGG GATCAACCTG AGAGGAGCAA TCCAGACCAA    1440

GATTTACAAT AAGATCATGC ACTTGTCTAC TTCCAACCTG TCCATGGGGG AAATGACTGC    1500

TGGGCAGATC TGCAACCTGG TGGCCATCGA CACCAACCAG CTCATGTGGT TTTTCTTCTT    1560

ATGCCCAAAC CTCTGGGCTA TGCCGGTACA GATCATTGTG GGCGTGATCC TCCTCTACTA    1620

CATCCTTGGG GTCAGCGCCT TGATTGGAGC GGCTGTCATC ATTCTGCTGG CTCCTGTACA    1680

GTACTTTGTG GCCACCAAGC TGTCCCAGGC ACAGCGGACG ACCCTGGAAT ATTCCAATGA    1740

GAGGCTGAAG CAGACCAATG AGATGCTCCG GGGCATCAAG TTGCTCAAGC TCTATGCGTG    1800

GGAGAACATC TTCTGCTCCA GGGTGGAGAA GACACGCAGG AAGGAAATGA CCAGCCTCAG    1860

GGCCTTCGCT GTCTACACCT CCATCTCCAT CTTCATGAAC ACAGCTATCC CCATCGCTGC    1920

TGTCCTCATC ACCTTCGTGG CCACGTCAG CTTCTTCAAA GAGTCGGACT TCTCGCCCTC     1980

GGTGGCCTTT GCCTCTCTCT CTCTCTTCCA CATCCTGGTC ACACCGCTGT TCCTGCTGTC    2040

TAGTGTGGTT CGGTCCACTG TCAAGGCCCT GGTGAGCGTG CAAAAGCTGA GTGAGTTCCT    2100

GTCCAGTGCA GAGATCCGTG AGGAACAGTG TGCCCCCCGA GAGCCCGCAC CCCAAGGCCA    2160

AGCGGGCAAG TACCAGGCGG TGCCCCTCAA GGTCGTAAAC CGCAAGCGCC CAGCCCGAGA    2220

AGAAGTCCGG GACCTCTTGG GCCCACTGCA GAGGCTGACT CCCAGCACGG ATGGAGACGC    2280

TGACAACTTC TGTGTCCAGA TCATCGGAGG CTTCTTCACC TGGACCCCTG ATGGAATCCC    2340

CACCCTGTCC AACATCACCA TCCGTATCCC CCGAGGTCAG CTGACCATGA TCGTGGGGCA    2400

GGTGGGCTGT GGCAAGTCCT CGCTCCTTCT GGCCACCCTG GGGGAGATGC AGAAGGTCTC    2460

TGGAGCTGTC TTCTGGAACA GCCTTCCAGA CAGCGAGGGG AGAAGACCCC AGCAACCCAG    2520

AGCGGGAGAC AGCGGCCGAT TCGGATGCCA GGAGCAGAGG CCCTGTGGCT ACGCATCTCA    2580

GAAACCATGG CTGCTAAATG CCACTGTGGA GGAGAACATC ACCTTCGAGA GTCCCTTCAA    2640

TAAGCAACGG TACAAGATGG TCATCGAAGC CTGCTCCCTG CAGCCAGACA TAGACATCCT    2700

GCCCCATGGA GACCAGACTC AGATTGGGGA ACGAGGCATC AACTTGAGTA CTGGTGGTCA    2760

GCGTCCAGAT CAGTGTAGAC CCGAGCCCTC TACCAGCACA CCAATGATTG TCTTTTTGGA    2820

TGACCCTTTC TCGGCTCTGG ATGTCCATCT GAGTGACCAC CTAATGCAGG CTGGCATCCT    2880

CGAGCTGCTC CGGGATGACA AGAGGACAGT GGTCTTGGTG ACCCACAAGC TACAGTACCT    2940

GCCTCATGCT GACTGGATCA TTGCTATGAA GGATGGCACC ATTCAGAGGG AGGGACACT     3000

CAAGGACTTC CAGAGGTCTG AGTGCCAGCT CTTTGAGCAT TGGAAGACCC TCATGAACCG    3060

GCAGGACCAA GAGCTGGAGA AGGAGACAGT CATGGAGAGA AAAGCCCCAG AGCCATCTCA    3120

GGGCCTGCCC CGTGCCATGT CCTCAAGAGA TGGCCTTCTG CTGGATGAGG ATGAGGAGGA    3180

AGAGGAGGCA GCCGAGAGCG AGGAAGATGA CAACTTATCC TCTGTGCTGC ATCAGCGAGC    3240

CAAGATCCCA TGGCGAGCCT GCACCAAGTA TTTGTCCTCT GCTGGCATCC TGCTCCTGTC    3300
```

```
CCTGCTTGTC TTCTCCCAGC TGCTCAAGCA CATGGTCTTG GTGGCCATTG ACTACTGGCT    3360

GGCCAAGTGG ACGGACAGTG CCCTGGTCCT GAGCCCCGCC GCCAGGAACT GCTCCCTCAG    3420

CCAGGAATGT GCCCTGGACC AATCTGTCTA TGCCATGGTA TTCACCGTGC CTGCAGCCT    3480

GGGTATCGCG CTGTGCCTTG TCACCTCTGT CACTGTGGAG TGGACGGGAC TGAAGGTGGC    3540

CAAGAGGCTG CATCGCAGCC TGCTCAACCG TATCATCCTG GCTCCCATGA GGTTCTTTGA    3600

GACCACGCCC CTGGGAGTA TCCTGAACAG ATTTTCATCT GACTGTAACA CCATTGACCA     3660

GCATATCCCG TCCACGCTGG AGTGCCTGAG CAGATCCACC TTACTCTGTG TCTCCGCCCT    3720

GGCTGTCATC TCCTACGTCA CGCCTGTGTT CCTAGTGGCC CTCTTACCCC TCGCCGTCGT    3780

GTGCTACTTC ATCCAGAAGT ACTTCCGAGT GGCGTCCAGG GACCTGCAGC AGCTGGACGA    3840

CACAACACAG CTCCCTCTGC TCTCACACTT TGCTGAAACT GTGGAAGGAC TCACCACCAT    3900

CCGTGCCTTC AGGTACGAGG CCCGGTTCCA GCAGAAGCTC CTAGAGTACA CCGACTCCAA    3960

CAACATTGCC TCTCTCTTCC TCACAGCAGC CAACAGGTGG CTGGAAGTCC GCATGGAGTA    4020

CATCGGAGCA TGCGTGGTAC TCATCGCCGC TGCCACCTCC ATCTCCAACT CCCTACACAG    4080

GGAGCTCTCA GCCGGCCTAG TAGGCCTGGG CCTCACCTAT GCCTTGATGG TCTCCAACTA    4140

CCTCAACTGG ATGGTGAGGA ACCTGGCAGA CATGGAGATC CAACTGGGAG CTGTGAAGGG    4200

TATCCACACA CTCCTGAAAA CTGAGGCAGA GAGCTATGAG GGGCTCCTGG CACCATCGCT    4260

GATCCCCAAG AACTGGCCAG ACCAAGGGAA GATCCAAATT CAAAACCTGA GTGTACGCTA    4320

TGACAGCTCC CTGAAGCCCG TGCTGAAGCA CGTCAACGCC CTCATCTCCC CAGGACAGAA    4380

GATTGGGATC TGCGGCCGCA CAGGCAGTGG AAAATCCTCC TTCTCTCTCG CCTTTTTCCG    4440

AATGGTGGAT ATGTTTGAAG GGCGTATCAT CATCGATGGC ATTGACATCG CCAAGCTGCC    4500

GCTGCACACG CTCGGCTCAC GCCTGTCTAT CATCCTACAG GACCCTGTTC TCTTCAGTGG    4560

TACCATCAGA TTCAACCTGG ACCCAGAGAA GAAATGCTCA GACAGCACGC TGTGGGAGGC    4620

TCTGGAGATC GCTCAGCTGA AGCTGGTGGT GAAGGCCCTG CCAGGAGGCC TGGATGCCAT    4680

CATCACGGAA GGAGGGGAGA ATTTTAGCCA GGGCCAGAGG CAGCTGTTCT GCCTGGCCCG    4740

GGCCTTTGTG AGGAAGACCA GCATCTTCAT CATGGATGAA GCAACTGCCT CCATCGACAT    4800

GGCTACGGAA AATATCCTCC AGAAGGTGGT GATGACAGCC TTCGCAGACC GCACCGTGGT    4860

CACCATCGCG CACCGCGTGC ACACCATCCT GAGTGCAGAC CTAGTGATGG TCCTGAAGAG    4920

GGGCGCGATC CTGGAGTTCG ACAAGCCGGA AAAGCTTCTC AGCCAGAAGG ACAGCGTCTT    4980

TGCCTCCTTT GTCCGCGCGG ACAAATGACC AGCCAGCGCC AAAGTGCCAC CCCACACCTC    5040

ACCTGCTTGC CATGGATTTC TTACTGTAAA TCACTTGTAA ATAAAGAAAC TAATTCTTTG    5100

CTAAAAAAAA                                                          5110
```

(2) INFORMATION FOR SEQ ID NO:5:

(i) SEQUENCE CHARACTERISTICS:
        (A) LENGTH: 5110 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS

6,054,313

41                                                                                42

-continued (B) LOCATION: 260..5004

(xi) SEQUENCE DESCRIPTION: SEQ ID NO:5:

```
CCCTTGTGAC AGGTCAGTCT TACGAGAATA TGGTAACTGA GATCATGTCA ATGGGCTATG     60

AACGAGAACA AGTAATTGCA GCCCTGAGAG CCAGCTTCAA CAACCCTGAT AGAGCTGTGG    120

AATATCTTCT AATGGGAATC CCTGGAGACT GAGGAGTTCC AGTACTCACA GCCTGTGGAG    180

GAGGATCAAC CACGGCCTGA CTTTCGCGGC CGCCGCGGGA GGCGCGCGGA GCCGGAGCCG    240

AGCCCGTGCG CGCGCCACC ATG CCT TTG GCC TTC TGC GGC ACC GAG AAC CAC    292
                     Met Pro Leu Ala Phe Cys Gly Thr Glu Asn His
                      1               5                  10
```

| | |
|---|---|
| TCG GCC GCC TAC CGG GTG GAC CAA GGC GTC CTC AAC AAC GGC TGC TTC<br>Ser Ala Ala Tyr Arg Val Asp Gln Gly Val Leu Asn Asn Gly Cys Phe<br>               15                    20                    25 | 340 |
| GTG GAC GCG CTC AAT GTG GTG CCA CAT GTC TTT CTG CTC TTC ATC ACC<br>Val Asp Ala Leu Asn Val Val Pro His Val Phe Leu Leu Phe Ile Thr<br>         30                   35                    40 | 388 |
| TTC CCC ATC CTC TTC ATC GGA TGG GGC AGC CAG AGC TCC AAG GTG CAC<br>Phe Pro Ile Leu Phe Ile Gly Trp Gly Ser Gln Ser Ser Lys Val His<br>     45                   50                    55 | 436 |
| ATT CAC CAC AGC ACC TGG CTC CAT TTC CCG GGG CAC AAC CTG CGC TGG<br>Ile His His Ser Thr Trp Leu His Phe Pro Gly His Asn Leu Arg Trp<br>60                   65                    70                    75 | 484 |
| ATC CTG ACC TTC ATA CTG CTC TTC GTC CTC GTG TGT GAG ATC GCT GAG<br>Ile Leu Thr Phe Ile Leu Leu Phe Val Leu Val Cys Glu Ile Ala Glu<br>               80                    85                    90 | 532 |
| GGT ATC CTG TCT GAC GGG GTG ACA GAA TCC CGC CAC CTC CAC TTA TAC<br>Gly Ile Leu Ser Asp Gly Val Thr Glu Ser Arg His Leu His Leu Tyr<br>     95                   100                  105 | 580 |
| ATG CCA GCT GGG ATG GCA TTC ATG GCT GCC ATC ACC TCT GTG GTC TAC<br>Met Pro Ala Gly Met Ala Phe Met Ala Ala Ile Thr Ser Val Val Tyr<br>110                      115                    120 | 628 |
| TAC CAT AAC ATT GAG ACC TCT AAC TTT CCC AAG CTG CTG ATT GCT CTG<br>Tyr His Asn Ile Glu Thr Ser Asn Phe Pro Lys Leu Leu Ile Ala Leu<br>     125                 130                  135 | 676 |
| CTC ATC TAC TGG ACC CTG GCC TTC ATC ACG AAG ACC ATC AAG TTC GTC<br>Leu Ile Tyr Trp Thr Leu Ala Phe Ile Thr Lys Thr Ile Lys Phe Val<br>140                      145                    150                  155 | 724 |
| AAG TTC TAC GAC CAC GCC ATT GGC TTC TCT CAG CTG CGC TTC TGC CTC<br>Lys Phe Tyr Asp His Ala Ile Gly Phe Ser Gln Leu Arg Phe Cys Leu<br>               160                    165                  170 | 772 |
| ACG GGG CTT CTG GTG ATC CTC TAC GGG ATG CTG CTG CTT GTG GAG GTC<br>Thr Gly Leu Leu Val Ile Leu Tyr Gly Met Leu Leu Leu Val Glu Val<br>               175                    180                    185 | 820 |
| AAT GTC ATC CGG GTG AGG AGA TAC GTC TTC TTC AAG ACA CCA AGG GAA<br>Asn Val Ile Arg Val Arg Arg Tyr Val Phe Phe Lys Thr Pro Arg Glu<br>190                      195                    200 | 868 |
| GTA AAG CCC CCC GAG GAC CTA CAG GAC CTG GGT GTG CGC TTT CTG CAG<br>Val Lys Pro Pro Glu Asp Leu Gln Asp Leu Gly Val Arg Phe Leu Gln<br>     205                 210                  215 | 916 |
| CCC TTC GTT AAC CTG CTA TCA AAG GGG ACC TAC TGG TGG ATG AAT GCC<br>Pro Phe Val Asn Leu Leu Ser Lys Gly Thr Tyr Trp Trp Met Asn Ala<br>220                      225                    230                  235 | 964 |
| TTC ATC AAG ACT GCT CAC AAG AAG CCC ATC GAC CTG CGG GCC ATC GGG<br>Phe Ile Lys Thr Ala His Lys Lys Pro Ile Asp Leu Arg Ala Ile Gly<br>               240                    245                  250 | 1012 |
| AAG CTG CCC ATT GCC ATG AGA GCC CTC ACC AAC TAC CAG CGA CTC TGC<br>Lys Leu Pro Ile Ala Met Arg Ala Leu Thr Asn Tyr Gln Arg Leu Cys<br>               255                    260                  265 | 1060 |

-continued

```
TTG GCC TTC GAT GCC CAG GCG CGG AAG GAC ACA CAG AGC CAG CAG GGT      1108
Leu Ala Phe Asp Ala Gln Ala Arg Lys Asp Thr Gln Ser Gln Gln Gly
            270                 275                 280

GCC CGG GCC ATC TGG AGG GCT CTC TGT CAT GCC TTT GGG AGA CGG CTG      1156
Ala Arg Ala Ile Trp Arg Ala Leu Cys His Ala Phe Gly Arg Arg Leu
285                 290                 295

GTC CTC AGC AGC ACA TTC CGT ATC CTG GCC GAC CTC CTG GGC TTT GCT      1204
Val Leu Ser Ser Thr Phe Arg Ile Leu Ala Asp Leu Leu Gly Phe Ala
300                 305                 310                 315

GGG CCA CTC TGC ATC TTC GGG ATC GTG GAC CAC CTC GGG AAG GAG AAC      1252
Gly Pro Leu Cys Ile Phe Gly Ile Val Asp His Leu Gly Lys Glu Asn
            320                 325                 330

CAC GTC TTC CAG CCC AAG ACA CAG TTT CTT GGA GTT TAC TTT GTC TCA      1300
His Val Phe Gln Pro Lys Thr Gln Phe Leu Gly Val Tyr Phe Val Ser
            335                 340                 345

TCC CAA GAG TTC CTC GGC AAT GCC TAT GTC TTG GCT GTT CTC CTG TTC      1348
Ser Gln Glu Phe Leu Gly Asn Ala Tyr Val Leu Ala Val Leu Leu Phe
            350                 355                 360

CTT GCC CTC CTG CAA AGG ACC TTT CTA CAA GCC TCG TAC TAC GTT          1396
Leu Ala Leu Leu Leu Gln Arg Thr Phe Leu Gln Ala Ser Tyr Tyr Val
    365                 370                 375

GCC ATT GAA ACT GGG ATC AAC CTG AGA GGA GCA ATC CAG ACC AAG ATT      1444
Ala Ile Glu Thr Gly Ile Asn Leu Arg Gly Ala Ile Gln Thr Lys Ile
380                 385                 390                 395

TAC AAT AAG ATC ATG CAC TTG TCT ACT TCC AAC CTG TCC ATG GGG GAA      1492
Tyr Asn Lys Ile Met His Leu Ser Thr Ser Asn Leu Ser Met Gly Glu
            400                 405                 410

ATG ACT GCT GGG CAG ATC TGC AAC CTG GTG GCC ATC GAC ACC AAC CAG      1540
Met Thr Ala Gly Gln Ile Cys Asn Leu Val Ala Ile Asp Thr Asn Gln
            415                 420                 425

CTC ATG TGG TTT TTC TTC TTA TGC CCA AAC CTC TGG GCT ATG CCG GTA      1588
Leu Met Trp Phe Phe Phe Leu Cys Pro Asn Leu Trp Ala Met Pro Val
            430                 435                 440

CAG ATC ATT GTG GGC GTG ATC CTC CTC TAC TAC ATC CTT GGG GTC AGC      1636
Gln Ile Ile Val Gly Val Ile Leu Leu Tyr Tyr Ile Leu Gly Val Ser
            445                 450                 455

GCC TTG ATT GGA GCG GCT GTC ATC ATT CTG CTG GCT CCT GTA CAG TAC      1684
Ala Leu Ile Gly Ala Ala Val Ile Ile Leu Leu Ala Pro Val Gln Tyr
460                 465                 470                 475

TTT GTG GCC ACC AAG CTG TCC CAG GCA CAG CGG ACG ACC CTG GAA TAT      1732
Phe Val Ala Thr Lys Leu Ser Gln Ala Gln Arg Thr Thr Leu Glu Tyr
            480                 485                 490

TCC AAT GAG AGG CTG AAG CAG ACC AAT GAG ATG CTC CGG GGC ATC AAG      1780
Ser Asn Glu Arg Leu Lys Gln Thr Asn Glu Met Leu Arg Gly Ile Lys
            495                 500                 505

TTG CTC AAG CTC TAT GCG TGG GAG AAC ATC TTC TGC TCC AGG GTG GAG      1828
Leu Leu Lys Leu Tyr Ala Trp Glu Asn Ile Phe Cys Ser Arg Val Glu
            510                 515                 520

AAG ACA CGC AGG AAG GAA ATG ACC AGC CTC AGG GCC TTC GCT GTC TAC      1876
Lys Thr Arg Arg Lys Glu Met Thr Ser Leu Arg Ala Phe Ala Val Tyr
            525                 530                 535

ACC TCC ATC TCC ATC TTC ATG AAC ACA GCT ATC CCC ATC GCT GCT GTC      1924
Thr Ser Ile Ser Ile Phe Met Asn Thr Ala Ile Pro Ile Ala Ala Val
540                 545                 550                 555

CTC ATC ACC TTC GTG GGC CAC GTC AGC TTC TTC AAA GAG TCG GAC TTC      1972
Leu Ile Thr Phe Val Gly His Val Ser Phe Phe Lys Glu Ser Asp Phe
            560                 565                 570

TCG CCC TCG GTG GCC TTT GCC TCT CTC TCT CTC TTC CAC ATC CTG GTC      2020
Ser Pro Ser Val Ala Phe Ala Ser Leu Ser Leu Phe His Ile Leu Val
```

-continued

|  |  |  |  |  |  | 575 |  |  |  | 580 |  |  |  | 585 |  |  |  |
|---|---|---|---|---|---|---|---|---|---|---|---|---|---|---|---|---|---|
| ACA | CCG | CTG | TTC | CTG | CTG | TCT | AGT | GTG | GTT | CGG | TCC | ACT | GTC | AAG | GCC |  | 2068 |
| Thr | Pro | Leu | Phe | Leu | Leu | Ser | Ser | Val | Val | Arg | Ser | Thr | Val | Lys | Ala |  |  |
|  |  | 590 |  |  |  | 595 |  |  |  | 600 |  |  |  |  |  |  |  |

```
ACA CCG CTG TTC CTG CTG TCT AGT GTG GTT CGG TCC ACT GTC AAG GCC        2068
Thr Pro Leu Phe Leu Leu Ser Ser Val Val Arg Ser Thr Val Lys Ala
        590             595             600

CTG GTG AGC GTG CAA AAG CTG AGT GAG TTC CTG TCC AGT GCA GAG ATC        2116
Leu Val Ser Val Gln Lys Leu Ser Glu Phe Leu Ser Ser Ala Glu Ile
        605             610             615

CGT GAG GAA CAG TGT GCC CCC CGA GAG CCC GCA CCC CAA GGC CAA GCG        2164
Arg Glu Glu Gln Cys Ala Pro Arg Glu Pro Ala Pro Gln Gly Gln Ala
620             625             630             635

GGC AAG TAC CAG GCG GTG CCC CTC AAG GTC GTA AAC CGC AAG CGC CCA        2212
Gly Lys Tyr Gln Ala Val Pro Leu Lys Val Val Asn Arg Lys Arg Pro
                640             645             650

GCC CGA GAA GAA GTC CGG GAC CTC TTG GGC CCA CTG CAG AGG CTG ACT        2260
Ala Arg Glu Glu Val Arg Asp Leu Leu Gly Pro Leu Gln Arg Leu Thr
                655             660             665

CCC AGC ACG GAT GGA GAC GCT GAC AAC TTC TGT GTC CAG ATC ATC GGA        2308
Pro Ser Thr Asp Gly Asp Ala Asp Asn Phe Cys Val Gln Ile Ile Gly
                670             675             680

GGC TTC TTC ACC TGG ACC CCT GAT GGA ATC CCC ACC CTG TCC AAC ATC        2356
Gly Phe Phe Thr Trp Thr Pro Asp Gly Ile Pro Thr Leu Ser Asn Ile
        685             690             695

ACC ATC CGT ATC CCC CGA GGT CAG CTG ACC ATG ATC GTG GGG CAG GTG        2404
Thr Ile Arg Ile Pro Arg Gly Gln Leu Thr Met Ile Val Gly Gln Val
700             705             710             715

GGC TGT GGC AAG TCC TCG CTC CTT CTG GCC ACC CTG GGG GAG ATG CAG        2452
Gly Cys Gly Lys Ser Ser Leu Leu Leu Ala Thr Leu Gly Glu Met Gln
                720             725             730

AAG GTC TCT GGA GCT GTC TTC TGG AAC AGC CTT CCA GAC AGC GAG GGG        2500
Lys Val Ser Gly Ala Val Phe Trp Asn Ser Leu Pro Asp Ser Glu Gly
                735             740             745

AGA AGA CCC CAG CAA CCC AGA GCG GGA GAC AGC GGC CGA TTC GGA TGC        2548
Arg Arg Pro Gln Gln Pro Arg Ala Gly Asp Ser Gly Arg Phe Gly Cys
        750             755             760

CAG GAG CAG AGG CCC TGT GGC TAC GCA TCT CAG AAA CCA TGG CTG CTA        2596
Gln Glu Gln Arg Pro Cys Gly Tyr Ala Ser Gln Lys Pro Trp Leu Leu
765             770             775

AAT GCC ACT GTG GAG GAG AAC ATC ACC TTC GAG AGT CCC TTC AAT AAG        2644
Asn Ala Thr Val Glu Glu Asn Ile Thr Phe Glu Ser Pro Phe Asn Lys
780             785             790             795

CAA CGG TAC AAG ATG GTC ATC GAA GCC TGC TCC CTG CAG CCA GAC ATA        2692
Gln Arg Tyr Lys Met Val Ile Glu Ala Cys Ser Leu Gln Pro Asp Ile
                800             805             810

GAC ATC CTG CCC CAT GGA GAC CAG ACT CAG ATT GGG GAA CGA GGC ATC        2740
Asp Ile Leu Pro His Gly Asp Gln Thr Gln Ile Gly Glu Arg Gly Ile
                815             820             825

AAC TTG AGT ACT GGT GGT CAG CGT CCA GAT CAG TGT AGA CCC GAG CCC        2788
Asn Leu Ser Thr Gly Gly Gln Arg Pro Asp Gln Cys Arg Pro Glu Pro
        830             835             840

TCT ACC AGC ACA CCA ATG ATT GTC TTT TTG GAT GAC CCT TTC TCG GCT        2836
Ser Thr Ser Thr Pro Met Ile Val Phe Leu Asp Asp Pro Phe Ser Ala
        845             850             855

CTG GAT GTC CAT CTG AGT GAC CAC CTA ATG CAG GCT GGC ATC CTC GAG        2884
Leu Asp Val His Leu Ser Asp His Leu Met Gln Ala Gly Ile Leu Glu
860             865             870             875

CTG CTC CGG GAT GAC AAG AGG ACA GTG GTC TTG GTG ACC CAC AAG CTA        2932
Leu Leu Arg Asp Asp Lys Arg Thr Val Val Leu Val Thr His Lys Leu
                880             885             890

CAG TAC CTG CCT CAT GCT GAC TGG ATC ATT GCT ATG AAG GAT GGC ACC        2980
```

```
Gln Tyr Leu Pro His Ala Asp Trp Ile Ile Ala Met Lys Asp Gly Thr
            895                 900                 905

ATT CAG AGG GAG GGG ACA CTC AAG GAC TTC CAG AGG TCT GAG TGC CAG      3028
Ile Gln Arg Glu Gly Thr Leu Lys Asp Phe Gln Arg Ser Glu Cys Gln
        910                 915                 920

CTC TTT GAG CAT TGG AAG ACC CTC ATG AAC CGG CAG GAC CAA GAG CTG      3076
Leu Phe Glu His Trp Lys Thr Leu Met Asn Arg Gln Asp Gln Glu Leu
            925                 930                 935

GAG AAG GAG ACA GTC ATG GAG AGA AAA GCC CCA GAG CCA TCT CAG GGC      3124
Glu Lys Glu Thr Val Met Glu Arg Lys Ala Pro Glu Pro Ser Gln Gly
940                 945                 950                 955

CTG CCC CGT GCC ATG TCC TCA AGA GAT GGC CTT CTG CTG GAT GAG GAT      3172
Leu Pro Arg Ala Met Ser Ser Arg Asp Gly Leu Leu Leu Asp Glu Asp
                960                 965                 970

GAG GAG GAA GAG GAG GCA GCC GAG AGC GAG GAA GAT GAC AAC TTA TCC      3220
Glu Glu Glu Glu Glu Ala Ala Glu Ser Glu Glu Asp Asp Asn Leu Ser
            975                 980                 985

TCT GTG CTG CAT CAG CGA GCC AAG ATC CCA TGG CGA GCC TGC ACC AAG      3268
Ser Val Leu His Gln Arg Ala Lys Ile Pro Trp Arg Ala Cys Thr Lys
        990                 995                 1000

TAT TTG TCC TCT GCT GGC ATC CTG CTC CTG TCC CTG CTT GTC TTC TCC      3316
Tyr Leu Ser Ser Ala Gly Ile Leu Leu Leu Ser Leu Leu Val Phe Ser
    1005                1010                1015

CAG CTG CTC AAG CAC ATG GTC TTG GTG GCC ATT GAC TAC TGG CTG GCC      3364
Gln Leu Leu Lys His Met Val Leu Val Ala Ile Asp Tyr Trp Leu Ala
1020                1025                1030                1035

AAG TGG ACG GAC AGT GCC CTG GTC CTG AGC CCC GCC GCC AGG AAC TGC      3412
Lys Trp Thr Asp Ser Ala Leu Val Leu Ser Pro Ala Ala Arg Asn Cys
                1040                1045                1050

TCC CTC AGC CAG GAA TGT GCC CTG GAC CAA TCT GTC TAT GCC ATG GTA      3460
Ser Leu Ser Gln Glu Cys Ala Leu Asp Gln Ser Val Tyr Ala Met Val
            1055                1060                1065

TTC ACC GTG CTC TGC AGC CTG GGT ATC GCG CTG TGC CTT GTC ACC TCT      3508
Phe Thr Val Leu Cys Ser Leu Gly Ile Ala Leu Cys Leu Val Thr Ser
        1070                1075                1080

GTC ACT GTG GAG TGG ACG GGA CTG AAG GTG GCC AAG AGG CTG CAT CGC      3556
Val Thr Val Glu Trp Thr Gly Leu Lys Val Ala Lys Arg Leu His Arg
    1085                1090                1095

AGC CTG CTC AAC CGT ATC ATC CTG GCT CCC ATG AGG TTC TTT GAG ACC      3604
Ser Leu Leu Asn Arg Ile Ile Leu Ala Pro Met Arg Phe Phe Glu Thr
1100                1105                1110                1115

ACG CCC CTG GGG AGT ATC CTG AAC AGA TTT TCA TCT GAC TGT AAC ACC      3652
Thr Pro Leu Gly Ser Ile Leu Asn Arg Phe Ser Ser Asp Cys Asn Thr
                1120                1125                1130

ATT GAC CAG CAT ATC CCG TCC ACG CTG GAG TGC CTG AGC AGA TCC ACC      3700
Ile Asp Gln His Ile Pro Ser Thr Leu Glu Cys Leu Ser Arg Ser Thr
            1135                1140                1145

TTA CTC TGT GTC TCC GCC CTG GCT GTC ATC TCC TAC GTC ACG CCT GTG      3748
Leu Leu Cys Val Ser Ala Leu Ala Val Ile Ser Tyr Val Thr Pro Val
        1150                1155                1160

TTC CTA GTG GCC CTC TTA CCC CTC GCC GTC GTG TGC TAC TTC ATC CAG      3796
Phe Leu Val Ala Leu Leu Pro Leu Ala Val Val Cys Tyr Phe Ile Gln
    1165                1170                1175

AAG TAC TTC CGA GTG GCG TCC AGG GAC CTG CAG CAG CTG GAC GAC ACA      3844
Lys Tyr Phe Arg Val Ala Ser Arg Asp Leu Gln Gln Leu Asp Asp Thr
1180                1185                1190                1195

ACA CAG CTC CCT CTG CTC TCA CAC TTT GCT GAA ACT GTG GAA GGA CTC      3892
Thr Gln Leu Pro Leu Leu Ser His Phe Ala Glu Thr Val Glu Gly Leu
                1200                1205                1210
```

-continued

| | |
|---|---|
| ACC ACC ATC CGT GCC TTC AGG TAC GAG GCC CGG TTC CAG CAG AAG CTC<br>Thr Thr Ile Arg Ala Phe Arg Tyr Glu Ala Arg Phe Gln Gln Lys Leu<br>            1215                       1220                       1225 | 3940 |
| CTA GAG TAC ACC GAC TCC AAC AAC ATT GCC TCT CTC TTC CTC ACA GCA<br>Leu Glu Tyr Thr Asp Ser Asn Asn Ile Ala Ser Leu Phe Leu Thr Ala<br>      1230                       1235                       1240 | 3988 |
| GCC AAC AGG TGG CTG GAA GTC CGC ATG GAG TAC ATC GGA GCA TGC GTG<br>Ala Asn Arg Trp Leu Glu Val Arg Met Glu Tyr Ile Gly Ala Cys Val<br>    1245                      1250                     1255 | 4036 |
| GTA CTC ATC GCC GCT GCC ACC TCC ATC TCC AAC TCC CTA CAC AGG GAG<br>Val Leu Ile Ala Ala Ala Thr Ser Ile Ser Asn Ser Leu His Arg Glu<br>1260                   1265                    1270                   1275 | 4084 |
| CTC TCA GCC GGC CTA GTA GGC CTG GGC CTC ACC TAT GCC TTG ATG GTC<br>Leu Ser Ala Gly Leu Val Gly Leu Gly Leu Thr Tyr Ala Leu Met Val<br>           1280                       1285                    1290 | 4132 |
| TCC AAC TAC CTC AAC TGG ATG GTG AGG AAC CTG GCA GAC ATG GAG ATC<br>Ser Asn Tyr Leu Asn Trp Met Val Arg Asn Leu Ala Asp Met Glu Ile<br>                1295                    1300                    1305 | 4180 |
| CAA CTG GGA GCT GTG AAG GGT ATC CAC ACA CTC CTG AAA ACT GAG GCA<br>Gln Leu Gly Ala Val Lys Gly Ile His Thr Leu Leu Lys Thr Glu Ala<br>        1310                       1315                    1320 | 4228 |
| GAG AGC TAT GAG GGG CTC CTG GCA CCA TCG CTG ATC CCC AAG AAC TGG<br>Glu Ser Tyr Glu Gly Leu Leu Ala Pro Ser Leu Ile Pro Lys Asn Trp<br>1325                   1330                    1335 | 4276 |
| CCA GAC CAA GGG AAG ATC CAA ATT CAA AAC CTG AGT GTA CGC TAT GAC<br>Pro Asp Gln Gly Lys Ile Gln Ile Gln Asn Leu Ser Val Arg Tyr Asp<br>1340                   1345                    1350                   1355 | 4324 |
| AGC TCC CTG AAG CCC GTG CTG AAG CAC GTC AAC GCC CTC ATC TCC CCA<br>Ser Ser Leu Lys Pro Val Leu Lys His Val Asn Ala Leu Ile Ser Pro<br>                  1360                    1365                    1370 | 4372 |
| GGA CAG AAG ATT GGG ATC TGC GGC CGC ACA GGC AGT GGA AAA TCC TCC<br>Gly Gln Lys Ile Gly Ile Cys Gly Arg Thr Gly Ser Gly Lys Ser Ser<br>        1375                       1380                    1385 | 4420 |
| TTC TCT CTC GCC TTT TTC CGA ATG GTG GAT ATG TTT GAA GGG CGT ATC<br>Phe Ser Leu Ala Phe Phe Arg Met Val Asp Met Phe Glu Gly Arg Ile<br>           1390                       1395                    1400 | 4468 |
| ATC ATC GAT GGC ATT GAC ATC GCC AAG CTG CCG CTG CAC ACG CTC GGC<br>Ile Ile Asp Gly Ile Asp Ile Ala Lys Leu Pro Leu His Thr Leu Gly<br>               1405                    1410                    1415 | 4516 |
| TCA CGC CTG TCT ATC ATC CTA CAG GAC CCT GTT CTC TTC AGT GGT ACC<br>Ser Arg Leu Ser Ile Ile Leu Gln Asp Pro Val Leu Phe Ser Gly Thr<br>1420                   1425                    1430                   1435 | 4564 |
| ATC AGA TTC AAC CTG GAC CCA GAG AAG AAA TGC TCA GAC AGC ACG CTG<br>Ile Arg Phe Asn Leu Asp Pro Glu Lys Lys Cys Ser Asp Ser Thr Leu<br>            1440                       1445                    1450 | 4612 |
| TGG GAG GCT CTG GAG ATC GCT CAG CTG AAG CTG GTG GTG AAG GCC CTG<br>Trp Glu Ala Leu Glu Ile Ala Gln Leu Lys Leu Val Val Lys Ala Leu<br>         1455                      1460                    1465 | 4660 |
| CCA GGA GGC CTG GAT GCC ATC ATC ACG GAA GGA GGG GAG AAT TTT AGC<br>Pro Gly Gly Leu Asp Ala Ile Ile Thr Glu Gly Gly Glu Asn Phe Ser<br>             1470                    1475                    1480 | 4708 |
| CAG GGC CAG AGG CAG CTG TTC TGC CTG GCC CGG GCC TTT GTG AGG AAG<br>Gln Gly Gln Arg Gln Leu Phe Cys Leu Ala Arg Ala Phe Val Arg Lys<br>1485                   1490                    1495 | 4756 |
| ACC AGC ATC TTC ATC ATG GAT GAA GCA ACT GCC TCC ATC GAC ATG GCT<br>Thr Ser Ile Phe Ile Met Asp Glu Ala Thr Ala Ser Ile Asp Met Ala<br>1500                   1505                    1510                   1515 | 4804 |
| ACG GAA AAT ATC CTC CAG AAG GTG GTG ATG ACA GCC TTC GCA GAC CGC<br>Thr Glu Asn Ile Leu Gln Lys Val Val Met Thr Ala Phe Ala Asp Arg<br>                1520                    1525                    1530 | 4852 |

-continued

```
ACC GTG GTC ACC ATC GCG CAC CGC GTG CAC ACC ATC CTG AGT GCA GAC       4900
Thr Val Val Thr Ile Ala His Arg Val His Thr Ile Leu Ser Ala Asp
         1535                1540                1545

CTA GTG ATG GTC CTG AAG AGG GGC GCG ATC CTG GAG TTC GAC AAG CCG       4948
Leu Val Met Val Leu Lys Arg Gly Ala Ile Leu Glu Phe Asp Lys Pro
         1550                1555                1560

GAA AAG CTT CTC AGC CAG AAG GAC AGC GTC TTT GCC TCC TTT GTC CGC       4996
Glu Lys Leu Leu Ser Gln Lys Asp Ser Val Phe Ala Ser Phe Val Arg
         1565                1570                1575

GCG GAC AA ATGACCAGCC AGCGCCAAAG TGCCACCCCA CACCTCACCT GCTTGCCATG      5054
Ala Asp
1580

GATTTCTTAC TGTAAATCAC TTGTAAATAA AGAAACTAAT TCTTTGCTAA AAAAAA          5110
```

(2) INFORMATION FOR SEQ ID NO:6:

(i) SEQUENCE CHARACTERISTICS:
        (A) LENGTH: 1581 amino acids
        (B) TYPE: amino acid
        (D) TOPOLOGY: linear (ii) MOLECULE TYPE: protein (xi) SEQUENCE DESCRIPTION: SEQ ID NO:6:

```
Met Pro Leu Ala Phe Cys Gly Thr Glu Asn His Ser Ala Ala Tyr Arg
 1               5                  10                  15

Val Asp Gln Gly Val Leu Asn Asn Gly Cys Phe Val Asp Ala Leu Asn
            20                  25                  30

Val Val Pro His Val Phe Leu Leu Phe Ile Thr Phe Pro Ile Leu Phe
        35                  40                  45

Ile Gly Trp Gly Ser Gln Ser Ser Lys Val His Ile His His Ser Thr
 50                  55                  60

Trp Leu His Phe Pro Gly His Asn Leu Arg Trp Ile Leu Thr Phe Ile
 65                  70                  75                  80

Leu Leu Phe Val Leu Val Cys Glu Ile Ala Glu Gly Ile Leu Ser Asp
                85                  90                  95

Gly Val Thr Glu Ser Arg His Leu His Leu Tyr Met Pro Ala Gly Met
            100                 105                 110

Ala Phe Met Ala Ala Ile Thr Ser Val Val Tyr Tyr His Asn Ile Glu
        115                 120                 125

Thr Ser Asn Phe Pro Lys Leu Leu Ile Ala Leu Leu Ile Tyr Trp Thr
130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Val Glu Val Asn Val Ile Arg Val
            180                 185                 190

Arg Arg Tyr Val Phe Phe Lys Thr Pro Arg Glu Val Lys Pro Pro Glu
        195                 200                 205

Asp Leu Gln Asp Leu Gly Val Arg Phe Leu Gln Pro Phe Val Asn Leu
    210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Gly Lys Leu Pro Ile Ala
                245                 250                 255
```

-continued

```
Met Arg Ala Leu Thr Asn Tyr Gln Arg Leu Cys Leu Ala Phe Asp Ala
            260                 265                 270

Gln Ala Arg Lys Asp Thr Gln Ser Gln Gln Gly Ala Arg Ala Ile Trp
        275                 280                 285

Arg Ala Leu Cys His Ala Phe Gly Arg Arg Leu Val Leu Ser Ser Thr
    290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

Gly Asn Ala Tyr Val Leu Ala Val Leu Leu Phe Leu Ala Leu Leu Leu
        355                 360                 365

Gln Arg Thr Phe Leu Gln Ala Ser Tyr Tyr Val Ala Ile Glu Thr Gly
    370                 375                 380

Ile Asn Leu Arg Gly Ala Ile Gln Thr Lys Ile Tyr Asn Lys Ile Met
385                 390                 395                 400

His Leu Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
            420                 425                 430

Phe Leu Cys Pro Asn Leu Trp Ala Met Pro Val Gln Ile Ile Val Gly
        435                 440                 445

Val Ile Leu Leu Tyr Tyr Ile Leu Gly Val Ser Ala Leu Ile Gly Ala
    450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu Tyr Ser Asn Glu Arg Leu
                485                 490                 495

Lys Gln Thr Asn Glu Met Leu Arg Gly Ile Lys Leu Leu Lys Leu Tyr
            500                 505                 510

Ala Trp Glu Asn Ile Phe Cys Ser Arg Val Glu Lys Thr Arg Arg Lys
        515                 520                 525

Glu Met Thr Ser Leu Arg Ala Phe Ala Val Tyr Thr Ser Ile Ser Ile
    530                 535                 540

Phe Met Asn Thr Ala Ile Pro Ile Ala Ala Val Leu Ile Thr Phe Val
545                 550                 555                 560

Gly His Val Ser Phe Phe Lys Glu Ser Asp Phe Ser Pro Ser Val Ala
                565                 570                 575

Phe Ala Ser Leu Ser Leu Phe His Ile Leu Val Thr Pro Leu Phe Leu
            580                 585                 590

Leu Ser Ser Val Val Arg Ser Thr Val Lys Ala Leu Val Ser Val Gln
        595                 600                 605

Lys Leu Ser Glu Phe Leu Ser Ser Ala Glu Ile Arg Glu Glu Gln Cys
    610                 615                 620

Ala Pro Arg Glu Pro Ala Pro Gln Gly Gln Ala Gly Lys Tyr Gln Ala
625                 630                 635                 640

Val Pro Leu Lys Val Val Asn Arg Lys Arg Pro Ala Arg Glu Glu Val
                645                 650                 655

Arg Asp Leu Leu Gly Pro Leu Gln Arg Leu Thr Pro Ser Thr Asp Gly
            660                 665                 670

Asp Ala Asp Asn Phe Cys Val Gln Ile Ile Gly Gly Phe Phe Thr Trp
```

-continued

```
                675                 680                 685
Thr Pro Asp Gly Ile Pro Thr Leu Ser Asn Ile Thr Ile Arg Ile Pro
        690                 695                 700

Arg Gly Gln Leu Thr Met Ile Val Gly Gln Val Gly Cys Gly Lys Ser
705                 710                 715                 720

Ser Leu Leu Leu Ala Thr Leu Gly Glu Met Gln Lys Val Ser Gly Ala
                725                 730                 735

Val Phe Trp Asn Ser Leu Pro Asp Ser Glu Gly Arg Arg Pro Gln Gln
            740                 745                 750

Pro Arg Ala Gly Asp Ser Gly Arg Phe Gly Cys Gln Glu Gln Arg Pro
        755                 760                 765

Cys Gly Tyr Ala Ser Gln Lys Pro Trp Leu Leu Asn Ala Thr Val Glu
    770                 775                 780

Glu Asn Ile Thr Phe Glu Ser Pro Phe Asn Lys Gln Arg Tyr Lys Met
785                 790                 795                 800

Val Ile Glu Ala Cys Ser Leu Gln Pro Asp Ile Asp Ile Leu Pro His
                805                 810                 815

Gly Asp Gln Thr Gln Ile Gly Glu Arg Gly Ile Asn Leu Ser Thr Gly
            820                 825                 830

Gly Gln Arg Pro Asp Gln Cys Arg Pro Glu Pro Ser Thr Ser Thr Pro
        835                 840                 845

Met Ile Val Phe Leu Asp Asp Pro Phe Ser Ala Leu Asp Val His Leu
    850                 855                 860

Ser Asp His Leu Met Gln Ala Gly Ile Leu Glu Leu Leu Arg Asp Asp
865                 870                 875                 880

Lys Arg Thr Val Val Leu Val Thr His Lys Leu Gln Tyr Leu Pro His
                885                 890                 895

Ala Asp Trp Ile Ile Ala Met Lys Asp Gly Thr Ile Gln Arg Glu Gly
            900                 905                 910

Thr Leu Lys Asp Phe Gln Arg Ser Glu Cys Gln Leu Phe Glu His Trp
        915                 920                 925

Lys Thr Leu Met Asn Arg Gln Asp Gln Glu Leu Glu Lys Glu Thr Val
    930                 935                 940

Met Glu Arg Lys Ala Pro Glu Pro Ser Gln Gly Leu Pro Arg Ala Met
945                 950                 955                 960

Ser Ser Arg Asp Gly Leu Leu Leu Asp Glu Asp Glu Glu Glu Glu Glu
                965                 970                 975

Ala Ala Glu Ser Glu Glu Asp Asp Asn Leu Ser Ser Val Leu His Gln
            980                 985                 990

Arg Ala Lys Ile Pro Trp Arg Ala Cys Thr Lys Tyr Leu Ser Ser Ala
        995                 1000                1005

Gly Ile Leu Leu Leu Ser Leu Leu Val Phe Ser Gln Leu Leu Lys His
    1010                1015                1020

Met Val Leu Val Ala Ile Asp Tyr Trp Leu Ala Lys Trp Thr Asp Ser
1025                1030                1035                1040

Ala Leu Val Leu Ser Pro Ala Ala Arg Asn Cys Ser Leu Ser Gln Glu
                1045                1050                1055

Cys Ala Leu Asp Gln Ser Val Tyr Ala Met Val Phe Thr Val Leu Cys
            1060                1065                1070

Ser Leu Gly Ile Ala Leu Cys Leu Val Thr Ser Val Thr Val Glu Trp
        1075                1080                1085

Thr Gly Leu Lys Val Ala Lys Arg Leu His Arg Ser Leu Leu Asn Arg
    1090                1095                1100
```

-continued

```
Ile Ile Leu Ala Pro Met Arg Phe Phe Glu Thr Thr Pro Leu Gly Ser
1105                1110                1115                1120

Ile Leu Asn Arg Phe Ser Ser Asp Cys Asn Thr Ile Asp Gln His Ile
            1125                1130                1135

Pro Ser Thr Leu Glu Cys Leu Ser Arg Ser Thr Leu Leu Cys Val Ser
                1140                1145                1150

Ala Leu Ala Val Ile Ser Tyr Val Thr Pro Val Phe Leu Val Ala Leu
                    1155                1160                1165

Leu Pro Leu Ala Val Val Cys Tyr Phe Ile Gln Lys Tyr Phe Arg Val
            1170                1175                1180

Ala Ser Arg Asp Leu Gln Gln Leu Asp Asp Thr Thr Gln Leu Pro Leu
1185                1190                1195                1200

Leu Ser His Phe Ala Glu Thr Val Glu Gly Leu Thr Thr Ile Arg Ala
                1205                1210                1215

Phe Arg Tyr Glu Ala Arg Phe Gln Gln Lys Leu Leu Glu Tyr Thr Asp
                1220                1225                1230

Ser Asn Asn Ile Ala Ser Leu Phe Leu Thr Ala Ala Asn Arg Trp Leu
            1235                1240                1245

Glu Val Arg Met Glu Tyr Ile Gly Ala Cys Val Val Leu Ile Ala Ala
1250                1255                1260

Ala Thr Ser Ile Ser Asn Ser Leu His Arg Glu Leu Ser Ala Gly Leu
1265                1270                1275                1280

Val Gly Leu Gly Leu Thr Tyr Ala Leu Met Val Ser Asn Tyr Leu Asn
                1285                1290                1295

Trp Met Val Arg Asn Leu Ala Asp Met Glu Ile Gln Leu Gly Ala Val
                1300                1305                1310

Lys Gly Ile His Thr Leu Leu Lys Thr Glu Ala Glu Ser Tyr Glu Gly
            1315                1320                1325

Leu Leu Ala Pro Ser Leu Ile Pro Lys Asn Trp Pro Asp Gln Gly Lys
            1330                1335                1340

Ile Gln Ile Gln Asn Leu Ser Val Arg Tyr Asp Ser Ser Leu Lys Pro
1345                1350                1355                1360

Val Leu Lys His Val Asn Ala Leu Ile Ser Pro Gly Gln Lys Ile Gly
                1365                1370                1375

Ile Cys Gly Arg Thr Gly Ser Gly Lys Ser Ser Phe Ser Leu Ala Phe
            1380                1385                1390

Phe Arg Met Val Asp Met Phe Glu Gly Arg Ile Ile Ile Asp Gly Ile
            1395                1400                1405

Asp Ile Ala Lys Leu Pro Leu His Thr Leu Gly Ser Arg Leu Ser Ile
1410                1415                1420

Ile Leu Gln Asp Pro Val Leu Phe Ser Gly Thr Ile Arg Phe Asn Leu
1425                1430                1435                1440

Asp Pro Glu Lys Lys Cys Ser Asp Ser Thr Leu Trp Glu Ala Leu Glu
            1445                1450                1455

Ile Ala Gln Leu Lys Leu Val Val Lys Ala Leu Pro Gly Gly Leu Asp
            1460                1465                1470

Ala Ile Ile Thr Glu Gly Gly Glu Asn Phe Ser Gln Gly Gln Arg Gln
            1475                1480                1485

Leu Phe Cys Leu Ala Arg Ala Phe Val Arg Lys Thr Ser Ile Phe Ile
            1490                1495                1500

Met Asp Glu Ala Thr Ala Ser Ile Asp Met Ala Thr Glu Asn Ile Leu
1505                1510                1515                1520
```

```
Gln Lys Val Val Met Thr Ala Phe Ala Asp Arg Thr Val Val Thr Ile
            1525                1530                1535

Ala His Arg Val His Thr Ile Leu Ser Ala Asp Leu Val Met Val Leu
        1540                1545                1550

Lys Arg Gly Ala Ile Leu Glu Phe Asp Lys Pro Glu Lys Leu Leu Ser
        1555                1560                1565

Gln Lys Asp Ser Val Phe Ala Ser Phe Val Arg Ala Asp
    1570                1575                1580

(2) INFORMATION FOR SEQ ID NO:7:

(i) SEQUENCE CHARACTERISTICS:
        (A) LENGTH: 4877 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:7:

AGCCGAGCCC GTGCGCGCGC CGCCATGCCC TTGGCCTTCT GCGGTACCGA GAACCACTCG      60

GCCGCCTACC GGGTGGACCA GGGCGTCCTC AACAACGGCT GCTTCGTGGA CGCGCTCAAC     120

GTGGTGCCGC ACGTTTTCCT GCTCTTCATC ACCTTCCCCA TCCTCTTCAT CGGATGGGGC     180

AGCCAGAGCT CCAAGGTGCA CATCCACCAC AGCACCTGGC TGCACTTTCC AGGGCACAAC     240

CTGCGCTGGA TCCTTACCTT CATTTTGCTC TTCGTCCTTG TGTGTGAGAT CGCTGAGGGC     300

ATCCTGTCTG ATGGGGTGAC AGAATCCCGC CACCTCCACC TGTACATGCC AGCCGGGATG     360

GCGTTCATGG CTGCCATCAC CTCTGTAGTC TACTATCATA ACATCGAGAC CTCCAACTTC     420

CCCAAGCTTT TGATCGCTCT GCTCATCTAT TGGACCCTGG CCTTCATCAC GAAGACCATC     480

AAGTTTGTCA AGTTCTATGA CCACGCCATC GGCTTCTCCC AGCTGCGCTT CTGCCTCACG     540

GGGCTTCTGG TGATCCTGTA TGGGATGTTG CTGCTTGTGG AGGTCAACGT CATCAGAGTG     600

AGGAGGTACA TCTTCTTCAA GACGCCACGG GAGGTGAAGC CCCCTGAGGA CCTGCAGGAC     660

CTGGGTGTGC GCTTTCTGCA GCCCTTCGTT AACCTGCTGT CAAAGGGGAC CTATTGGTGG     720

ATGAATGCCT TCATCAAGAC GGCCCACAAG AAGCCCATCG ACCTGCGGGC CATCGCGAAG     780

CTGCCCATCG CCATGAGAGC CCTCACCAAC TATCAGCGCC TCTGCGTGGC CTTCGATGCT     840

CAGGCGCGGA AGGACACACA GAGCCCACAG GGTGCCCGGG CCATCTGGAG GGCTCTATGC     900

CATGCCTTTG GGAGACGCCT GATCCTCAGC AGCACATTCC GCATCCTGGC TGACCTGTTG     960

GGCTTCGCTG GACCACTCTG CATCTTTGGG ATCGTGGACC ACCTGGGGAA GGAGAACCAC    1020

GTCTTCCAGC CCAAGACACA GTTTCTCGGG GTTTACTTCG TCTCTTCTCA AGAGTTCCTT    1080

GGCAATGCCT ACGTCTTGGC CGTGCTTCTG TTCCTTGCCC TGCTACTGCA AAGGACATTC    1140

CTGCAAGCCT CATACTACGT CGCCATTGAA ACTGGAATTA ACCTGAGAGG AGCAATCCAG    1200

ACCAAGATTT ACAATAAAAT CATGCACATG TCCACCTCCA ACCTGTCAAT GGGGGAAATG    1260

ACTGCTGGGC AGATCTGCAA CCTGGTGGCC ATCGACACAA ACCAGCTCAT GTGGTTCTTC    1320

TTTCTGTGCC CAAACCTCTG GACGATGCCA GTACAGATCA TTGTGGGCGT GATCCTTCTC    1380

TACTACATCC TTGGGGTCAG TGCCTTGATT GGAGCAGCTG TCATCATTCT GCTGGCTCCT    1440

GTACAGTACT TTGTGGCCAC CAAGCTCTCC CAGGCACAGC GGACGACCTT GGAGCACTCC    1500
```

```
AACGAGAGGC TGAAGCAGAC CAACGAGATG CTCCGGGCA TGAAGCTGCT CAAACTGTAT    1560

GCGTGGGAGA GCATCTTCTG CTCCAGGGTG GAGGTGACTC GCAGGAAGGA GATGACCAGC    1620

CTGAGGGCGT TGCTGTCTA CACTTCCATC TCCATCTTCA TGAACACAGC CATCCCCATT    1680

GCTGCCGTCC TCATCACCTT CGTGGGCCAC GTCAGCTTCT TCAAAGAGTC GGACTTGTCA    1740

CCCTCGGTGG CCTTTGCCTC CCTCTCTCTC TTCCACATCC TGGTCACTCC ACTGTTCCTG    1800

CTGTCTAGCG TGGTTCGGTC CACTGTCAAA GCCCTGGTGA GCGTGCAAAA ACTGAGCGAG    1860

TTCCTGTCTA GTGCAGAGAT CCGTGAGGAG CAGTGTGCCC CCCGAGAGCC TGCACCCCAA    1920

GGCCAAGCCG GCAAGTACCA GGCAGTGCCC CTCAAGGTTG TGAACCGCAA ACGCCCAGCC    1980

CGGGAAGAGG TCCGGGACCT CCTGGGCCCA CTGCAGAGGC TGGCCCCTAG CATGGACGGG    2040

GATGCTGACA ACTTCTGTGT CCAGATCATC GGAGGCTTCT TCACCTGGAC CCCTGATGGA    2100

ATCCCCACTC TGTCCAACAT CACCATCCGT ATTCCCGAG GTCAGCTAAC CATGATTGTG    2160

GGGCAGGTGG GCTGCGGCAA GTCCTCGCTC CTCCTCGCCA CCCTGGGGGA GATGCAGAAG    2220

GTGTCGGGGG CCGTCTTCTG GAACAGCAAC CTTCCGGACA GCGAGGGGAG AGGACCCCAG    2280

CAGCCCAGAG CGGGAGACAG CAGCTGGCTC GGATATCAGG AGCAGAGGCC CCGTGGCTAC    2340

GCATCTCAGA AACCATGGCT GCTAAACGCC ACCGTGGAAG AGAACATCAC CTTCGAGAGT    2400

CCCTTCAATC CGCAGCGGTA CAAGATGGTC ATCGAAGCCT GCTCCCTGCA GCCGGACATA    2460

GACATCCTGC CCCACGGAGA CCAGACTCAG ATTGGGGAAC GGGGCATCAA CCTGTCTGGT    2520

GGTCAGCGTC CAGATCAGTG TGGTCCAGAG CCCTCTACCA GCAGACCAAT GTTCGTCTTC    2580

TTGGATGACC CCTTCTCAGC TTTGGATGTC CATCTGAGTG ACCACCTGAT GCAGGCCGGC    2640

ATCCTTGAGC TGCTCCGGGA TGACAAGAGG ACAGTGGTCT TGGTGACCCA CAAGCTACAG    2700

TATCTGCCTC ATGCAGACTG GATCATTGCC ATGAAGGATG GGACCATTCA GAGGGAAGGG    2760

ACGCTCAAGG ACTTCCAGAG GTCCGAGTGC CAGCTCTTTG AGCACTGGAA GACCCTCATG    2820

AACCGGCAGG ACCAAGAGCT GGAGAAGGAG ACAGTCATGG AGAGGAAAGC CTCAGAGCCA    2880

TCTCAGGGCC TGCCCCGTGC CATGTCCTCC AGAGACGGCC TTCTGCTGGA TGAGGAAGAG    2940

GAGGAAGAGG AGGCAGCCGA AAGCGAGGAA GATGACAACT TATCTTCAGT GCTGCATCAG    3000

CGAGCTAAGA TCCCCTGGCG AGCCTGCACT AAGTATCTGT CCTCTGCTGG CATTCTGCTC    3060

CTGTCCCTGC TTGTCTTCTC CCAGCTGCTC AAGCACATGG TCTTGGTGGC CATTGATTAT    3120

TGGCTGGCCA AGTGGACGGA CAGTGCCCTG GTCCTGAGCC CCGCTGCCAG GAACTGTTCG    3180

CTCAGCCAGG AATGTGACCT GGACCAGTCT GTCTATGCCA TGGTATTCAC CTTGCTCTGC    3240

AGCCTGGGTA TCGTGCTGTG CCTGGTCACC TCTGTCACTG TGGAGTGGAC GGGACTGAAG    3300

GTGGCCAAGA GGCTACACCG CAGCCTGCTC AACCGCATCA TCCTGGCCCC CATGAGGTTC    3360

TTTGAGACCA CACCCCTCGG GAGTATCCTG AACAGATTTT CATCCGACTG TAACACCATT    3420

GACCAGCACA TCCCATCCAC GCTGGAGTGT CTGAGCCGGT CCACCCTGCT GTGTGTCTCC    3480

GCCCTGACTG TCATCTCCTA TGTCACACCC GTGTTCCTCG TGGCCCTCTT ACCCCTAGCT    3540

GTTGTGTGCT ACTTCATTCA GAAGTACTTC CGAGTGGCAT CCAGGGACCT GCAGCAGCTG    3600

GACGACACGA CGCAGCTCCC GCTCGTCTCA CACTTTGCTG AAACTGTGGA GGGACTCACC    3660

ACCATCCGTG CCTTCAGGTA CGAGGCCCGG TTCCAGCAGA AGCTTCTAGA ATATACCGAC    3720

TCCAACAACA TCGCCTCCCT CTTCCTCACG GCAGCCAACA GATGGCTGGA AGTCTGCATG    3780

GAGTACATCG GAGCGTGCGT GGTACTCATT GCGGCTGCCA CCTCCATCTC CAACTCCCTG    3840

CACAGGGAAC TTTCTGCTGG CCTGGTGGGC CTGGGCCTCA CCTATGCCTT GATGGTCTCC    3900
```

-continued

```
AACTACCTCA ACTGGATGGT GAGGAACCTG GCGGACATGG AGATCCAGCT GGGGGCTGTG      3960

AAGAGGATCC ACGCACTCCT GAAAACCGAG GCGGAGAGCT ATGAGGGGCT CCTGGCGCCG      4020

TCGTTGATCC CCAAGAACTG GCCAGACCAA GGGAAGATCC AAATTCAGAA CCTGAGCGTG      4080

CGCTATGACA GCTCCCTGAA GCCAGTGCTG AAGCATGTCA ACACCCTCAT CTCCCCGGGG      4140

CAGAAGATCG GGATCTGCGG CCGCACAGGC AGCGGGAAGT CCTCCTTCTC CCTGGCCTTT      4200

TTCCGAATGG TGGACATGTT TGAAGGACGC ATCATCATTG ATGGCATCGA CATCGCCAAG      4260

CTGCCACTTC ACACGCTGCG CTCACGCCTG TCCATCATCC TACAGGACCC CGTCCTCTTC      4320

AGCGGCACGA TCAGATTCAA CCTGGACCCC GAGAAGAAAT GCTCAGACAG CACACTGTGG      4380

GAGGCCCTGG AGATCGCCCA GCTGAAGCTG GTAGTGAAGG CACTGCCAGG AGGCCTAGAT      4440

GCCATCATCA CAGAAGGAGG GGAGAATTTT AGCCAGGGCC AGAGGCAGCT GTTCTGCCTG      4500

GCCCGGGCCT TCGTGAGGAA GACCAGCATC TTCATCATGG ATGAAGCAAC CGCCTCCATC      4560

GACATGGCTA CGGAGAACAT CCTCCAGAAG GTGGTGATGA CAGCCTTCGC AGACCGCACG      4620

GTGGTCACCA TCGCGCATCG TGTGCACACC ATCCTGAGTG CAGACCTGGT GATGGTCCTC      4680

AAGAGGGGTG CTATCCTGGA GTTTGACAAG CCAGAGACGC TCCTCAGCCA GAAGGACAGC      4740

GTGTTCGCCT CCTTTGTCCG TGCGGACAAG TGACTTACCG GAGCCAAAGT GCCACCCCGC      4800

GCCTCGCTTG CTTGCCTAGG ATTTCTAACT GCAAATCACT TGTAAATAAA TTAATTCTTT      4860

GCTAAAAAAA AAAAAAA                                                     4877
```

(2) INFORMATION FOR SEQ ID NO:8:

(i) SEQUENCE CHARACTERISTICS:
        (A) LENGTH: 4877 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 25..4770

(xi) SEQUENCE DESCRIPTION: SEQ ID NO:8:

```
AGCCGAGCCC GTGCGCGCGC CGCC ATG CCC TTG GCC TTC TGC GGT ACC GAG        51
                         Met Pro Leu Ala Phe Cys Gly Thr Glu
                          1               5

AAC CAC TCG GCC GCC TAC CGG GTG GAC CAG GGC GTC CTC AAC AAC GGC        99
Asn His Ser Ala Ala Tyr Arg Val Asp Gln Gly Val Leu Asn Asn Gly
 10              15                  20                  25

TGC TTC GTG GAC GCG CTC AAC GTG GTG CCG CAC GTT TTC CTG CTC TTC       147
Cys Phe Val Asp Ala Leu Asn Val Val Pro His Val Phe Leu Leu Phe
                 30                  35                  40

ATC ACC TTC CCC ATC CTC TTC ATC GGA TGG GGC AGC CAG AGC TCC AAG       195
Ile Thr Phe Pro Ile Leu Phe Ile Gly Trp Gly Ser Gln Ser Ser Lys
             45                  50                  55

GTG CAC ATC CAC CAC AGC ACC TGG CTG CAC TTT CCA GGG CAC AAC CTG       243
Val His Ile His His Ser Thr Trp Leu His Phe Pro Gly His Asn Leu
         60                  65                  70

CGC TGG ATC CTT ACC TTC ATT TTG CTC TTC GTC CTT GTG TGT GAG ATC       291
Arg Trp Ile Leu Thr Phe Ile Leu Leu Phe Val Leu Val Cys Glu Ile
     75                  80                  85
```

```
GCT GAG GGC ATC CTG TCT GAT GGG GTG ACA GAA TCC CGC CAC CTC CAC        339
Ala Glu Gly Ile Leu Ser Asp Gly Val Thr Glu Ser Arg His Leu His
 90              95                 100                 105

CTG TAC ATG CCA GCC GGG ATG GCG TTC ATG GCT GCC ATC ACC TCT GTA        387
Leu Tyr Met Pro Ala Gly Met Ala Phe Met Ala Ala Ile Thr Ser Val
            110                 115                 120

GTC TAC TAT CAT AAC ATC GAG ACC TCC AAC TTC CCC AAG CTT TTG ATC        435
Val Tyr Tyr His Asn Ile Glu Thr Ser Asn Phe Pro Lys Leu Leu Ile
                125                 130                 135

GCT CTG CTC ATC TAT TGG ACC CTG GCC TTC ATC ACG AAG ACC ATC AAG        483
Ala Leu Leu Ile Tyr Trp Thr Leu Ala Phe Ile Thr Lys Thr Ile Lys
            140                 145                 150

TTT GTC AAG TTC TAT GAC CAC GCC ATC GGC TTC TCC CAG CTG CGC TTC        531
Phe Val Lys Phe Tyr Asp His Ala Ile Gly Phe Ser Gln Leu Arg Phe
155                 160                 165

TGC CTC ACG GGG CTT CTG GTG ATC CTG TAT GGG ATG TTG CTG CTT GTG        579
Cys Leu Thr Gly Leu Leu Val Ile Leu Tyr Gly Met Leu Leu Leu Val
170                 175                 180                 185

GAG GTC AAC GTC ATC AGA GTG AGG AGG TAC ATC TTC TTC AAG ACG CCA        627
Glu Val Asn Val Ile Arg Val Arg Arg Tyr Ile Phe Phe Lys Thr Pro
                190                 195                 200

CGG GAG GTG AAG CCC CCT GAG GAC CTG CAG GAC CTG GGT GTG CGC TTT        675
Arg Glu Val Lys Pro Pro Glu Asp Leu Gln Asp Leu Gly Val Arg Phe
            205                 210                 215

CTG CAG CCC TTC GTT AAC CTG CTG TCA AAG GGG ACC TAT TGG TGG ATG        723
Leu Gln Pro Phe Val Asn Leu Leu Ser Lys Gly Thr Tyr Trp Trp Met
            220                 225                 230

AAT GCC TTC ATC AAG ACG GCC CAC AAG AAG CCC ATC GAC CTG CGG GCC        771
Asn Ala Phe Ile Lys Thr Ala His Lys Lys Pro Ile Asp Leu Arg Ala
235                 240                 245

ATC GCG AAG CTG CCC ATC GCC ATG AGA GCC CTC ACC AAC TAT CAG CGC        819
Ile Ala Lys Leu Pro Ile Ala Met Arg Ala Leu Thr Asn Tyr Gln Arg
250                 255                 260                 265

CTC TGC GTG GCC TTC GAT GCT CAG GCG CGG AAG GAC ACA CAG AGC CCA        867
Leu Cys Val Ala Phe Asp Ala Gln Ala Arg Lys Asp Thr Gln Ser Pro
                270                 275                 280

CAG GGT GCC CGG GCC ATC TGG AGG GCT CTA TGC CAT GCC TTT GGG AGA        915
Gln Gly Ala Arg Ala Ile Trp Arg Ala Leu Cys His Ala Phe Gly Arg
            285                 290                 295

CGC CTG ATC CTC AGC AGC ACA TTC CGC ATC CTG GCT GAC CTG TTG GGC        963
Arg Leu Ile Leu Ser Ser Thr Phe Arg Ile Leu Ala Asp Leu Leu Gly
            300                 305                 310

TTC GCT GGA CCA CTC TGC ATC TTT GGG ATC GTG GAC CAC CTG GGG AAG       1011
Phe Ala Gly Pro Leu Cys Ile Phe Gly Ile Val Asp His Leu Gly Lys
315                 320                 325

GAG AAC CAC GTC TTC CAG CCC AAG ACA CAG TTT CTC GGG GTT TAC TTC       1059
Glu Asn His Val Phe Gln Pro Lys Thr Gln Phe Leu Gly Val Tyr Phe
330                 335                 340                 345

GTC TCT TCT CAA GAG TTC CTT GGC AAT GCC TAC GTC TTG GCC GTG CTT       1107
Val Ser Ser Gln Glu Phe Leu Gly Asn Ala Tyr Val Leu Ala Val Leu
                350                 355                 360

CTG TTC CTT GCC CTG CTA CTG CAA AGG ACA TTC CTG CAA GCC TCA TAC       1155
Leu Phe Leu Ala Leu Leu Leu Gln Arg Thr Phe Leu Gln Ala Ser Tyr
            365                 370                 375

TAC GTC GCC ATT GAA ACT GGA ATT AAC CTG AGA GGA GCA ATC CAG ACC       1203
Tyr Val Ala Ile Glu Thr Gly Ile Asn Leu Arg Gly Ala Ile Gln Thr
            380                 385                 390

AAG ATT TAC AAT AAA ATC ATG CAC ATG TCC ACC TCC AAC CTG TCA ATG       1251
Lys Ile Tyr Asn Lys Ile Met His Met Ser Thr Ser Asn Leu Ser Met
```

```
                 395                 400                 405
GGG GAA ATG ACT GCT GGG CAG ATC TGC AAC CTG GTG GCC ATC GAC ACA        1299
Gly Glu Met Thr Ala Gly Gln Ile Cys Asn Leu Val Ala Ile Asp Thr
410                 415                 420                 425

AAC CAG CTC ATG TGG TTC TTC TTT CTG TGC CCA AAC CTC TGG ACG ATG        1347
Asn Gln Leu Met Trp Phe Phe Phe Leu Cys Pro Asn Leu Trp Thr Met
                430                 435                 440

CCA GTA CAG ATC ATT GTG GGC GTG ATC CTT CTC TAC TAC ATC CTT GGG        1395
Pro Val Gln Ile Ile Val Gly Val Ile Leu Leu Tyr Tyr Ile Leu Gly
            445                 450                 455

GTC AGT GCC TTG ATT GGA GCA GCT GTC ATC ATT CTG CTG GCT CCT GTA        1443
Val Ser Ala Leu Ile Gly Ala Ala Val Ile Ile Leu Leu Ala Pro Val
        460                 465                 470

CAG TAC TTT GTG GCC ACC AAG CTC TCC CAG GCA CAG CGG ACG ACC TTG        1491
Gln Tyr Phe Val Ala Thr Lys Leu Ser Gln Ala Gln Arg Thr Thr Leu
    475                 480                 485

GAG CAC TCC AAC GAG AGG CTG AAG CAG ACC AAC GAG ATG CTC CGG GGC        1539
Glu His Ser Asn Glu Arg Leu Lys Gln Thr Asn Glu Met Leu Arg Gly
490                 495                 500                 505

ATG AAG CTG CTC AAA CTG TAT GCG TGG GAG AGC ATC TTC TGC TCC AGG        1587
Met Lys Leu Leu Lys Leu Tyr Ala Trp Glu Ser Ile Phe Cys Ser Arg
                510                 515                 520

GTG GAG GTG ACT CGC AGG AAG GAG ATG ACC AGC CTG AGG GCG TTT GCT        1635
Val Glu Val Thr Arg Arg Lys Glu Met Thr Ser Leu Arg Ala Phe Ala
            525                 530                 535

GTC TAC ACT TCC ATC TCC ATC TTC ATG AAC ACA GCC ATC CCC ATT GCT        1683
Val Tyr Thr Ser Ile Ser Ile Phe Met Asn Thr Ala Ile Pro Ile Ala
        540                 545                 550

GCC GTC CTC ATC ACC TTC GTG GGC CAC GTC AGC TTC TTC AAA GAG TCG        1731
Ala Val Leu Ile Thr Phe Val Gly His Val Ser Phe Phe Lys Glu Ser
    555                 560                 565

GAC TTG TCA CCC TCG GTG GCC TTT GCC TCC CTC TCT CTC TTC CAC ATC        1779
Asp Leu Ser Pro Ser Val Ala Phe Ala Ser Leu Ser Leu Phe His Ile
570                 575                 580                 585

CTG GTC ACT CCA CTG TTC CTG CTG TCT AGC GTG GTT CGG TCC ACT GTC        1827
Leu Val Thr Pro Leu Phe Leu Leu Ser Ser Val Val Arg Ser Thr Val
                590                 595                 600

AAA GCC CTG GTG AGC GTG CAA AAA CTG AGC GAG TTC CTG TCT AGT GCA        1875
Lys Ala Leu Val Ser Val Gln Lys Leu Ser Glu Phe Leu Ser Ser Ala
            605                 610                 615

GAG ATC CGT GAG GAG CAG TGT GCC CCC CGA GAG CCT GCA CCC CAA GGC        1923
Glu Ile Arg Glu Glu Gln Cys Ala Pro Arg Glu Pro Ala Pro Gln Gly
        620                 625                 630

CAA GCC GGC AAG TAC CAG GCA GTG CCC CTC AAG GTT GTG AAC CGC AAA        1971
Gln Ala Gly Lys Tyr Gln Ala Val Pro Leu Lys Val Val Asn Arg Lys
    635                 640                 645

CGC CCA GCC CGG GAA GAG GTC CGG GAC CTC CTG GGC CCA CTG CAG AGG        2019
Arg Pro Ala Arg Glu Glu Val Arg Asp Leu Leu Gly Pro Leu Gln Arg
650                 655                 660                 665

CTG GCC CCT AGC ATG GAC GGG GAT GCT GAC AAC TTC TGT GTC CAG ATC        2067
Leu Ala Pro Ser Met Asp Gly Asp Ala Asp Asn Phe Cys Val Gln Ile
                670                 675                 680

ATC GGA GGC TTC TTC ACC TGG ACC CCT GAT GGA ATC CCC ACT CTG TCC        2115
Ile Gly Gly Phe Phe Thr Trp Thr Pro Asp Gly Ile Pro Thr Leu Ser
            685                 690                 695

AAC ATC ACC ATC CGT ATT CCC CGA GGT CAG CTA ACC ATG ATT GTG GGG        2163
Asn Ile Thr Ile Arg Ile Pro Arg Gly Gln Leu Thr Met Ile Val Gly
        700                 705                 710

CAG GTG GGC TGC GGC AAG TCC TCG CTC CTC CTC GCC ACC CTG GGG GAG        2211
```

```
Gln Val Gly Cys Gly Lys Ser Ser Leu Leu Ala Thr Leu Gly Glu
    715                 720                 725

ATG CAG AAG GTG TCG GGG GCC GTC TTC TGG AAC AGC AAC CTT CCG GAC        2259
Met Gln Lys Val Ser Gly Ala Val Phe Trp Asn Ser Asn Leu Pro Asp
730                 735                 740                 745

AGC GAG GGG AGA GGA CCC CAG CAG CCC AGA GCG GGA GAC AGC AGC TGG        2307
Ser Glu Gly Arg Gly Pro Gln Gln Pro Arg Ala Gly Asp Ser Ser Trp
                750                 755                 760

CTC GGA TAT CAG GAG CAG AGG CCC CGT GGC TAC GCA TCT CAG AAA CCA        2355
Leu Gly Tyr Gln Glu Gln Arg Pro Arg Gly Tyr Ala Ser Gln Lys Pro
            765                 770                 775

TGG CTG CTA AAC GCC ACC GTG GAA GAG AAC ATC ACC TTC GAG AGT CCC        2403
Trp Leu Leu Asn Ala Thr Val Glu Glu Asn Ile Thr Phe Glu Ser Pro
        780                 785                 790

TTC AAT CCG CAG CGG TAC AAG ATG GTC ATC GAA GCC TGC TCC CTG CAG        2451
Phe Asn Pro Gln Arg Tyr Lys Met Val Ile Glu Ala Cys Ser Leu Gln
    795                 800                 805

CCG GAC ATA GAC ATC CTG CCC CAC GGA GAC CAG ACT CAG ATT GGG AA         2499
Pro Asp Ile Asp Ile Leu Pro His Gly Asp Gln Thr Gln Ile Gly Glu
810                 815                 820                 825

CGG GGC ATC AAC CTG TCT GGT GGT CAG CGT CCA GAT CAG TGT GGT CCA        2547
Arg Gly Ile Asn Leu Ser Gly Gly Gln Arg Pro Asp Gln Cys Gly Pro
                830                 835                 840

GAG CCC TCT ACC AGC AGA CCA ATG TTC GTC TTC TTG GAT GAC CCC TTC        2595
Glu Pro Ser Thr Ser Arg Pro Met Phe Val Phe Leu Asp Asp Pro Phe
            845                 850                 855

TCA GCT TTG GAT GTC CAT CTG AGT GAC CAC CTG ATG CAG GCC GGC ATC        2643
Ser Ala Leu Asp Val His Leu Ser Asp His Leu Met Gln Ala Gly Ile
        860                 865                 870

CTT GAG CTG CTC CGG GAT GAC AAG AGG ACA GTG GTC TTG GTG ACC CAC        2691
Leu Glu Leu Leu Arg Asp Asp Lys Arg Thr Val Val Leu Val Thr His
    875                 880                 885

AAG CTA CAG TAT CTG CCT CAT GCA GAC TGG ATC ATT GCC ATG AAG GAT        2739
Lys Leu Gln Tyr Leu Pro His Ala Asp Trp Ile Ile Ala Met Lys Asp
890                 895                 900                 905

GGG ACC ATT CAG AGG GAA GGG ACG CTC AAG GAC TTC CAG AGG TCC GAG        2787
Gly Thr Ile Gln Arg Glu Gly Thr Leu Lys Asp Phe Gln Arg Ser Glu
                910                 915                 920

TGC CAG CTC TTT GAG CAC TGG AAG ACC CTC ATG AAC CGG CAG GAC CAA        2835
Cys Gln Leu Phe Glu His Trp Lys Thr Leu Met Asn Arg Gln Asp Gln
            925                 930                 935

GAG CTG GAG AAG GAG ACA GTC ATG GAG AGG AAA GCC TCA GAG CCA TCT        2883
Glu Leu Glu Lys Glu Thr Val Met Glu Arg Lys Ala Ser Glu Pro Ser
        940                 945                 950

CAG GGC CTG CCC CGT GCC ATG TCC TCC AGA GAC GGC CTT CTG CTG GAT        2931
Gln Gly Leu Pro Arg Ala Met Ser Ser Arg Asp Gly Leu Leu Leu Asp
    955                 960                 965

GAG GAA GAG GAG GAA GAG GAG GCA GCC GAA AGC GAG GAA GAT GAC AAC        2979
Glu Glu Glu Glu Glu Glu Glu Ala Ala Glu Ser Glu Glu Asp Asp Asn
970                 975                 980                 985

TTA TCT TCA GTG CTG CAT CAG CGA GCT AAG ATC CCC TGG CGA GCC TGC        3027
Leu Ser Ser Val Leu His Gln Arg Ala Lys Ile Pro Trp Arg Ala Cys
                990                 995                 1000

ACT AAG TAT CTG TCC TCT GCT GGC ATT CTG CTC CTG TCC CTG CTT GTC        3075
Thr Lys Tyr Leu Ser Ser Ala Gly Ile Leu Leu Leu Ser Leu Leu Val
            1005                1010                1015

TTC TCC CAG CTG CTC AAG CAC ATG GTC TTG GTG GCC ATT GAT TAT TGG        3123
Phe Ser Gln Leu Leu Lys His Met Val Leu Val Ala Ile Asp Tyr Trp
        1020                1025                1030
```

```
CTG GCC AAG TGG ACG GAC AGT GCC CTG GTC CTG AGC CCC GCT GCC AGG        3171
Leu Ala Lys Trp Thr Asp Ser Ala Leu Val Leu Ser Pro Ala Ala Arg
        1035            1040            1045

AAC TGT TCG CTC AGC CAG GAA TGT GAC CTG GAC CAG TCT GTC TAT GCC        3219
Asn Cys Ser Leu Ser Gln Glu Cys Asp Leu Asp Gln Ser Val Tyr Ala
1050            1055            1060            1065

ATG GTA TTC ACC TTG CTC TGC AGC CTG GGT ATC GTG CTG TGC CTG GTC        3267
Met Val Phe Thr Leu Leu Cys Ser Leu Gly Ile Val Leu Cys Leu Val
        1070            1075            1080

ACC TCT GTC ACT GTG GAG TGG ACG GGA CTG AAG GTG GCC AAG AGG CTA        3315
Thr Ser Val Thr Val Glu Trp Thr Gly Leu Lys Val Ala Lys Arg Leu
            1085            1090            1095

CAC CGC AGC CTG CTC AAC CGC ATC ATC CTG GCC CCC ATG AGG TTC TTT        3363
His Arg Ser Leu Leu Asn Arg Ile Ile Leu Ala Pro Met Arg Phe Phe
        1100            1105            1110

GAG ACC ACA CCC CTC GGG AGT ATC CTG AAC AGA TTT TCA TCC GAC TGT        3411
Glu Thr Thr Pro Leu Gly Ser Ile Leu Asn Arg Phe Ser Ser Asp Cys
        1115            1120            1125

AAC ACC ATT GAC CAG CAC ATC CCA TCC ACG CTG GAG TGT CTG AGC CGG        3459
Asn Thr Ile Asp Gln His Ile Pro Ser Thr Leu Glu Cys Leu Ser Arg
1130            1135            1140            1145

TCC ACC CTG CTG TGT GTC TCC GCC CTG ACT GTC ATC TCC TAT GTC ACA        3507
Ser Thr Leu Leu Cys Val Ser Ala Leu Thr Val Ile Ser Tyr Val Thr
            1150            1155            1160

CCC GTG TTC CTC GTG GCC CTC TTA CCC CTA GCT GTT GTG TGC TAC TTC        3555
Pro Val Phe Leu Val Ala Leu Leu Pro Leu Ala Val Val Cys Tyr Phe
        1165            1170            1175

ATT CAG AAG TAC TTC CGA GTG GCA TCC AGG GAC CTG CAG CAG CTG GAC        3603
Ile Gln Lys Tyr Phe Arg Val Ala Ser Arg Asp Leu Gln Gln Leu Asp
        1180            1185            1190

GAC ACG ACG CAG CTC CCG CTC GTC TCA CAC TTT GCT GAA ACT GTG GAG        3651
Asp Thr Thr Gln Leu Pro Leu Val Ser His Phe Ala Glu Thr Val Glu
        1195            1200            1205

GGA CTC ACC ACC ATC CGT GCC TTC AGG TAC GAG GCC CGG TTC CAG CAG        3699
Gly Leu Thr Thr Ile Arg Ala Phe Arg Tyr Glu Ala Arg Phe Gln Gln
1210            1215            1220            1225

AAG CTT CTA GAA TAT ACC GAC TCC AAC AAC ATC GCC TCC CTC TTC CTC        3747
Lys Leu Leu Glu Tyr Thr Asp Ser Asn Asn Ile Ala Ser Leu Phe Leu
        1230            1235            1240

ACG GCA GCC AAC AGA TGG CTG GAA GTC TGC ATG GAG TAC ATC GGA GCG        3795
Thr Ala Ala Asn Arg Trp Leu Glu Val Cys Met Glu Tyr Ile Gly Ala
        1245            1250            1255

TGC GTG GTA CTC ATT GCG GCT GCC ACC TCC ATC TCC AAC TCC CTG CAC        3843
Cys Val Val Leu Ile Ala Ala Ala Thr Ser Ile Ser Asn Ser Leu His
        1260            1265            1270

AGG GAA CTT TCT GCT GGC CTG GTG GGC CTG GGC CTC ACC TAT GCC TTG        3891
Arg Glu Leu Ser Ala Gly Leu Val Gly Leu Gly Leu Thr Tyr Ala Leu
    1275            1280            1285

ATG GTC TCC AAC TAC CTC AAC TGG ATG GTG AGG AAC CTG GCG GAC ATG        3939
Met Val Ser Asn Tyr Leu Asn Trp Met Val Arg Asn Leu Ala Asp Met
1290            1295            1300            1305

GAG ATC CAG CTG GGG GCT GTG AAG AGG ATC CAC GCA CTC CTG AAA ACC        3987
Glu Ile Gln Leu Gly Ala Val Lys Arg Ile His Ala Leu Leu Lys Thr
        1310            1315            1320

GAG GCG GAG AGC TAT GAG GGG CTC CTG GCG CCG TCG TTG ATC CCC AAG        4035
Glu Ala Glu Ser Tyr Glu Gly Leu Leu Ala Pro Ser Leu Ile Pro Lys
        1325            1330            1335

AAC TGG CCA GAC CAA GGG AAG ATC CAA ATT CAG AAC CTG AGC GTG CGC        4083
Asn Trp Pro Asp Gln Gly Lys Ile Gln Ile Gln Asn Leu Ser Val Arg
        1340            1345            1350
```

-continued

```
TAT GAC AGC TCC CTG AAG CCA GTG CTG AAG CAT GTC AAC ACC CTC ATC      4131
Tyr Asp Ser Ser Leu Lys Pro Val Leu Lys His Val Asn Thr Leu Ile
        1355                1360                1365

TCC CCG GGG CAG AAG ATC GGG ATC TGC GGC CGC ACA GGC AGC GGG AAG      4179
Ser Pro Gly Gln Lys Ile Gly Ile Cys Gly Arg Thr Gly Ser Gly Lys
1370                1375                1380                1385

TCC TCC TTC TCC CTG GCC TTT TTC CGA ATG GTG GAC ATG TTT GAA GGA      4227
Ser Ser Phe Ser Leu Ala Phe Phe Arg Met Val Asp Met Phe Glu Gly
                1390                1395                1400

CGC ATC ATC ATT GAT GGC ATC GAC ATC GCC AAG CTG CCA CTT CAC ACG      4275
Arg Ile Ile Ile Asp Gly Ile Asp Ile Ala Lys Leu Pro Leu His Thr
            1405                1410                1415

CTG CGC TCA CGC CTG TCC ATC ATC CTA CAG GAC CCC GTC CTC TTC AGC      4323
Leu Arg Ser Arg Leu Ser Ile Ile Leu Gln Asp Pro Val Leu Phe Ser
        1420                1425                1430

GGC ACG ATC AGA TTC AAC CTG GAC CCC GAG AAG AAA TGC TCA GAC AGC      4371
Gly Thr Ile Arg Phe Asn Leu Asp Pro Glu Lys Lys Cys Ser Asp Ser
    1435                1440                1445

ACA CTG TGG GAG GCC CTG GAG ATC GCC CAG CTG AAG CTG GTA GTG AAG      4419
Thr Leu Trp Glu Ala Leu Glu Ile Ala Gln Leu Lys Leu Val Val Lys
1450                1455                1460                1465

GCA CTG CCA GGA GGC CTA GAT GCC ATC ATC ACA GAA GGA GGG GAG AAT      4467
Ala Leu Pro Gly Gly Leu Asp Ala Ile Ile Thr Glu Gly Gly Glu Asn
                1470                1475                1480

TTT AGC CAG GGC CAG AGG CAG CTG TTC TGC CTG GCC CGG GCC TTC GTG      4515
Phe Ser Gln Gly Gln Arg Gln Leu Phe Cys Leu Ala Arg Ala Phe Val
            1485                1490                1495

AGG AAG ACC AGC ATC TTC ATC ATG GAT GAA GCA ACC GCC TCC ATC GAC      4563
Arg Lys Thr Ser Ile Phe Ile Met Asp Glu Ala Thr Ala Ser Ile Asp
        1500                1505                1510

ATG GCT ACG GAG AAC ATC CTC CAG AAG GTG GTG ATG ACA GCC TTC GCA      4611
Met Ala Thr Glu Asn Ile Leu Gln Lys Val Val Met Thr Ala Phe Ala
    1515                1520                1525

GAC CGC ACG GTG GTC ACC ATC GCG CAT CGT GTG CAC ACC ATC CTG AGT      4659
Asp Arg Thr Val Val Thr Ile Ala His Arg Val His Thr Ile Leu Ser
1530                1535                1540                1545

GCA GAC CTG GTG ATG GTC CTC AAG AGG GGT GCT ATC CTG GAG TTT GAC      4707
Ala Asp Leu Val Met Val Leu Lys Arg Gly Ala Ile Leu Glu Phe Asp
                1550                1555                1560

AAG CCA GAG ACG CTC CTC AGC CAG AAG GAC AGC GTG TTC GCC TCC TTT      4755
Lys Pro Glu Thr Leu Leu Ser Gln Lys Asp Ser Val Phe Ala Ser Phe
            1565                1570                1575

GTC CGT GCG GAC AAG TGACTTACCG GAGCCAAAGT GCCACCCCGC GCCTCGCTTG      4810
Val Arg Ala Asp Lys
        1580

CTTGCCTAGG ATTTCTAACT GCAAATCACT TGTAAATAAA TTAATTCTTT GCTAAAAAAA   4870

AAAAAAA                                                              4877
```

(2) INFORMATION FOR SEQ ID NO:9:

(i) SEQUENCE CHARACTERISTICS:
        (A) LENGTH: 1582 amino acids
        (B) TYPE: amino acid
        (D) TOPOLOGY: linear (ii) MOLECULE TYPE: protein (xi) SEQUENCE DESCRIPTION: SEQ ID NO:9:

```
Met Pro Leu Ala Phe Cys Gly Thr Glu Asn His Ser Ala Ala Tyr Arg
1               5                   10                  15
```

-continued

```
Val Asp Gln Gly Val Leu Asn Asn Gly Cys Phe Val Asp Ala Leu Asn
             20                  25                  30

Val Val Pro His Val Phe Leu Leu Phe Ile Thr Phe Pro Ile Leu Phe
         35                  40                  45

Ile Gly Trp Gly Ser Gln Ser Ser Lys Val His Ile His His Ser Thr
     50                  55                  60

Trp Leu His Phe Pro Gly His Asn Leu Arg Trp Ile Leu Thr Phe Ile
 65              70                  75                      80

Leu Leu Phe Val Leu Val Cys Glu Ile Ala Glu Gly Ile Leu Ser Asp
                 85                  90                  95

Gly Val Thr Glu Ser Arg His Leu His Leu Tyr Met Pro Ala Gly Met
            100                 105                 110

Ala Phe Met Ala Ala Ile Thr Ser Val Val Tyr Tyr His Asn Ile Glu
        115                 120                 125

Thr Ser Asn Phe Pro Lys Leu Leu Ile Ala Leu Leu Ile Tyr Trp Thr
        130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Leu Val Glu Val Asn Val Ile Arg Val
            180                 185                 190

Arg Arg Tyr Ile Phe Phe Lys Thr Pro Arg Glu Val Lys Pro Pro Glu
        195                 200                 205

Asp Leu Gln Asp Leu Gly Val Arg Phe Leu Gln Pro Phe Val Asn Leu
        210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Ala Lys Leu Pro Ile Ala
                245                 250                 255

Met Arg Ala Leu Thr Asn Tyr Gln Arg Leu Cys Val Ala Phe Asp Ala
            260                 265                 270

Gln Ala Arg Lys Asp Thr Gln Ser Pro Gln Gly Ala Arg Ala Ile Trp
        275                 280                 285

Arg Ala Leu Cys His Ala Phe Gly Arg Arg Leu Ile Leu Ser Ser Thr
        290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

Gly Asn Ala Tyr Val Leu Ala Val Leu Leu Phe Leu Ala Leu Leu Leu
        355                 360                 365

Gln Arg Thr Phe Leu Gln Ala Ser Tyr Tyr Val Ala Ile Glu Thr Gly
        370                 375                 380

Ile Asn Leu Arg Gly Ala Ile Gln Thr Lys Ile Tyr Asn Lys Ile Met
385                 390                 395                 400

His Met Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
            420                 425                 430
```

-continued

```
Phe Leu Cys Pro Asn Leu Trp Thr Met Pro Val Gln Ile Ile Val Gly
            435                 440                 445

Val Ile Leu Leu Tyr Tyr Ile Leu Gly Val Ser Ala Leu Ile Gly Ala
        450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu His Ser Asn Glu Arg Leu
                485                 490                 495

Lys Gln Thr Asn Glu Met Leu Arg Gly Met Lys Leu Leu Lys Leu Tyr
            500                 505                 510

Ala Trp Glu Ser Ile Phe Cys Ser Arg Val Glu Val Thr Arg Arg Lys
        515                 520                 525

Glu Met Thr Ser Leu Arg Ala Phe Ala Val Tyr Thr Ser Ile Ser Ile
            530                 535                 540

Phe Met Asn Thr Ala Ile Pro Ile Ala Ala Val Leu Ile Thr Phe Val
545                 550                 555                 560

Gly His Val Ser Phe Phe Lys Glu Ser Asp Leu Ser Pro Ser Val Ala
                565                 570                 575

Phe Ala Ser Leu Ser Leu Phe His Ile Leu Val Thr Pro Leu Phe Leu
            580                 585                 590

Leu Ser Ser Val Val Arg Ser Thr Val Lys Ala Leu Val Ser Val Gln
        595                 600                 605

Lys Leu Ser Glu Phe Leu Ser Ser Ala Glu Ile Arg Glu Glu Gln Cys
610                 615                 620

Ala Pro Arg Glu Pro Ala Pro Gln Gly Gln Ala Gly Lys Tyr Gln Ala
625                 630                 635                 640

Val Pro Leu Lys Val Val Asn Arg Lys Arg Pro Ala Arg Glu Glu Val
                645                 650                 655

Arg Asp Leu Leu Gly Pro Leu Gln Arg Leu Ala Pro Ser Met Asp Gly
            660                 665                 670

Asp Ala Asp Asn Phe Cys Val Gln Ile Ile Gly Gly Phe Phe Thr Trp
        675                 680                 685

Thr Pro Asp Gly Ile Pro Thr Leu Ser Asn Ile Thr Ile Arg Ile Pro
690                 695                 700

Arg Gly Gln Leu Thr Met Ile Val Gly Gln Val Gly Cys Gly Lys Ser
705                 710                 715                 720

Ser Leu Leu Leu Ala Thr Leu Gly Glu Met Gln Lys Val Ser Gly Ala
                725                 730                 735

Val Phe Trp Asn Ser Asn Leu Pro Asp Ser Glu Gly Arg Gly Pro Gln
            740                 745                 750

Gln Pro Arg Ala Gly Asp Ser Ser Trp Leu Gly Tyr Gln Glu Gln Arg
        755                 760                 765

Pro Arg Gly Tyr Ala Ser Gln Lys Pro Trp Leu Leu Asn Ala Thr Val
770                 775                 780

Glu Glu Asn Ile Thr Phe Glu Ser Pro Phe Asn Pro Gln Arg Tyr Lys
785                 790                 795                 800

Met Val Ile Glu Ala Cys Ser Leu Gln Pro Asp Ile Asp Ile Leu Pro
                805                 810                 815

His Gly Asp Gln Thr Gln Ile Gly Glu Arg Gly Ile Asn Leu Ser Gly
            820                 825                 830

Gly Gln Arg Pro Asp Gln Cys Gly Pro Glu Pro Ser Thr Ser Arg Pro
        835                 840                 845

Met Phe Val Phe Leu Asp Asp Pro Phe Ser Ala Leu Asp Val His Leu
```

```
          850                 855                 860
Ser Asp His Leu Met Gln Ala Gly Ile Leu Glu Leu Leu Arg Asp Asp
865                 870                 875                 880

Lys Arg Thr Val Val Leu Val Thr His Lys Leu Gln Tyr Leu Pro His
                885                 890                 895

Ala Asp Trp Ile Ile Ala Met Lys Asp Gly Thr Ile Gln Arg Glu Gly
            900                 905                 910

Thr Leu Lys Asp Phe Gln Arg Ser Glu Cys Gln Leu Phe Glu His Trp
        915                 920                 925

Lys Thr Leu Met Asn Arg Gln Asp Gln Glu Leu Glu Lys Glu Thr Val
    930                 935                 940

Met Glu Arg Lys Ala Ser Glu Pro Ser Gln Gly Leu Pro Arg Ala Met
945                 950                 955                 960

Ser Ser Arg Asp Gly Leu Leu Leu Asp Glu Glu Glu Glu Glu Glu Glu
                965                 970                 975

Ala Ala Glu Ser Glu Glu Asp Asp Asn Leu Ser Ser Val Leu His Gln
            980                 985                 990

Arg Ala Lys Ile Pro Trp Arg Ala Cys Thr Lys Tyr Leu Ser Ser Ala
        995                 1000                1005

Gly Ile Leu Leu Leu Ser Leu Leu Val Phe Ser Gln Leu Leu Lys His
    1010                1015                1020

Met Val Leu Val Ala Ile Asp Tyr Trp Leu Ala Lys Trp Thr Asp Ser
1025                1030                1035                1040

Ala Leu Val Leu Ser Pro Ala Ala Arg Asn Cys Ser Leu Ser Gln Glu
                1045                1050                1055

Cys Asp Leu Asp Gln Ser Val Tyr Ala Met Val Phe Thr Leu Leu Cys
            1060                1065                1070

Ser Leu Gly Ile Val Leu Cys Leu Val Thr Ser Val Thr Val Glu Trp
        1075                1080                1085

Thr Gly Leu Lys Val Ala Lys Arg Leu His Arg Ser Leu Leu Asn Arg
    1090                1095                1100

Ile Ile Leu Ala Pro Met Arg Phe Phe Glu Thr Thr Pro Leu Gly Ser
1105                1110                1115                1120

Ile Leu Asn Arg Phe Ser Ser Asp Cys Asn Thr Ile Asp Gln His Ile
                1125                1130                1135

Pro Ser Thr Leu Glu Cys Leu Ser Arg Ser Thr Leu Leu Cys Val Ser
            1140                1145                1150

Ala Leu Thr Val Ile Ser Tyr Val Thr Pro Val Phe Leu Val Ala Leu
        1155                1160                1165

Leu Pro Leu Ala Val Val Cys Tyr Phe Ile Gln Lys Tyr Phe Arg Val
    1170                1175                1180

Ala Ser Arg Asp Leu Gln Gln Leu Asp Asp Thr Thr Gln Leu Pro Leu
1185                1190                1195                1200

Val Ser His Phe Ala Glu Thr Val Glu Gly Leu Thr Thr Ile Arg Ala
                1205                1210                1215

Phe Arg Tyr Glu Ala Arg Phe Gln Gln Lys Leu Leu Glu Tyr Thr Asp
            1220                1225                1230

Ser Asn Asn Ile Ala Ser Leu Phe Leu Thr Ala Ala Asn Arg Trp Leu
        1235                1240                1245

Glu Val Cys Met Glu Tyr Ile Gly Ala Cys Val Val Leu Ile Ala Ala
    1250                1255                1260

Ala Thr Ser Ile Ser Asn Ser Leu His Arg Glu Leu Ser Ala Gly Leu
1265                1270                1275                1280
```

-continued

```
Val Gly Leu Gly Leu Thr Tyr Ala Leu Met Val Ser Asn Tyr Leu Asn
            1285                1290                1295

Trp Met Val Arg Asn Leu Ala Asp Met Glu Ile Gln Leu Gly Ala Val
            1300                1305            1310

Lys Arg Ile His Ala Leu Leu Lys Thr Glu Ala Glu Ser Tyr Glu Gly
            1315                1320            1325

Leu Leu Ala Pro Ser Leu Ile Pro Lys Asn Trp Pro Asp Gln Gly Lys
            1330                1335            1340

Ile Gln Ile Gln Asn Leu Ser Val Arg Tyr Asp Ser Ser Leu Lys Pro
1345                1350                1355                1360

Val Leu Lys His Val Asn Thr Leu Ile Ser Pro Gly Gln Lys Ile Gly
            1365                1370            1375

Ile Cys Gly Arg Thr Gly Ser Gly Lys Ser Ser Phe Ser Leu Ala Phe
            1380                1385            1390

Phe Arg Met Val Asp Met Phe Glu Gly Arg Ile Ile Asp Gly Ile
            1395                1400            1405

Asp Ile Ala Lys Leu Pro Leu His Thr Leu Arg Ser Arg Leu Ser Ile
            1410                1415            1420

Ile Leu Gln Asp Pro Val Leu Phe Ser Gly Thr Ile Arg Phe Asn Leu
1425                1430                1435                1440

Asp Pro Glu Lys Lys Cys Ser Asp Ser Thr Leu Trp Glu Ala Leu Glu
            1445                1450            1455

Ile Ala Gln Leu Lys Leu Val Val Lys Ala Leu Pro Gly Gly Leu Asp
            1460                1465            1470

Ala Ile Ile Thr Glu Gly Gly Glu Asn Phe Ser Gln Gly Gln Arg Gln
            1475                1480            1485

Leu Phe Cys Leu Ala Arg Ala Phe Val Arg Lys Thr Ser Ile Phe Ile
            1490                1495            1500

Met Asp Glu Ala Thr Ala Ser Ile Asp Met Ala Thr Glu Asn Ile Leu
1505                1510                1515                1520

Gln Lys Val Val Met Thr Ala Phe Ala Asp Arg Thr Val Val Thr Ile
            1525                1530            1535

Ala His Arg Val His Thr Ile Leu Ser Ala Asp Leu Val Met Val Leu
            1540                1545            1550

Lys Arg Gly Ala Ile Leu Glu Phe Asp Lys Pro Glu Thr Leu Leu Ser
            1555                1560            1565

Gln Lys Asp Ser Val Phe Ala Ser Phe Val Arg Ala Asp Lys
            1570                1575            1580

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (ii) MOLECULE TYPE: Amino acid (xi) SEQUENCE DESCRIPTION: SEQ ID NO:10:

Met Pro Leu Ala Phe Cys Gly Thr
 1               5

(2) INFORMATION FOR SEQ ID NO:11:

(i) SEQUENCE CHARACTERISTICS:
        (A) LENGTH: 11 amino acids
        (B) TYPE: amino acid
```

(D) TOPOLOGY: linear (ii) MOLECULE TYPE: Amino acid (xi) SEQUENCE DESCRIPTION: SEQ ID NO:11:

Asn His Ser Ala Ala Tyr Arg Val Asp Gln Gly
 1               5

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: nucleic acids (iii) HYPOTHETICAL: NO (iv) ANTI-SENSE: NO (xi) SEQUENCE DESCRIPTION: SEQ ID NO:12:

CACGCTCAGG TTCTGGAT                                                    18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: nucleic acids (iii) HYPOTHETICAL: NO (iv) ANTI-SENSE: YES (xi) SEQUENCE DESCRIPTION: SEQ ID NO:13:

TCAACTGGAT GGTGAGGA                                                    18

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:14:

TGACATCGCC AAACTGC                                                     17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:15:

TCCTGGCAGT GCCTTCA                                                      17

(2) INFORMATION FOR SEQ ID NO:16:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:16:

TCCTCTCAGG GTCCAGGTTA                                                   20

(2) INFORMATION FOR SEQ ID NO:17:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:17:

ACAAGGAGCC TGGGGAT                                                      17

(2) INFORMATION FOR SEQ ID NO:18:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:18:

TGCATGGGTC CCAGTGA                                                      17

(2) INFORMATION FOR SEQ ID NO:19:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:19:

```
TTGACCATTC ACCACATTGG TGTGC                                                25
```

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:20:

```
TCCTGGCAGT GCCTTCA                                                         17
```

(2) INFORMATION FOR SEQ ID NO:21:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:21:

```
Met Pro Leu Ala Phe Cys Gly Thr
1               5
```

(2) INFORMATION FOR SEQ ID NO:22:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:22:

```
Asn His Ser Ala Ala Tyr Arg Val Asp Gln Gly
1               5                   10
```

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Nucleic Acid (xi) SEQUENCE DESCRIPTION: SEQ ID NO:23:

```
GAGAGAAGCT TNTGNGGNGA NAANCA                                               26
```

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Nucleic Acid (xi) SEQUENCE DESCRIPTION: SEQ ID NO:24:

```
GAGAGAGAAT TCCNTGNTCN ACNCNNTA                                                    28

(2) INFORMATION FOR SEQ ID NO:25:

(i) SEQUENCE CHARACTERISTICS:
        (A) LENGTH:  47 base pairs
        (B) TYPE: nucleic acid
        (C) STRANDEDNESS: single
        (D) TOPOLOGY: linear (ii) MOLECULE TYPE: Nucleic Acid (xi) SEQUENCE DESCRIPTION: SEQ ID NO:25:

TTTTGCGGGA CGGAGAATCA CTCGGCCGCC TACCGCGTCG ACCAAGG                                47

(2) INFORMATION FOR SEQ ID NO:26:

(i) SEQUENCE CHARACTERISTICS:
        (A) LENGTH:  9 base pairs
        (B) TYPE: nucleic acid
        (C) STRANDEDNESS: single
        (D) TOPOLOGY: linear (ii) MOLECULE TYPE: Nucleic Acid (xi) SEQUENCE DESCRIPTION: SEQ ID NO:26:

GCCNCCAUG                                                                          9

(2) INFORMATION FOR SEQ ID NO:27:

(i) SEQUENCE CHARACTERISTICS:
        (A) LENGTH: 4635 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 37..4533

(xi) SEQUENCE DESCRIPTION: SEQ ID NO:27:

GCGCGGAGCC GGAGCCGAGC CCGTGCGCGC GCCACC ATG CCT TTG GCC TTC TGC      54
                                       Met Pro Leu Ala Phe Cys
                                         1               5

GGC ACC GAG AAC CAC TCG GCC GCC TAC CGG GTG GAC CAA GGC GTC CTC    102
Gly Thr Glu Asn His Ser Ala Ala Tyr Arg Val Asp Gln Gly Val Leu
             10                  15                  20

AAC AAC GGC TGC TTC GTG GAC GCG CTC AAT GTG GTG CCA CAT GTC TTT    150
Asn Asn Gly Cys Phe Val Asp Ala Leu Asn Val Val Pro His Val Phe
         25                  30                  35

CTG CTC TTC ATC ACC TTC CCC ATC CTC TTC ATC GGA TGG GGC AGC CAG    198
Leu Leu Phe Ile Thr Phe Pro Ile Leu Phe Ile Gly Trp Gly Ser Gln
     40                  45                  50

AGC TCC AAG GTG CAC ATT CAC CAC AGC ACC TGG CTC CAT TTC CCG GGG    246
Ser Ser Lys Val His Ile His His Ser Thr Trp Leu His Phe Pro Gly
 55                  60                  65                  70

CAC AAC CTG CGC TGG ATC CTG ACC TTC ATA CTG CTC TTC GTC CTC GTG    294
His Asn Leu Arg Trp Ile Leu Thr Phe Ile Leu Leu Phe Val Leu Val
             75                  80                  85
```

```
TGT GAG ATC GCT GAG GGT ATC CTG TCT GAC GGG GTG ACA GAA TCC CGC      342
Cys Glu Ile Ala Glu Gly Ile Leu Ser Asp Gly Val Thr Glu Ser Arg
             90                  95                 100

CAC CTC CAC TTA TAC ATG CCA GCT GGG ATG GCA TTC ATG GCT GCC ATC      390
His Leu His Leu Tyr Met Pro Ala Gly Met Ala Phe Met Ala Ala Ile
            105                 110                 115

ACC TCT GTG GTC TAC TAC CAT AAC ATT GAG ACC TCT AAC TTT CCC AAG      438
Thr Ser Val Val Tyr Tyr His Asn Ile Glu Thr Ser Asn Phe Pro Lys
        120                 125                 130

CTG CTG ATT GCT CTG CTC ATC TAC TGG ACC CTG GCC TTC ATC ACG AAG      486
Leu Leu Ile Ala Leu Leu Ile Tyr Trp Thr Leu Ala Phe Ile Thr Lys
135                 140                 145                 150

ACC ATC AAG TTC GTC AAG TTC TAC GAC CAC GCC ATT GGC TTC TCT CAG      534
Thr Ile Lys Phe Val Lys Phe Tyr Asp His Ala Ile Gly Phe Ser Gln
                155                 160                 165

CTG CGC TTC TGC CTC ACG GGG CTT CTG GTG ATC CTC TAC GGG ATG CTG      582
Leu Arg Phe Cys Leu Thr Gly Leu Leu Val Ile Leu Tyr Gly Met Leu
            170                 175                 180

CTG CTT GTG GAG GTC AAT GTC ATC CGG GTG AGG AGA TAC GTC TTC TTC      630
Leu Leu Val Glu Val Asn Val Ile Arg Val Arg Arg Tyr Val Phe Phe
        185                 190                 195

AAG ACA CCA AGG GAA GTA AAG CCC CCC GAG GAC CTA CAG GAC CTG GGT      678
Lys Thr Pro Arg Glu Val Lys Pro Pro Glu Asp Leu Gln Asp Leu Gly
200                 205                 210

GTG CGC TTT CTG CAG CCC TTC GTT AAC CTG CTA TCA AAG GGG ACC TAC      726
Val Arg Phe Leu Gln Pro Phe Val Asn Leu Leu Ser Lys Gly Thr Tyr
215                 220                 225                 230

TGG TGG ATG AAT GCC TTC ATC AAG ACT GCT CAC AAG AAG CCC ATC GAC      774
Trp Trp Met Asn Ala Phe Ile Lys Thr Ala His Lys Lys Pro Ile Asp
                235                 240                 245

CTG CGG GCC ATC GGG AAG CTG CCC ATT GCC ATG AGA GCC CTC ACC AAC      822
Leu Arg Ala Ile Gly Lys Leu Pro Ile Ala Met Arg Ala Leu Thr Asn
            250                 255                 260

TAC CAG CGA CTC TGC TTG GCC TTC GAT GCC CAG GCG CGG AAG GAC ACA      870
Tyr Gln Arg Leu Cys Leu Ala Phe Asp Ala Gln Ala Arg Lys Asp Thr
        265                 270                 275

CAG AGC CAG CAG GGT GCC CGG GCC ATC TGG AGG GCT CTC TGT CAT GCC      918
Gln Ser Gln Gln Gly Ala Arg Ala Ile Trp Arg Ala Leu Cys His Ala
280                 285                 290

TTT GGG AGA CGG CTG GTC CTC AGC AGC ACA TTC CGT ATC CTG GCC GAC      966
Phe Gly Arg Arg Leu Val Leu Ser Ser Thr Phe Arg Ile Leu Ala Asp
295                 300                 305                 310

CTC CTG GGC TTT GCT GGG CCA CTC TGC ATC TTC GGG ATC GTG GAC CAC     1014
Leu Leu Gly Phe Ala Gly Pro Leu Cys Ile Phe Gly Ile Val Asp His
                315                 320                 325

CTC GGG AAG GAG AAC CAC GTC TTC CAG CCC AAG ACA CAG TTT CTT GGA     1062
Leu Gly Lys Glu Asn His Val Phe Gln Pro Lys Thr Gln Phe Leu Gly
            330                 335                 340

GTT TAC TTT GTC TCA TCC CAA GAG TTC CTC GGC AAT GCC TAT GTC TTG     1110
Val Tyr Phe Val Ser Ser Gln Glu Phe Leu Gly Asn Ala Tyr Val Leu
        345                 350                 355

GCT GTT CTT CTG TTC CTT GCC CTC CTG CTG CAA AGG ACC TTT CTA CAA     1158
Ala Val Leu Leu Phe Leu Ala Leu Leu Leu Gln Arg Thr Phe Leu Gln
360                 365                 370

GCC TCG TAC TAC GTT GCC ATT GAA ACT GGG ATC AAC CTG AGA GGA GCA     1206
Ala Ser Tyr Tyr Val Ala Ile Glu Thr Gly Ile Asn Leu Arg Gly Ala
375                 380                 385                 390

ATC CAG ACC AAG ATT TAC AAT AAG ATC ATG CAC TTG TCT ACT TCC AAC     1254
Ile Gln Thr Lys Ile Tyr Asn Lys Ile Met His Leu Ser Thr Ser Asn
```

-continued

```
             395                 400                     405
CTG TCC ATG GGG GAA ATG ACT GCT GGG CAG ATC TGC AAC CTG GTG GCC      1302
Leu Ser Met Gly Glu Met Thr Ala Gly Gln Ile Cys Asn Leu Val Ala
            410                 415                 420

ATC GAC ACC AAC CAG CTC ATG TGG TTT TTC TTC TTA TGC CCA AAC CTC      1350
Ile Asp Thr Asn Gln Leu Met Trp Phe Phe Phe Leu Cys Pro Asn Leu
            425                 430                 435

TGG GCT ATG CCG GTA CAG ATC ATT GTG GGC GTG ATC CTC CTC TAC TAC      1398
Trp Ala Met Pro Val Gln Ile Ile Val Gly Val Ile Leu Leu Tyr Tyr
            440                 445                 450

ATC CTT GGG GTC AGC GCC TTG ATT GGA GCG GCT GTC ATC ATT CTG CTG      1446
Ile Leu Gly Val Ser Ala Leu Ile Gly Ala Ala Val Ile Ile Leu Leu
455                 460                 465                 470

GCT CCT GTA CAG TAC TTT GTG GCC ACC AAG CTG TCC CAG GCA CAG CGG      1494
Ala Pro Val Gln Tyr Phe Val Ala Thr Lys Leu Ser Gln Ala Gln Arg
            475                 480                 485

ACG ACC CTG GAA TAT TCC AAT GAG AGG CTG AAG CAG ACC AAT GAG ATG      1542
Thr Thr Leu Glu Tyr Ser Asn Glu Arg Leu Lys Gln Thr Asn Glu Met
            490                 495                 500

CTC CGG GGC ATC AAG TTG CTC AAG CTC TAT GCG TGG GAG AAC ATC TTC      1590
Leu Arg Gly Ile Lys Leu Leu Lys Leu Tyr Ala Trp Glu Asn Ile Phe
            505                 510                 515

TGC TCC AGG GTG GAG AAG ACA CGC AGG AAG GAA ATG ACC AGC CTC AGG      1638
Cys Ser Arg Val Glu Lys Thr Arg Arg Lys Glu Met Thr Ser Leu Arg
            520                 525                 530

GCC TTC GCT GTC TAC ACC TCC ATC TCC ATC TTC ATG AAC ACA GCT ATC      1686
Ala Phe Ala Val Tyr Thr Ser Ile Ser Ile Phe Met Asn Thr Ala Ile
535                 540                 545                 550

CCC ATC GCT GCT GTC CTC ATC ACC TTC GTG GGC CAC GTC AGC TTC TTC      1734
Pro Ile Ala Ala Val Leu Ile Thr Phe Val Gly His Val Ser Phe Phe
            555                 560                 565

AAA GAG TCG GAC TTC TCG CCC TCG GTG GCC TTT GCC TCT CTC TCT CTC      1782
Lys Glu Ser Asp Phe Ser Pro Ser Val Ala Phe Ala Ser Leu Ser Leu
            570                 575                 580

TTC CAC ATC CTG GTC ACA CCG CTG TTC CTG CTG TCT AGT GTG GTT CGG      1830
Phe His Ile Leu Val Thr Pro Leu Phe Leu Leu Ser Ser Val Val Arg
            585                 590                 595

TCC ACT GTC AAG GCC CTG GTG AGC GTG CAA AAG CTG AGT GAG TTC CTG      1878
Ser Thr Val Lys Ala Leu Val Ser Val Gln Lys Leu Ser Glu Phe Leu
            600                 605                 610

TCC AGT GCA GAG ATC CGT GAG GAA CAG TGT GCC CCC CGA GAG CCC GCA      1926
Ser Ser Ala Glu Ile Arg Glu Glu Gln Cys Ala Pro Arg Glu Pro Ala
615                 620                 625                 630

CCC CAA GGC CAA GCG GGC AAG TAC CAG GCG GTG CCC CTC AAG GTC GTA      1974
Pro Gln Gly Gln Ala Gly Lys Tyr Gln Ala Val Pro Leu Lys Val Val
            635                 640                 645

AAC CGC AAG CGC CCA GCC CGA GAA GAA GTC CGG GAC CTC TTG GGC CCA      2022
Asn Arg Lys Arg Pro Ala Arg Glu Glu Val Arg Asp Leu Leu Gly Pro
            650                 655                 660

CTG CAG AGG CTG ACT CCC AGC ACG GAT GGA GAC GCT GAC AAC TTC TGT      2070
Leu Gln Arg Leu Thr Pro Ser Thr Asp Gly Asp Ala Asp Asn Phe Cys
            665                 670                 675

GTC CAG ATC ATC GGA GGC TTC TTC ACC TGG ACC CCT GAT GGA ATC CCC      2118
Val Gln Ile Ile Gly Gly Phe Phe Thr Trp Thr Pro Asp Gly Ile Pro
            680                 685                 690

ACC CTG TCC AAC ATC ACC ATC CGT ATC CCC CGA GGT CAG CTG ACC ATG      2166
Thr Leu Ser Asn Ile Thr Ile Arg Ile Pro Arg Gly Gln Leu Thr Met
695                 700                 705                 710

ATC GTG GGG CAG GTG GGC TGT GGC AAG TCC TCG CTC CTT CTG GCC ACC      2214
```

-continued

```
           Ile Val Gly Gln Val Gly Cys Gly Lys Ser Ser Leu Leu Ala Thr
                           715                 720                 725

CTG GGG GAG ATG CAG AAG GTC TCT GGA GCT GTC TTC TGG AAC AGC CTT          2262
Leu Gly Glu Met Gln Lys Val Ser Gly Ala Val Phe Trp Asn Ser Leu
            730                 735                 740

CCA GAC AGC GAG GGG AGA AGA CCC CAG CAA CCC AGA GCG GGA GAC AGC          2310
Pro Asp Ser Glu Gly Arg Arg Pro Gln Gln Pro Arg Ala Gly Asp Ser
745                 750                 755

GGC CGA TTC GGA TGC CAG GAG CAG AGG CCC TGT GGC TAC GCA TCT CAG          2358
Gly Arg Phe Gly Cys Gln Glu Gln Arg Pro Cys Gly Tyr Ala Ser Gln
        760                 765                 770

AAA CCA TGG CTG CTA AAT GCC ACT GTG GAG GAG AAC ATC ACC TTC GAG          2406
Lys Pro Trp Leu Leu Asn Ala Thr Val Glu Glu Asn Ile Thr Phe Glu
775                 780                 785                 790

AGT CCC TTC AAT AAG CAA CGG TAC AAG ATG GTC ATC GAA GCC TGC TCC          2454
Ser Pro Phe Asn Lys Gln Arg Tyr Lys Met Val Ile Glu Ala Cys Ser
                795                 800                 805

CTG CAG CCA GAC ATA GAC ATC CTG CCC CAT GGA GAC CAG ACT CAG ATT          2502
Leu Gln Pro Asp Ile Asp Ile Leu Pro His Gly Asp Gln Thr Gln Ile
            810                 815                 820

GGG GAA CGA GGC ATC AAC TTG AGT ACT GGT GGT CAG CGT CCA GAT CAG          2550
Gly Glu Arg Gly Ile Asn Leu Ser Thr Gly Gly Gln Arg Pro Asp Gln
825                 830                 835

TGT AGA CCC GAG CCC TCT ACC AGC ACA CCA ATG ATT GTC TTT TTG GAT          2598
Cys Arg Pro Glu Pro Ser Thr Ser Thr Pro Met Ile Val Phe Leu Asp
        840                 845                 850

GAC CCT TTC TCG GCT CTG GAT GTC CAT CTG AGT GAC CAC CTA ATG CAG          2646
Asp Pro Phe Ser Ala Leu Asp Val His Leu Ser Asp His Leu Met Gln
855                 860                 865                 870

GCT GGC ATC CTC GAG CTG CTC CGG GAT GAC AAG AGG ACA GTG GTC TTG          2694
Ala Gly Ile Leu Glu Leu Leu Arg Asp Asp Lys Arg Thr Val Val Leu
                875                 880                 885

GTG ACC CAC AAG CTA CAG TAC CTG CCT CAT GCT GAC TGG ATC ATT GCT          2742
Val Thr His Lys Leu Gln Tyr Leu Pro His Ala Asp Trp Ile Ile Ala
            890                 895                 900

ATG AAG GAT GGC ACC ATT CAG AGG GAG GGG ACA CTC AAG GAC TTC CAG          2790
Met Lys Asp Gly Thr Ile Gln Arg Glu Gly Thr Leu Lys Asp Phe Gln
905                 910                 915

AGG TCT GAG TGC CAG CTC TTT GAG CAT TGG AAG ACC CTC ATG AAC CGG          2838
Arg Ser Glu Cys Gln Leu Phe Glu His Trp Lys Thr Leu Met Asn Arg
        920                 925                 930

CAG GAC CAA GAG CTG GAG AAG GAG ACA GTC ATG GAG AGA AAA GCC CCA          2886
Gln Asp Gln Glu Leu Glu Lys Glu Thr Val Met Glu Arg Lys Ala Pro
935                 940                 945                 950

GAG CCA TCT CAG GGC CTG CCC CGT GCC ATG TCC TCA AGA GAT GGC CTT          2934
Glu Pro Ser Gln Gly Leu Pro Arg Ala Met Ser Ser Arg Asp Gly Leu
                955                 960                 965

CTG CTG GAT GAG GAT GAG GAG GAA GAG GAG GCA GCC GAG AGC GAG GAA          2982
Leu Leu Asp Glu Asp Glu Glu Glu Glu Glu Ala Ala Glu Ser Glu Glu
            970                 975                 980

GAT GAC AAC TTA TCC TCT GTG CTG CAT CAG CGA GCC AAG ATC CCA TGG          3030
Asp Asp Asn Leu Ser Ser Val Leu His Gln Arg Ala Lys Ile Pro Trp
985                 990                 995

CGA GCC TGC ACC AAG TAT TTG TCC TCT GCT GGC ATC CTG CTC CTG TCC          3078
Arg Ala Cys Thr Lys Tyr Leu Ser Ser Ala Gly Ile Leu Leu Leu Ser
        1000                1005                1010

CTG CTT GTC TTC TCC CAG CTG CTC AAG CAC ATG GTC TTG GTG GCC ATT          3126
Leu Leu Val Phe Ser Gln Leu Leu Lys His Met Val Leu Val Ala Ile
1015                1020                1025                1030
```

```
GAC TAC TGG CTG GCC AAG TGG ACG GAC AGT GCC CTG GTC CTG AGC CCC        3174
Asp Tyr Trp Leu Ala Lys Trp Thr Asp Ser Ala Leu Val Leu Ser Pro
                1035                1040                1045

GCC GCC AGG AAC TGC TCC CTC AGC CAG GAA TGT GCC CTG GAC CAA TCT        3222
Ala Ala Arg Asn Cys Ser Leu Ser Gln Glu Cys Ala Leu Asp Gln Ser
                1050                1055                1060

GTC TAT GCC ATG GTA TTC ACC GTG CTC TGC AGC CTG GGT ATC GCG CTG        3270
Val Tyr Ala Met Val Phe Thr Val Leu Cys Ser Leu Gly Ile Ala Leu
                1065                1070                1075

TGC CTT GTC ACC TCT GTC ACT GTG GAG TGG ACG GGA CTG AAG GTG GCC        3318
Cys Leu Val Thr Ser Val Thr Val Glu Trp Thr Gly Leu Lys Val Ala
                1080                1085                1090

AAG AGG CTG CAT CGC AGC CTG CTC AAC CGT ATC ATC CTG GCT CCC ATG        3366
Lys Arg Leu His Arg Ser Leu Leu Asn Arg Ile Ile Leu Ala Pro Met
1095                1100                1105                1110

AGG TTC TTT GAG ACC ACG CCC CTG GGG AGT ATC CTG AAC AGA TTT TCA        3414
Arg Phe Phe Glu Thr Thr Pro Leu Gly Ser Ile Leu Asn Arg Phe Ser
                1115                1120                1125

TCT GAC TGT AAC ACC ATT GAC CAG CAT ATC CCG TCC ACG CTG GAG TGC        3462
Ser Asp Cys Asn Thr Ile Asp Gln His Ile Pro Ser Thr Leu Glu Cys
                1130                1135                1140

CTG AGC AGA TCC ACC TTA CTC TGT GTC TCC GCC CTG GCT GTC ATC TCC        3510
Leu Ser Arg Ser Thr Leu Leu Cys Val Ser Ala Leu Ala Val Ile Ser
                1145                1150                1155

TAC GTC ACG CCT GTG TTC CTA GTG GCC CTC TTA CCC CTC GCC GTC GTG        3558
Tyr Val Thr Pro Val Phe Leu Val Ala Leu Leu Pro Leu Ala Val Val
                1160                1165                1170

TGC TAC TTC ATC CAG AAG TAC TTC CGA GTG GCG TCC AGG GAC CTG CAG        3606
Cys Tyr Phe Ile Gln Lys Tyr Phe Arg Val Ala Ser Arg Asp Leu Gln
1175                1180                1185                1190

CAG CTG GAC GAC ACA ACA CAG CTC CCT CTG CTC TCA CAC TTT GCT GAA        3654
Gln Leu Asp Asp Thr Thr Gln Leu Pro Leu Leu Ser His Phe Ala Glu
                1195                1200                1205

ACT GTG GAA GGA CTC ACC ACC ATC CGT GCC TTC AGG TAC GAG GCC CGG        3702
Thr Val Glu Gly Leu Thr Thr Ile Arg Ala Phe Arg Tyr Glu Ala Arg
                1210                1215                1220

TTC CAG CAG AAG CTC CTA GAG TAC ACC GAC TCC AAC AAC ATT GCC TCT        3750
Phe Gln Gln Lys Leu Leu Glu Tyr Thr Asp Ser Asn Asn Ile Ala Ser
                1225                1230                1235

CTC TTC CTC ACA GCA GCC AAC AGG TGG CTG GAA GTC CGC ATG GAG TAC        3798
Leu Phe Leu Thr Ala Ala Asn Arg Trp Leu Glu Val Arg Met Glu Tyr
                1240                1245                1250

ATC GGA GCA TGC GTG GTA CTC ATC GCC GCT GCC ACC TCC ATC TCC AAC        3846
Ile Gly Ala Cys Val Val Leu Ile Ala Ala Ala Thr Ser Ile Ser Asn
1255                1260                1265                1270

TCC CTA CAC AGG GAG CTC TCA GCC GGC CTA GTA GGC CTG GGC CTC ACC        3894
Ser Leu His Arg Glu Leu Ser Ala Gly Leu Val Gly Leu Gly Leu Thr
                1275                1280                1285

TAT GCC TTG ATG ATT GGG ATC TGC GGC CGC ACA GGC AGT GGA AAA TCC        3942
Tyr Ala Leu Met Ile Gly Ile Cys Gly Arg Thr Gly Ser Gly Lys Ser
                1290                1295                1300

TCC TTC TCT CTC GCC TTT TTC CGA ATG GTG GAT ATG TTT GAA GGG CGT        3990
Ser Phe Ser Leu Ala Phe Phe Arg Met Val Asp Met Phe Glu Gly Arg
                1305                1310                1315

ATC ATC ATC GAT GGC ATT GAC ATC GCC AAG CTG CCG CTG CAC ACG CTC        4038
Ile Ile Ile Asp Gly Ile Asp Ile Ala Lys Leu Pro Leu His Thr Leu
                1320                1325                1330

CGC TCA CGC CTG TCT ATC ATC CTA CAG GAC CCT GTT CTC TTC AGT GGT        4086
Arg Ser Arg Leu Ser Ile Ile Leu Gln Asp Pro Val Leu Phe Ser Gly
1335                1340                1345                1350
```

```
ACC ATC AGA TTC AAC CTG GAC CCA GAG AAG AAA TGC TCA GAC AGC ACG      4134
Thr Ile Arg Phe Asn Leu Asp Pro Glu Lys Lys Cys Ser Asp Ser Thr
            1355                1360                1365

CTG TGG GAG GCT CTG GAG ATC GCT CAG CTG AAG CTG GTG GTG AAG GCC      4182
Leu Trp Glu Ala Leu Glu Ile Ala Gln Leu Lys Leu Val Val Lys Ala
            1370                1375                1380

CTG CCA GGA GGC CTG GAT GCC ATC ATC ACG GAA GGA GGG GAG AAT TTT      4230
Leu Pro Gly Gly Leu Asp Ala Ile Ile Thr Glu Gly Gly Glu Asn Phe
        1385                1390                1395

AGC CAG GGC CAG AGG CAG CTG TTC TGC CTG GCC CGG GCC TTT GTG AGG      4278
Ser Gln Gly Gln Arg Gln Leu Phe Cys Leu Ala Arg Ala Phe Val Arg
        1400                1405                1410

AAG ACC AGC ATC TTC ATC ATG GAT GAA GCA ACT GCC TCC ATC GAC ATG      4326
Lys Thr Ser Ile Phe Ile Met Asp Glu Ala Thr Ala Ser Ile Asp Met
1415                1420                1425                1430

GCT ACG GAA AAT ATC CTC CAG AAG GTG GTG ATG ACA GCC TTC GCA GAC      4374
Ala Thr Glu Asn Ile Leu Gln Lys Val Val Met Thr Ala Phe Ala Asp
            1435                1440                1445

CGC ACC GTG GTC ACC ATC GCG CAC CGC GTG CAC ACC ATC CTG AGT GCA      4422
Arg Thr Val Val Thr Ile Ala His Arg Val His Thr Ile Leu Ser Ala
            1450                1455                1460

GAC CTA GTG ATG GTC CTG AAG AGG GGC GCG ATC CTG GAG TTC GAC AAG      4470
Asp Leu Val Met Val Leu Lys Arg Gly Ala Ile Leu Glu Phe Asp Lys
            1465                1470                1475

CCG GAA AAG CTT CTC AGC CAG AAG GAC AGC GTC TTT GCC TCC TTT GTC      4518
Pro Glu Lys Leu Leu Ser Gln Lys Asp Ser Val Phe Ala Ser Phe Val
        1480                1485                1490

CGC GCG GAC AAA TGACCAGCCA GCGCCAAAGT GCCACCCCAC ACCTCACCTG          4570
Arg Ala Asp Lys
1495

CTTGCCATGG ATTTCTTACT GTAAATCACT TGTAAATAAA GAAACTAATT CTTTGCTAAA    4630

AAAAA                                                                 4635

(2) INFORMATION FOR SEQ ID NO:28:

(i) SEQUENCE CHARACTERISTICS:
        (A) LENGTH: 1498 amino acids
        (B) TYPE: amino acid
        (D) TOPOLOGY: linear (ii) MOLECULE TYPE: protein (xi) SEQUENCE DESCRIPTION: SEQ ID NO:28:

Met Pro Leu Ala Phe Cys Gly Thr Glu Asn His Ser Ala Ala Tyr Arg
  1               5                  10                  15

Val Asp Gln Gly Val Leu Asn Asn Gly Cys Phe Val Asp Ala Leu Asn
                 20                  25                  30

Val Val Pro His Val Phe Leu Leu Phe Ile Thr Phe Pro Ile Leu Phe
             35                  40                  45

Ile Gly Trp Gly Ser Gln Ser Ser Lys Val His Ile His His Ser Thr
     50                  55                  60

Trp Leu His Phe Pro Gly His Asn Leu Arg Trp Ile Leu Thr Phe Ile
 65                  70                  75                  80

Leu Leu Phe Val Leu Val Cys Glu Ile Ala Glu Gly Ile Leu Ser Asp
                 85                  90                  95

Gly Val Thr Glu Ser Arg His Leu His Leu Tyr Met Pro Ala Gly Met
            100                 105                 110

Ala Phe Met Ala Ala Ile Thr Ser Val Val Tyr Tyr His Asn Ile Glu
```

```
            115                 120                 125
Thr Ser Asn Phe Pro Lys Leu Leu Ile Ala Leu Leu Ile Tyr Trp Thr
    130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Val Glu Val Asn Val Ile Arg Val
                180                 185                 190

Arg Arg Tyr Val Phe Phe Lys Thr Pro Arg Glu Val Lys Pro Pro Glu
            195                 200                 205

Asp Leu Gln Asp Leu Gly Val Arg Phe Leu Gln Pro Phe Val Asn Leu
    210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Gly Lys Leu Pro Ile Ala
                245                 250                 255

Met Arg Ala Leu Thr Asn Tyr Gln Arg Leu Cys Leu Ala Phe Asp Ala
            260                 265                 270

Gln Ala Arg Lys Asp Thr Gln Ser Gln Gln Gly Ala Arg Ala Ile Trp
    275                 280                 285

Arg Ala Leu Cys His Ala Phe Gly Arg Arg Leu Val Leu Ser Ser Thr
290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

Gly Asn Ala Tyr Val Leu Ala Val Leu Leu Phe Leu Ala Leu Leu Leu
    355                 360                 365

Gln Arg Thr Phe Leu Gln Ala Ser Tyr Tyr Val Ala Ile Glu Thr Gly
    370                 375                 380

Ile Asn Leu Arg Gly Ala Ile Gln Thr Lys Ile Tyr Asn Lys Ile Met
385                 390                 395                 400

His Leu Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
                420                 425                 430

Phe Leu Cys Pro Asn Leu Trp Ala Met Pro Val Gln Ile Ile Val Gly
            435                 440                 445

Val Ile Leu Leu Tyr Tyr Ile Leu Gly Val Ser Ala Leu Ile Gly Ala
450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu Tyr Ser Asn Glu Arg Leu
                485                 490                 495

Lys Gln Thr Asn Glu Met Leu Arg Gly Ile Lys Leu Leu Lys Leu Tyr
            500                 505                 510

Ala Trp Glu Asn Ile Phe Cys Ser Arg Val Glu Lys Thr Arg Arg Lys
    515                 520                 525

Glu Met Thr Ser Leu Arg Ala Phe Ala Val Tyr Thr Ser Ile Ser Ile
530                 535                 540
```

-continued

```
Phe Met Asn Thr Ala Ile Pro Ile Ala Ala Val Leu Ile Thr Phe Val
545                 550                 555                 560

Gly His Val Ser Phe Lys Glu Ser Asp Phe Ser Pro Ser Val Ala
            565                 570                 575

Phe Ala Ser Leu Ser Leu Phe His Ile Leu Val Thr Pro Leu Phe Leu
            580                 585                 590

Leu Ser Ser Val Val Arg Ser Thr Val Lys Ala Leu Val Ser Val Gln
            595                 600                 605

Lys Leu Ser Glu Phe Leu Ser Ser Ala Glu Ile Arg Glu Glu Gln Cys
610                 615                 620

Ala Pro Arg Glu Pro Ala Pro Gln Gly Gln Ala Gly Lys Tyr Gln Ala
625                 630                 635                 640

Val Pro Leu Lys Val Val Asn Arg Lys Arg Pro Ala Arg Glu Glu Val
                645                 650                 655

Arg Asp Leu Leu Gly Pro Leu Gln Arg Leu Thr Pro Ser Thr Asp Gly
            660                 665                 670

Asp Ala Asp Asn Phe Cys Val Gln Ile Ile Gly Gly Phe Phe Thr Trp
            675                 680                 685

Thr Pro Asp Gly Ile Pro Thr Leu Ser Asn Ile Thr Ile Arg Ile Pro
690                 695                 700

Arg Gly Gln Leu Thr Met Ile Val Gly Gln Val Gly Cys Gly Lys Ser
705                 710                 715                 720

Ser Leu Leu Leu Ala Thr Leu Gly Glu Met Gln Lys Val Ser Gly Ala
                725                 730                 735

Val Phe Trp Asn Ser Leu Pro Asp Ser Glu Gly Arg Arg Pro Gln Gln
            740                 745                 750

Pro Arg Ala Gly Asp Ser Gly Arg Phe Gly Cys Gln Glu Gln Arg Pro
            755                 760                 765

Cys Gly Tyr Ala Ser Gln Lys Pro Trp Leu Leu Asn Ala Thr Val Glu
            770                 775                 780

Glu Asn Ile Thr Phe Glu Ser Pro Phe Asn Lys Gln Arg Tyr Lys Met
785                 790                 795                 800

Val Ile Glu Ala Cys Ser Leu Gln Pro Asp Ile Asp Ile Leu Pro His
                805                 810                 815

Gly Asp Gln Thr Gln Ile Gly Glu Arg Gly Ile Asn Leu Ser Thr Gly
            820                 825                 830

Gly Gln Arg Pro Asp Gln Cys Arg Pro Glu Pro Ser Thr Ser Thr Pro
            835                 840                 845

Met Ile Val Phe Leu Asp Asp Pro Phe Ser Ala Leu Asp Val His Leu
850                 855                 860

Ser Asp His Leu Met Gln Ala Gly Ile Leu Glu Leu Leu Arg Asp Asp
865                 870                 875                 880

Lys Arg Thr Val Val Leu Val Thr His Lys Leu Gln Tyr Leu Pro His
                885                 890                 895

Ala Asp Trp Ile Ile Ala Met Lys Asp Gly Thr Ile Gln Arg Glu Gly
            900                 905                 910

Thr Leu Lys Asp Phe Gln Arg Ser Glu Cys Gln Leu Phe Glu His Trp
            915                 920                 925

Lys Thr Leu Met Asn Arg Gln Asp Gln Glu Leu Glu Lys Glu Thr Val
            930                 935                 940

Met Glu Arg Lys Ala Pro Glu Pro Ser Gln Gly Leu Pro Arg Ala Met
945                 950                 955                 960
```

-continued

```
Ser Ser Arg Asp Gly Leu Leu Leu Asp Glu Asp Glu Glu Glu Glu
            965                 970                 975

Ala Ala Glu Ser Glu Glu Asp Asp Asn Leu Ser Ser Val Leu His Gln
            980                 985                 990

Arg Ala Lys Ile Pro Trp Arg Ala Cys Thr Lys Tyr Leu Ser Ser Ala
            995                1000                1005

Gly Ile Leu Leu Leu Ser Leu Leu Val Phe Ser Gln Leu Leu Lys His
           1010                1015                1020

Met Val Leu Val Ala Ile Asp Tyr Trp Leu Ala Lys Trp Thr Asp Ser
1025                1030                1035                1040

Ala Leu Val Leu Ser Pro Ala Ala Arg Asn Cys Ser Leu Ser Gln Glu
                   1045                1050                1055

Cys Ala Leu Asp Gln Ser Val Tyr Ala Met Val Phe Thr Val Leu Cys
                   1060                1065                1070

Ser Leu Gly Ile Ala Leu Cys Leu Val Thr Ser Val Thr Val Glu Trp
                   1075                1080                1085

Thr Gly Leu Lys Val Ala Lys Arg Leu His Arg Ser Leu Leu Asn Arg
                   1090                1095                1100

Ile Ile Leu Ala Pro Met Arg Phe Phe Glu Thr Thr Pro Leu Gly Ser
1105                1110                1115                1120

Ile Leu Asn Arg Phe Ser Ser Asp Cys Asn Thr Ile Asp Gln His Ile
                   1125                1130                1135

Pro Ser Thr Leu Glu Cys Leu Ser Arg Ser Thr Leu Leu Cys Val Ser
                   1140                1145                1150

Ala Leu Ala Val Ile Ser Tyr Val Thr Pro Val Phe Leu Val Ala Leu
                   1155                1160                1165

Leu Pro Leu Ala Val Val Cys Tyr Phe Ile Gln Lys Tyr Phe Arg Val
            1170                1175                1180

Ala Ser Arg Asp Leu Gln Gln Leu Asp Asp Thr Thr Gln Leu Pro Leu
1185                1190                1195                1200

Leu Ser His Phe Ala Glu Thr Val Glu Gly Leu Thr Thr Ile Arg Ala
                   1205                1210                1215

Phe Arg Tyr Glu Ala Arg Phe Gln Gln Lys Leu Leu Glu Tyr Thr Asp
            1220                1225                1230

Ser Asn Asn Ile Ala Ser Leu Phe Leu Thr Ala Ala Asn Arg Trp Leu
            1235                1240                1245

Glu Val Arg Met Glu Tyr Ile Gly Ala Cys Val Val Leu Ile Ala Ala
            1250                1255                1260

Ala Thr Ser Ile Ser Asn Ser Leu His Arg Glu Leu Ser Ala Gly Leu
1265                1270                1275                1280

Val Gly Leu Gly Leu Thr Tyr Ala Leu Met Ile Gly Ile Cys Gly Arg
                   1285                1290                1295

Thr Gly Ser Gly Lys Ser Ser Phe Ser Leu Ala Phe Phe Arg Met Val
                   1300                1305                1310

Asp Met Phe Glu Gly Arg Ile Ile Ile Asp Gly Ile Asp Ile Ala Lys
            1315                1320                1325

Leu Pro Leu His Thr Leu Arg Ser Arg Leu Ser Ile Ile Leu Gln Asp
1330                1335                1340

Pro Val Leu Phe Ser Gly Thr Ile Arg Phe Asn Leu Asp Pro Glu Lys
1345                1350                1355                1360

Lys Cys Ser Asp Ser Thr Leu Trp Glu Ala Leu Glu Ile Ala Gln Leu
                   1365                1370                1375

Lys Leu Val Val Lys Ala Leu Pro Gly Gly Leu Asp Ala Ile Ile Thr
```

-continued

```
                  1380             1385              1390
Glu Gly Gly Glu Asn Phe Ser Gln Gly Gln Arg Gln Leu Phe Cys Leu
             1395             1400             1405

Ala Arg Ala Phe Val Arg Lys Thr Ser Ile Phe Ile Met Asp Glu Ala
    1410             1415             1420

Thr Ala Ser Ile Asp Met Ala Thr Glu Asn Ile Leu Gln Lys Val Val
1425             1430             1435             1440

Met Thr Ala Phe Ala Asp Arg Thr Val Val Thr Ile Ala His Arg Val
                 1445             1450             1455

His Thr Ile Leu Ser Ala Asp Leu Val Met Val Leu Lys Arg Gly Ala
             1460             1465             1470

Ile Leu Glu Phe Asp Lys Pro Glu Lys Leu Leu Ser Gln Lys Asp Ser
         1475             1480             1485

Val Phe Ala Ser Phe Val Arg Ala Asp Lys
         1490             1495
```

(2) INFORMATION FOR SEQ ID NO:29:

(i) SEQUENCE CHARACTERISTICS:
        (A) LENGTH: 1498 amino acids
        (B) TYPE: amino acid
        (D) TOPOLOGY: linear (ii) MOLECULE TYPE: protein (xi) SEQUENCE DESCRIPTION: SEQ ID NO:29:

```
Met Pro Leu Ala Phe Cys Gly Thr Glu Asn His Ser Ala Ala Tyr Arg
 1               5                  10                  15

Val Asp Gln Gly Val Leu Asn Asn Gly Cys Phe Val Asp Ala Leu Asn
             20                  25                  30

Val Val Pro His Val Phe Leu Leu Phe Ile Thr Phe Pro Ile Leu Phe
         35                  40                  45

Ile Gly Trp Gly Ser Gln Ser Ser Lys Val His Ile His His Ser Thr
     50                  55                  60

Trp Leu His Phe Pro Gly His Asn Leu Arg Trp Ile Leu Thr Phe Ile
 65                  70                  75                  80

Leu Leu Phe Val Leu Val Cys Glu Ile Ala Glu Gly Ile Leu Ser Asp
                 85                  90                  95

Gly Val Thr Glu Ser Arg His Leu His Leu Tyr Met Pro Ala Gly Met
             100                 105                 110

Ala Phe Met Ala Ala Ile Thr Ser Val Val Tyr Tyr His Asn Ile Glu
         115                 120                 125

Thr Ser Asn Phe Pro Lys Leu Leu Ile Ala Leu Leu Ile Tyr Trp Thr
    130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                 165                 170                 175

Ile Leu Tyr Gly Met Leu Leu Val Glu Val Asn Val Ile Arg Val Arg
             180                 185                 190

Arg Arg Tyr Ile Phe Phe Lys Thr Pro Arg Glu Val Lys Pro Pro Glu
         195                 200                 205

Asp Leu Gln Asp Leu Gly Val Arg Phe Leu Gln Pro Phe Val Asn Leu
    210                 215                 220

Leu Ser Lys Gly Thr Tyr Trp Trp Met Asn Ala Phe Ile Lys Thr Ala
225                 230                 235                 240
```

-continued

```
His Lys Lys Pro Ile Asp Leu Arg Ala Ile Ala Lys Leu Pro Ile Ala
                245                 250                 255

Met Arg Ala Leu Thr Asn Tyr Gln Arg Leu Cys Val Ala Phe Asp Ala
            260                 265                 270

Gln Ala Arg Lys Asp Thr Gln Ser Pro Gln Gly Ala Arg Ala Ile Trp
        275                 280                 285

Arg Ala Leu Cys His Ala Phe Gly Arg Arg Leu Ile Leu Ser Ser Thr
    290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

Gly Asn Ala Tyr Val Leu Ala Val Leu Leu Phe Leu Ala Leu Leu Leu
        355                 360                 365

Gln Arg Thr Phe Leu Gln Ala Ser Tyr Tyr Val Ala Ile Glu Thr Gly
    370                 375                 380

Ile Asn Leu Arg Gly Ala Ile Gln Thr Lys Ile Tyr Asn Lys Ile Met
385                 390                 395                 400

His Met Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
            420                 425                 430

Phe Leu Cys Pro Asn Leu Trp Thr Met Pro Val Gln Ile Ile Val Gly
        435                 440                 445

Val Ile Leu Leu Tyr Tyr Ile Leu Gly Val Ser Ala Leu Ile Gly Ala
    450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu His Ser Asn Glu Arg Leu
                485                 490                 495

Lys Gln Thr Asn Glu Met Leu Arg Gly Met Lys Leu Leu Lys Leu Tyr
            500                 505                 510

Ala Trp Glu Ser Ile Phe Cys Ser Arg Val Glu Val Thr Arg Arg Lys
        515                 520                 525

Glu Met Thr Ser Leu Arg Ala Phe Ala Val Tyr Thr Ser Ile Ser Ile
    530                 535                 540

Phe Met Asn Thr Ala Ile Pro Ile Ala Ala Val Leu Ile Thr Phe Val
545                 550                 555                 560

Gly His Val Ser Phe Phe Lys Glu Ser Asp Leu Ser Pro Ser Val Ala
                565                 570                 575

Phe Ala Ser Leu Ser Leu Phe His Ile Leu Val Thr Pro Leu Phe Leu
            580                 585                 590

Leu Ser Ser Val Val Arg Ser Thr Val Lys Ala Leu Val Ser Val Gln
        595                 600                 605

Lys Leu Ser Glu Phe Leu Ser Ser Ala Glu Ile Arg Glu Glu Gln Cys
    610                 615                 620

Ala Pro Arg Glu Pro Ala Pro Gln Gly Gln Ala Gly Lys Tyr Gln Ala
625                 630                 635                 640

Val Pro Leu Lys Val Val Asn Arg Lys Arg Pro Ala Arg Glu Glu Val
                645                 650                 655
```

-continued

```
Arg Asp Leu Leu Gly Pro Leu Gln Arg Leu Ala Pro Ser Met Asp Gly
        660                 665                 670

Asp Ala Asp Asn Phe Cys Val Gln Ile Ile Gly Gly Phe Phe Thr Trp
        675                 680                 685

Thr Pro Asp Gly Ile Pro Thr Leu Ser Asn Ile Thr Ile Arg Ile Pro
        690                 695                 700

Arg Gly Gln Leu Thr Met Ile Val Gly Gln Val Gly Cys Gly Lys Ser
705                 710                 715                 720

Ser Leu Leu Leu Ala Thr Leu Gly Glu Met Gln Lys Val Ser Gly Ala
                725                 730                 735

Val Phe Trp Asn Ser Asn Leu Pro Asp Ser Glu Gly Arg Gly Pro Gln
                740                 745                 750

Gln Pro Arg Ala Gly Asp Ser Ser Trp Leu Gly Tyr Gln Glu Gln Arg
                755                 760                 765

Pro Arg Gly Tyr Ala Ser Gln Lys Pro Trp Leu Leu Asn Ala Thr Val
                770                 775                 780

Glu Glu Asn Ile Thr Phe Glu Ser Pro Phe Asn Pro Gln Arg Tyr Lys
785                 790                 795                 800

Met Val Ile Glu Ala Cys Ser Leu Gln Pro Asp Ile Asp Ile Leu Pro
                805                 810                 815

His Gly Asp Gln Thr Gln Ile Gly Glu Arg Gly Ile Asn Leu Ser Gly
                820                 825                 830

Gly Gln Arg Pro Asp Gln Cys Gly Pro Glu Pro Ser Thr Ser Arg Pro
                835                 840                 845

Met Phe Val Phe Leu Asp Asp Pro Phe Ser Ala Leu Asp Val His Leu
                850                 855                 860

Ser Asp His Leu Met Gln Ala Gly Ile Leu Glu Leu Leu Arg Asp Asp
865                 870                 875                 880

Lys Arg Thr Val Val Leu Val Thr His Lys Leu Gln Tyr Leu Pro His
                885                 890                 895

Ala Asp Trp Ile Ile Ala Met Lys Asp Gly Thr Ile Gln Arg Glu Gly
                900                 905                 910

Thr Leu Lys Asp Phe Gln Arg Ser Glu Cys Gln Leu Phe Glu His Trp
                915                 920                 925

Lys Thr Leu Met Asn Arg Gln Asp Gln Glu Leu Glu Lys Glu Thr Val
                930                 935                 940

Met Glu Arg Lys Ala Ser Glu Pro Ser Gln Gly Leu Pro Arg Ala Met
945                 950                 955                 960

Ser Ser Arg Asp Gly Leu Leu Leu Asp Glu Glu Glu Glu Glu Glu Glu
                965                 970                 975

Ala Ala Glu Ser Glu Glu Asp Asp Asn Leu Ser Ser Val Leu His Gln
                980                 985                 990

Arg Ala Lys Ile Pro Trp Arg Ala Cys Thr Lys Tyr Leu Ser Ser Ala
                995                 1000                1005

Gly Ile Leu Leu Leu Ser Leu Leu Val Phe Ser Gln Leu Leu Lys His
                1010                1015                1020

Met Val Leu Val Ala Ile Asp Tyr Trp Leu Ala Lys Trp Thr Asp Ser
1025                1030                1035                1040

Ala Leu Val Leu Ser Pro Ala Ala Arg Asn Cys Ser Leu Ser Gln Glu
                1045                1050                1055

Cys Asp Leu Asp Gln Ser Val Tyr Ala Met Val Phe Thr Leu Leu Cys
                1060                1065                1070

Ser Leu Gly Ile Val Leu Cys Leu Val Thr Ser Val Thr Val Glu Trp
```

-continued

```
            1075                1080                1085

Thr Gly Leu Lys Val Ala Lys Arg Leu His Arg Ser Leu Leu Asn Arg
        1090                1095                1100

Ile Ile Leu Ala Pro Met Arg Phe Phe Glu Thr Thr Pro Leu Gly Ser
1105                1110                1115                1120

Ile Leu Asn Arg Phe Ser Ser Asp Cys Asn Thr Ile Asp Gln His Ile
            1125                1130                1135

Pro Ser Thr Leu Glu Cys Leu Ser Arg Ser Thr Leu Leu Cys Val Ser
        1140                1145                1150

Ala Leu Thr Val Ile Ser Tyr Val Thr Pro Val Phe Leu Val Ala Leu
        1155                1160                1165

Leu Pro Leu Ala Val Val Cys Tyr Phe Ile Gln Lys Tyr Phe Arg Val
        1170                1175                1180

Ala Ser Arg Asp Leu Gln Gln Leu Asp Asp Thr Thr Gln Leu Pro Leu
1185                1190                1195                1200

Val Ser His Phe Ala Glu Thr Val Glu Gly Leu Thr Thr Ile Arg Ala
            1205                1210                1215

Phe Arg Tyr Glu Ala Arg Phe Gln Gln Lys Leu Leu Glu Tyr Thr Asp
        1220                1225                1230

Ser Asn Asn Ile Ala Ser Leu Phe Leu Thr Ala Ala Asn Arg Trp Leu
        1235                1240                1245

Glu Val Cys Met Glu Tyr Ile Gly Ala Cys Val Val Leu Ile Ala Ala
        1250                1255                1260

Ala Thr Ser Ile Ser Asn Ser Leu His Arg Glu Leu Ser Ala Gly Leu
1265                1270                1275                1280

Val Gly Leu Gly Leu Thr Tyr Ala Leu Met Ile Gly Ile Cys Gly Arg
            1285                1290                1295

Thr Ala Ser Gly Lys Ser Ser Phe Ser Leu Ala Phe Phe Arg Met Val
        1300                1305                1310

Asp Met Phe Glu Gly Arg Ile Ile Asp Gly Ile Asp Ile Ala Lys
            1315                1320                1325

Leu Pro Leu His Thr Leu Arg Ser Arg Leu Ser Ile Ile Leu Gln Asp
        1330                1335                1340

Pro Val Leu Phe Ser Gly Thr Ile Arg Phe Asn Leu Asp Pro Glu Lys
1345                1350                1355                1360

Lys Cys Ser Asp Ser Thr Leu Trp Glu Ala Leu Glu Ile Ala Gln Leu
            1365                1370                1375

Lys Leu Val Val Lys Ala Leu Pro Gly Gly Leu Asp Ala Ile Ile Thr
        1380                1385                1390

Glu Gly Gly Glu Asn Phe Ser Gln Gly Gln Arg Gln Leu Phe Cys Leu
        1395                1400                1405

Ala Arg Ala Phe Val Arg Lys Thr Ser Ile Phe Ile Met Asp Glu Ala
        1410                1415                1420

Thr Ala Ser Ile Asp Met Ala Thr Glu Asn Ile Leu Gln Lys Val Val
1425                1430                1435                1440

Met Thr Ala Phe Ala Asp Arg Thr Val Val Thr Ile Ala His Arg Val
                1445                1450                1455

His Thr Ile Leu Ser Ala Asp Leu Val Met Val Leu Lys Arg Gly Ala
            1460                1465                1470

Ile Leu Glu Phe Asp Lys Pro Glu Thr Leu Leu Ser Gln Lys Asp Ser
        1475                1480                1485

Val Phe Ala Ser Phe Val Arg Ala Asp Lys
        1490                1495
```

(2) INFORMATION FOR SEQ ID NO:30:

(i) SEQUENCE CHARACTERISTICS:
        (A) LENGTH: 2294 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:30:

```
GATGACCCCT TCTCAGCTTT GGATGTCCAT CTGAGTGACC ACCTGATGCA GGCCGGCATC        60

CTTGAGCTGC TCCGGGATGA CAAGAGGACA GTGGTCTTGG TGACCCACAA GCTACAGTAT       120

CTGCCTCATG CAGACTGGAT CATTGCCATG AAGGATGGGA CCATTCAGAG GGAAGGGACG       180

CTCAAGGACT TCCAGAGGTC CGAGTGCCAG CTCTTTGAGC ACTGGAAGAC CCTCATGAAC       240

CGGCAGGACC AAGAGCTGGA GAAGGAGACA GTCATGGAGA GGAAAGCCTC AGAGCCATCT       300

CAGGGCCTGC CCCGTGCCAT GTCCTCCAGA GACGGCCTTC TGCTGGATGA GGAAGAGGAG       360

GAAGAGGAGG CAGCCGAAAG CGAGGAAGAT GACAACTTAT CTTCAGTGCT GCATCAGCGA       420

GCTAAGATCC CCTGGCGAGC CTGCACTAAG TATCTGTCCT CTGCTGGCAT TCTGCTCCTG       480

TCCCTGCTTG TCTTCTCCCA GCTGCTCAAG CACATGGTCT TGGTGGCCAT TGATTATTGG       540

CTGGCCAAGT GGACGGACAG TGCCCTGGTC CTGAGCCCCG CTGCCAGGAA CTGTTCGCTC       600

AGCCAGGAAT GTGACCTGGA CCAGTCTGTC TATGCCATGG TATTCACCTT GCTCTGCAGC       660

CTGGGTATCG TGCTGTGCCT GGTCACCTCT GTCACTGTGG AGTGGACGGG ACTGAAGGTG       720

GCCAAGAGGC TACACCGCAG CCTGCTCAAC CGCATCATCC TGGCCCCCAT GAGGTTCTTT       780

GAGACCACAC CCCTCGGGAG TATCCTGAAC AGATTTTCAT CCGACTGTAA CACCATTGAC       840

CAGCACATCC CATCCACGCT GGAGTGTCTG AGCCGGTCCA CCCTGCTGTG TGTCTCCGCC       900

CTGACTGTCA TCTCCTATGT CACACCCGTG TTCCTCGTGG CCCTCTTACC CCTAGCTGTT       960

GTGTGCTACT TCATTCAGAA GTACTTCCGA GTGGCATCCA GGGACCTGCA GCAGCTGGAC      1020

GACACGACGC AGCTCCCGCT CGTCTCACAC TTTGCTGAAA CTGTGGAGGG ACTCACCACC      1080

ATCCGTGCCT TCAGGTACGA GGCCCGGTTC CAGCAGAAGC TTCTAGAATA TACCGACTCC      1140

AACAACATCG CCTCCCTCTT CCTCACGGCA GCCAACAGAT GGCTGGAAGT CTGCATGGAG      1200

TACATCGGAG CGTGCGTGGT ACTCATTGCG GCTGCCACCT CCATCTCCAA CTCCCTGCAC      1260

AGGGAACTTT CTGCTGGCCT GGTGGGCCTG GGCCTCACCT ATGCCTTGAT GGTCTCCAAC      1320

TACCTCAACT GGATGGTGAG GAACCTGGCG GACATGGAGA TCCAGCTGGG GGCTGTGAAG      1380

AGGATCCACG CACTCCTGAA AACCGAGGCG GAGAGCTATG AGGGGCTCCT GGCGCCGTCG      1440

TTGATCCCCA GAACTGGCC AGACCAAGGG AAGATCCAAA TTCAGAACCT GAGCGTGCGC      1500

TATGACAGCT CCCTGAAGCC AGTGCTGAAG CATGTCAACA CCCTCATCTC CCCGGGGCAG      1560

AAGATCGGGA TCTGCGGCCG CACAGGCAGC GGGAAGTCCT CCTTCTCCCT GGCCTTTTTC      1620

CGAATGGTGG ACATGTTTGA AGGACGCATC ATCATTGATG GCATCGACAT CGCCAAGCTG      1680

CCACTTCACA CGCTGCGCTC ACGCCTGTCC ATCATCCTAC AGGACCCCGT CCTCTTCAGC      1740

GGCACGATCA GATTCAACCT GGACCCCGAG AAGAAATGCT CAGACAGCAC ACTGTGGGAG      1800

GCCCTGGAGA TCGCCCAGCT GAAGCTGGTA GTGAAGGCAC TGCCAGGAGG CCTAGATGCC      1860
```

```
ATCATCACAG AAGGAGGGGA GAATTTTAGC CAGGGCCAGA GGCAGCTGTT CTGCCTGGCC    1920

CGGGCCTTCG TGAGGAAGAC CAGCATCTTC ATCATGGATG AAGCAACCGC CTCCATCGAC    1980

ATGGCTACGG AGAACATCCT CCAGAAGGTG GTGATGACAG CCTTCGCAGA CCGCACGGTG    2040

GTCACCATCG CGCATCGTGT GCACACCATC CTGAGTGCAG ACCTGGTGAT GGTCCTCAAG    2100

AGGGGTGCTA TCCTGGAGTT TGACAAGCCA GAGACGCTCC TCAGCCAGAA GGACAGCGTG    2160

TTCGCCTCCT TTGTCCGTGC GGACAAGTGA CTTACCGGAG CCAAAGTGCC ACCCCGCGCC    2220

TCGCTTGCTT GCCTAGGATT TCTAACTGCA AATCACTTGT AAATAAATTA ATTCTTTGCT    2280

AAAAAAAAAA AAAA                                                      2294

(2) INFORMATION FOR SEQ ID NO:31:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:31:

CCATGCCTGG TGGCTGAGCC CAGCCCAGCC CCCAGCACCA TCGCTGATCC CAAAGAACTG      60

GCCAGACCAA GGGAAGATCC AGATCCAGAA CCTGAGCGTG CGCTACGACA GCTCCCTGAA     120

GCCGGTGCTG AAGCACGTCA ATGCCCTCAT CTCCCCTGGA CAGAAGGTCA GTGCACGGGC     180

CCAACCCAAT GCTGC                                                     195

(2) INFORMATION FOR SEQ ID NO:32:

(i) SEQUENCE CHARACTERISTICS:
        (A) LENGTH: 2454 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:32:

CTGCTCTCTG CAGCCAGACA TCGACATCCT GCCCCATGGA GACCAGACCC AGATTGGGGA      60

ACGGGGCATC AACCTGTCTG GTGGTCAACG CCAGCGAATC AGTGTGGCCC GAGCCCTCTA     120

CCAGCACGCC AACGTTGTCT TCTTGGATGA CCCCTTCTCA GCTCTGGATA TCCATCTGAG     180

TGACCACTTA ATGCAGGCCG GCATCCTTGA GCTGCTCCGG GACGACAAGA GGACAGTGGT     240

CTTAGTGACC CACAAGCTAC AGTACCTGCC CCATGCAGAC TGGATCATTG CCATGAAGGA     300

TGGCACCATC CAGAGGGAGG GTACCCTCAA GGACTTCCAG AGGTCTGAAT GCCAGCTCTT     360

TGAGCACTGG AAGACCCTCA TGAACCGACA GGACCAAGAG CTGGAGAAGG AGACTGTCAC     420

AGAGAGAAAA GCCACAGAGC CACCCCAGGG CCTATCTCGT GCCATGTCCT CGAGGGATGG     480

CCTTCTGCAG GATGAGGAAG AGGAGGAAGA GGAGGCAGCT GAGAGCGAGG AGGATGACAA     540

CCTGTCGTCC ATGCTGCACC AGCGTGCTGA GATCCCATGG CGAGCCTGCG CCAAGTACCT     600
```

```
GTCCTCCGCC GGCATCCTGC TCCTGTCGTT GCTGGTCTTC TCACAGCTGC TCAAGCACAT      660

GGTCCTGGTG GCCATCGACT ACTGGCTGGC CAAGTGGACC GACAGCGCCC TGACCCTGAC      720

CCCTGCAGCC AGGAACTGCT CCCTCAGCCA GGAGTGCACC CTCGACCAGA CTGTCTATGC      780

CATGGTGTTC ACGGTGCTCT GCAGCCTGGG CATTGTGCTG TGCCTCGTCA CGTCTGTCAC      840

TGTGGAGTGG ACAGGGCTGA AGGTGGCCAA GAGACTGCAC CGCAGCCTGC TAAACCGGAT      900

CATCCTAGCC CCCATGAGGT TTTTTGAGAC CACTCCCCTT GGGAGCATCC TGAACAGATT      960

TTCATCTGAC TGTAACACCA TCGACCAGCA CATCCCATCC ACGCTGGAGT GCCTGAGCCG     1020

CTCCACCCTG CTCTGTGTCT CAGCCCTGGC CGTCATCTCC TATGTCACAC CTGTGTTCCT     1080

CGTGGCCCTC CTTCCCCTGG CCATCGTGTG CTACTTCATC CAGAAGTACT CCGGGTGGC      1140

GTCCAGGGAC CTGCAGCAGC TGGATGACAC CACCCAGCTT CCACTTCTCT CACACTTTGC     1200

CGAAACCGTA GAAGGACTCA CCACCATCCG GGCCTTCAGG TATGAGGCCC GGTTCCAGCA     1260

GAAGCTTCTC GAATACACAG ACTCCAACAA CATTGCTTCC CTCTTCCTCA CAGCTGCCAA     1320

CAGATGGCTG GAAGTCCGAA TGGAGTACAT CGGTGCATGT GTGGTGCTCA TCGCAGCGGT     1380

GACCTCCATC TCCAACTCCC TGCACAGGGA GCTCTCTGCT GGCCTGGTGG GCCTGGGCCT     1440

TACCTACGCC CTAATGGTCT CCAACTACCT CAACTGGATG GTGAGGAACC TGCAGACAT      1500

GGAGCTCCAG CTGGGGGCTG TGAAGCGCAT CCATGGGCTC CTGAAAACCG AGGCAGAGAG     1560

CTACGAGGGA CTCCTGGCAC CATCGCTGAT CCCAAAGAAC TGGCCAGACC AAGGGAAGAT     1620

CCAGATCCAG AACCTGAGCG TGCGCTACGA CAGCTCCCTG AAGCCGGTGC TGAAGCACGT     1680

CAATGCCCTC ATCTCCCCTG ACAGAAGAT CGGGATCTGC GGCCGCACCG GCAGTGGGAA      1740

GTCCTCCTTC TCTCTTGCCT TCTTCCGCAT GGTGGACACG TTCGAAGGGC ACATCATCAT     1800

TGATGGCATT GACATCGCCA AACTGCCGCT GCACACCCTG CGCTCACGCC TCTCCATCAT     1860

CCTGCAGGAC CCCGTCCTCT TCAGCGGCAC CATCCGATTT AACCTGGACC CTGAGAGGAA     1920

GTGCTCAGAT AGCACACTGT GGGAGGCCCT GGAAATCGCC CAGCTGAAGC TGGTGGTGAA     1980

GGCACTGCCA GGAGGCCTCG ATGCCATCAT CACAGAAGGC GGGGAGAATT TCAGCCAGGG     2040

ACAGAGGCAG CTGTTCTGCC TGGCCCGGGC CTTCGTGAGG AAGACCAGCA TCTTCATCAT     2100

GGACGAGGCC ACGGCTTCCA TTGACATGGC CACGGAAAAC ATCCTCCAAA AGGTGGTGAT     2160

GACAGCCTTC GCAGACCGCA CTGTGGTCAC CATCGCGCAT CGAGTGCACA CCATCCTGAG     2220

TGCAGACCTG GTGATCGTCC TGAAGCGGGG TGCCATCCTT GAGTTCGATA AGCCAGAGAA     2280

GCTGCTCAGC CGGAAGGACA GCGTCTTCGC CTCCTTCGTC CGTGCAGACA AGTGACCTGC     2340

CAGAGCCCAA GTGCCATCCC ACATTCGGAC CCTGCCCATA CCCCTGCCTG GGTTTTCTAA     2400

CTGTAAATCA CTTGTAAATA AATAGATTTG ATTATTTCCT AAAAAAAAAA AAAA           2454
```

(2) INFORMATION FOR SEQ ID NO:33:

(i) SEQUENCE CHARACTERISTICS:
        (A) LENGTH: 20 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:33:

Pro Leu Ala Phe Ser Gly Thr Glu Xaa His Ser Ala Ala Tyr Arg Val

```
                 1               5              10             15
Asp Gln Gly Val
            20

(2) INFORMATION FOR SEQ ID NO:34:

(i) SEQUENCE CHARACTERISTICS:
        (A) LENGTH: 24 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:34:

Pro Leu Ala Phe Xaa Gly Thr Glu Asn His Ser Ala Ala Tyr Arg Val
  1               5              10                  15
Asp Gln Gly Val Leu Asn Asn Gly
            20

(2) INFORMATION FOR SEQ ID NO:35:

(i) SEQUENCE CHARACTERISTICS:
        (A) LENGTH:  19 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:35:

Pro Leu Ala Phe Ser Gly Thr Glu Xaa His Ser Ala Ala Tyr Arg Val
  1               5              10                  15
Asp Gln Gly (2) INFORMATION FOR SEQ ID NO:36:

(i) SEQUENCE CHARACTERISTICS:
        (A) LENGTH:  20 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:36:

Xaa Leu Ala Phe Cys Gly Thr Glu Xaa His Ser Ala Ala Tyr Arg Val
  1               5              10                  15
Asp Gln Gly Val
            20

(2) INFORMATION FOR SEQ ID NO:37:

(i) SEQUENCE CHARACTERISTICS:
        (A) LENGTH:  30 amino acids
        (B) TYPE: amino acid
        (D) TOPOLOGY: linear (ii) MOLECULE TYPE: protein
```

(iii) HYPOTHETICAL: NO (iv) ANTI-SENSE: NO (xi) SEQUENCE DESCRIPTION: SEQ ID NO:37:

Pro Leu Ala Phe Cys Gly Thr Glu Xaa His Ser Ala Ala Tyr Arg Val
1               5                   10                  15

Asp Gln Gly Val Leu Asn Asn Gly Cys Phe Val Asp Ser Tyr
            20                  25                  30

(2) INFORMATION FOR SEQ ID NO:38:

(i) SEQUENCE CHARACTERISTICS:
        (A) LENGTH:  25 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:38:

Pro Leu Ala Phe Cys Gly Thr Glu Xaa His Ser Ala Ala Tyr Arg Val
1               5                   10                  15

Asp Gln Gly Val Leu Asn Asn Gly Pro
            20                  25

(2) INFORMATION FOR SEQ ID NO:39:

(i) SEQUENCE CHARACTERISTICS:
        (A) LENGTH:  25 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:39:

Pro Leu Ala Phe Cys Gly Thr Glu Xaa His Ser Ala Ala Tyr Arg Val
1               5                   10                  15

Asp Gln Gly Val Leu Asn Asn Gly Cys
            20                  25

(2) INFORMATION FOR SEQ ID NO:40:

(i) SEQUENCE CHARACTERISTICS:
        (A) LENGTH:  8 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:40:

Phe Glu Gly His Ile Arg Phe Asn
1               5

(2) INFORMATION FOR SEQ ID NO:41:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:41:

TTCGAAGGGC ACATCCGATT TAAC                                         24

(2) INFORMATION FOR SEQ ID NO:42:

(i) SEQUENCE CHARACTERISTICS:
           (A) LENGTH:  5 amino acids
           (B) TYPE: amino acid
           (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:42:

Phe Glu Asp Leu Thr
 1               5

(2) INFORMATION FOR SEQ ID NO:43:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:43:

TTCGAAGATT TAACC                                                   15

(2) INFORMATION FOR SEQ ID NO:44:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:44:

TTCGAAGATT TAACC                                                   15

(2) INFORMATION FOR SEQ ID NO:45:

(i) SEQUENCE CHARACTERISTICS:
           (A) LENGTH: 4 base pairs
           (B) TYPE: nucleic acid

```
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:45:

GATC                                                                    4

(2) INFORMATION FOR SEQ ID NO:46:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:46:

CCATCCRGTG AGCC                                                         14

(2) INFORMATION FOR SEQ ID NO:47:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:47:

CAGCCCRGCC CCCA                                                         14

(2) INFORMATION FOR SEQ ID NO:48:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:48:

CCGGCCCCCA GCACCATCGC TGATCCCAAA GAACTGGCCA GACCAA                      46

(2) INFORMATION FOR SEQ ID NO:49:

(i) SEQUENCE CHARACTERISTICS:
        (A) LENGTH:  12 amino acids
        (B) TYPE: amino acid
        (D) TOPOLOGY: linear (ii) MOLECULE TYPE: protein
```

```
    (iii) HYPOTHETICAL: NO (iv) ANTI-SENSE: NO (xi) SEQUENCE DESCRIPTION: SEQ ID NO:49:

Ala Pro Ser Leu Ile Pro Lys Asn Trp Pro Asp Gln
 1               5                   10
```

NUCLEIC ACID AND AMINO ACID SEQUENCES FOR MAMMALIAN SULFONYLUREA RECEPTOR

REFERENCE TO RELATED APPLICATIONS

This application is a divisional of U.S. patent application Ser. No. 08/404,531, filed Mar. 15, 1995, now U.S. Pat. No. 5,863,724, which is a continuation-in-part of U.S. patent application Ser. No. 08/226,972, filed Apr. 13, 1994, now abandoned, the disclosure of which is hereby incorporated by reference in its entirety.

REFERENCE TO GOVERNMENT GRANTS

This work was supported in part by research grants from the National Institutes of Health, grant number NIH R01DK41898 and R01DK44311. The United States Government may have certain rights in this invention.

BACKGROUND OF THE INVENTION

Sulfonylureas are oral hypoglycemics widely used in the treatment of Non-Insulin Dependent Diabetes Mellitus (NIDDM). They enter the bloodstream, bind with high affinity to a pancreatic β-cell plasma membrane protein termed the sulfonylurea receptor, and stimulate insulin release. The mechanism of stimulation is thought to be through inhibition of an ATP-sensitive K+ channel ($K_{ATP}$), a key protein which sets the β-cell resting membrane potential (Ashcroft, et al. *Cell. Signal.* 1990, 2, 197–214, all references cited herein are incorporated by reference in their entirety). A reduction in potassium outflow causes depolarization of the plasma membrane, activation of L-type voltage-dependent calcium channels (VDCCs), and increased cytosolic calcium. This triggers insulin release by as yet unknown mechanisms (Rajan, et al. *Diabetes Care* 1990, 13, 340–363). In NIDDM patients on sulfonylureas, the consequent reduction in blood glucose to more normal levels is thought to be critical in controlling the disease (Gerich, J. E. *New Engl. J. Med.* 1989, 321, 1231–1245).

The biochemistry of the sulfonylurea receptor (SUR) (Ashcroft et al *Biochem. Biophys Acta* 1992, 1175, 45–49 and Panten et al. *Horm. Metab. Res.* 1992, 24, 549–554) is consistent with the electrophysiology of the β-cell $K_{ATP}$ channel. The endogenous regulators of channel activity include cytosolic nucleotides (ATP and Mg-ADP) and possibly phosphorylation. In the absence of cytosolic nucleotides, sulfonylureas weakly inhibit channel activity (Schwanstecher et al. *Br. J. Pharmacol* 1992, 107, 87–94). When channels are activated by Mg-ADP, inhibition by ATP is strongly promoted by the presence of sulfonylureas. These results are interpreted as evidence that simultaneous occupancy of two nucleotide binding sites is required for effective channel inhibition by the sulfonylureas. The reported allosteric interactions correlate well with evidence that the brain receptor has two nucleotide binding sites (de Weille, et al. *J. Biol. Chem* 1992, 267, 4557–4563) physically located on the same polypeptide chain as the sulfonylurea binding site (Bernardi et al. *Biochemistry* 1992, 31, 6328–6332). One binding site appears to be specific for ATP, and is proposed to be the same site at which micromolar concentrations of ATP inhibit the $K_{ATP}$ channel. A second site has high affinity for Mg-ADP, with occupancy at this site promoting channel opening. Absolute concentrations of ATP and ADP in the cell are thought to regulate channel activity in a straightforward fashion (Hopkins et al. *J. Membrane Biol.* 1992, 129, 287–295). High ATP concentrations as a result of high serum glucose levels close the channel, stimulating insulin secretion. Reduced glucose levels increase intracellular ADP concentrations, and thereby increase the open channel probability, and decrease insulin secretion.

Although sulfonylureas, particularly tolbutamide and more potent second generation drugs like glyburide and glipizide, are considered to be relatively specific inhibitors of the $K_{ATP}$ channel, the exact relationship between the sulfonylurea receptor and the $K_{ATP}$ channel is not clear (Nichols et al. *Am. J. Physiol.* 1991, 261, H1675–H1686, Takano et al. *Progress in Neurobiology* 1993, 41, 21–30, and Edwards et al. *Annu. Rev. Pharmacol. Toxicol.* 1993, 33, 597–637). In the insulin-secreting CRI-G1 cell line, the addition of glyburide, or tolbutamide to inside-out plasma membrane patches inhibits the $K_{ATP}$ channel (Khan et al. *Proc. R. Soc. Lond. B.* 1993, 253, 225–231), intimating direct interactions between sulfonylureas and the channel protein. In another insulin secreting cell line, CRI-G11 cells, however, the loss of sulfonylurea binding sites with the retention of $K_{ATP}$ activity suggests these two activities may uncouple and reside on separate, transiently bound subunits (Khan et al. *Proc. R. Soc. Lond. B.* 1993, 253, 225–231). Similarly, in other cell and tissue types, sulfonylurea binding and channel activity may be uncoupled (Ashford et al *Br. J. Pharmac.* 1990, 101, 531–540). A technique is not currently available to assess whether $K_{ATP}$ activity resides within the same polypeptide containing the putative nucleotide and sulfonylurea binding sites, or on separate loosely, or tightly bound subunits.

A previous attempt to purify the receptor from hamster insulin-secreting tumor (HIT) cells was limited by the low abundance of the receptor and the presence of a more abundant co-purifying protein. Aguilar-Bryan, L., et al., *JBC*, 1990, 265, 8218.

The sulfonylurea receptor is the target for drugs used in the treatment of type II diabetes (non-insulin diabetes mellitus). This association has suggested it plays a role in the regulation of insulin secretion by glucose and makes the sulfonylurea receptor a potential diabetes candidate gene.

Persistent hyperinsulinemic hypoglycemia of infancy (PHHI) is an autosomal recessive disorder of glucose homeostasis characterized by unregulated secretion of insulin and profound hypoglycemia. A. Aynsley-Green et al., *Arch. Dis. Child.* 1981, 56, 496. The pathophysiology of this disease remains obscure, but in vitro studies suggest a defect of glucose-regulated insulin secretion in pancreatic islet β-cells. Aynsley-Green et al., supra., N. Kaiser et al., *Diabetologia* 1990, 33, 482. The incidence of PHHI has been estimated at 1/50,000 live births in a randomly mating population. G. J. Bruining, *Curr. Opin. Pediatr.* 1990, 2, 758. However, in a Saudi Arabian population in which 51% of births occurred to parents who were first or second cousins, the incidence has been established as 1/2675 live births. P. M. Mathew et al., *Clin. Pediatr.* 1988, 27, 148. Recently, the PHHI gene was assigned to chromosome 11p1415.1 by linkage analysis. B. Glaser et al., *Nature Genet.* 1994, 7, 185 and P. M. Thomas, G. J. Cote, D. M. Hallman, P. M. Mathew, *Am. J. Hum. Genet.* 1995, 56, 416–421. Candidate genes for this disorder include those involved in the β-cell glucose sensing mechanism and insulin secretion. Localization of PHHI to chromosome 11p excluded previously mapped genes involved in β-cell function. Considered as a candidate was the newly cloned high-affinity SUR gene, a member of the ATP-binding cassette superfamily, and a putative subunit of the modulator of insulin secretion, the β-cell ATP-sensitive potassium channel ($K_{ATP}$)- S. J. Ashcroft and F. M. Ashcroft, *Biochimica* et *Biophysica Acta,* 1992, 1175, 45; U.

Panten, M. Schwanstecher, and C. Schwanstecher, *Horm. Metab. Res.* 1992, 24, 549. The methods of the present invention map the sulfonylurea receptor to the same chromosomal location as PHHI and provide evidence that mutations in the sulfonylurea receptor are the cause of PHHI.

Accordingly, there remains a need to identify sulfonylurea receptor and sequences encoding sulfonylurea receptor which will provide:

1. a correlation between sulfonylurea receptor and one or more forms of diabetes,
2. a sequence to purify human sulfonylurea receptors,
3. an isolated sulfonylurea receptor, prepared by recombinant methods,
4. polyclonal and monoclonal antibodies and methods of preparing the same against sulfonylurea receptor,
5. information as to whether this receptor-ion channel family involves multi-subunits within each channel for channel activity,
6. gene therapy such that sequences which encode mutant sulfonylurea receptors are replaced by wild type sulfonylurea receptor sequences,
7. a method of screening to identify drugs which react with and bind to the sulfonylurea receptor,
8. non-human transgenic animals to study diabetes and PHHI, and the physiologic effects of varying levels of sulfonylurea receptor, by using an inducible promoter to regulate the expression of the sulfonylurea receptor, for example, and
9. probes, including PCR probes, for diagnosing conditions associated with the expression of a specific sulfonylurea receptor allele.

The present invention reveals that the sequence encoding the mammalian sulfonylurea receptor maps to the sequence encoding persistent hyperinsulinemic hypoglycemia of infancy.

SUMMARY OF THE INVENTION

The present invention provides sequences encoding a sulfonylurea receptor. Nucleic acid sequences, SEQ ID NOS: 4, 5, 7, and 8 are cDNA sequences to which the present invention is directed. SEQ ID NOS: 4, 5, 7, and 8 are rodent sequences (SEQ ID NOS: 4 and 5—rat, SEQ ID NOS: 7 and 8-hamster) encoding sulfonylurea receptor which functionally bind sulfonylurea. SEQ ID NOS: 1 and 2 are human sequences which encode sulfonylurea receptor. SEQ ID NOS: 2, 5, and 8 set forth DNA sequences translated into amino acid sequences, which set forth below the DNA sequence.

A further aspect of the present invention provides sulfonylurea receptor polypeptides and/or proteins. SEQ ID NOS:1, 3, 27, 28, 29 are novel polypeptides of the invention produced from nucleotide sequences encoding rat (SEQ ID NOS: 6, 27and 28), hamster (SEQ ID NOS: 9 and 29), and human (SEQ ID NOS: 1 and 3) sulfonylurea receptor, respectively. Also within the scope of the present invention is a purified sulfonylurea receptor.

The present invention also provides nucleic acid sequences encoding a sulfonylurea receptor, expression vectors comprising a nucleic acid sequence encoding a sulfonylurea receptor, transformed host cells capable of expressing a nucleic acid sequence encoding a sulfonylurea receptor, cell cultures capable of expressing a sulfonylurea receptor, and protein preparations comprising a sulfonylurea receptor.

A method of detecting persistent hyperinsulinemic hypoglycemia of infancy comprising obtaining a sample comprising patient nucleic acids from a patient tissue sample; amplifying sulfonylurea receptor specific nucleic acids from said patient nucleic acids to produce a test fragment; obtaining a sample comprising control nucleic acids from a control tissue sample; amplifying control nucleic acids encoding wild type sulfonylurea receptor to produce a control fragment; comparing the test fragment with the control fragment to detect the presence of a sequence difference in the test fragment, wherein a difference in said test fragment indicates persistent hyperinsulinemic hypoglycemia of infancy is also an embodiment of the present invention.

Other methods of the present invention include a method of detecting persistent hyperinsulinemic hypoglycemia of infancy comprising obtaining a sample comprising patient mRNA from a patient tissue sample; reverse transcribing said mRNA into cDNA to produce patient cDNA; amplifying sulfonylurea receptor specific cDNA from said patient cDNA to produce amplified patient cDNA; obtaining a sample comprising control nucleic acids from a control tissue sample; amplifying control DNA encoding wild type sulfonylurea receptor to produce control cDNA; digesting said test fragment and said control fragment with a selected endonuclease; and comparing the test fragment to the control fragment, wherein said test fragment indicates persistent hyperinsulinemic hypoglycemia of infancy.

Another embodiment of the present invention is a diagnostic kit for detecting persistent hyperinsulinemic hypoglycemia of infancy comprising in one or more containers a pair of primers, wherein one primer within said pair is complementary to a region of the sulfonylurea receptor, wherein one of said pair of primers is selected from the group consisting of SEQ ID NOS: 12–20, a probe specific to the amplified product, and a means for visualizing amplified DNA, such as and not limited to fluorescent stain, $^{32}P$, and biotin, and optionally including one or more size markers, positive and negative controls, and restriction endonucleases.

Still another embodiment of the present invention includes the primer sequences identified in SEQ ID NOS: 12–20.

BRIEF DESCRIPTION OF THE DRAWINGS

FIGS. 1A and 1B display characteristics of the purified HIT cell receptor. The radiolabeled receptor (lanes 1 and 3) cleaved with endoglycosidase F/N-glycosidase F (endo F), increases the mobility of the protein by approximately 3 kDa (lane 2). Subsequent partial V8 protease digestion (lanes 4 and 6) yielded radiolabeled fragments that also shift mobility with endo F treatment (lane 5). Each of these species has the same N-terminal sequence (left side of figure), except that receptor deglycosylation results in an Asp at residue 9. The amino acid sequences set forth in FIG. 1 are SEQ ID NOS: 33, 34, 35, 36, 37, 38, and 39.

Multiple antigenic peptides (MAPS) were synthesized (Posnett et al. *J. Biol. Chem.* 1988 263:1719–1725) and polyclonal antibodies generated in rabbits produced by standard methods (Antibodies: A Laboratory Manual Cold Spring Harbor Laboratory 1988). Interdermal injections of 1 mg of antigen were spaced 2–3 weeks apart, and contained complete, or incomplete Freund's adjuvant.

Figure 3:

FIG. 3 is a northern blot of total RNA from α- and β-cell lines hybridized with a 2.2 kb EcoRI-XhoI fragment of the sulfonylurea receptor. Approximately 10 μg of RNA from (A) αTC-6 cells, (B) HIT cells, (C) RIN cells and (D) mouse liver was analyzed using standard procedures (Ausubel et al. *Current Protocols in Mol. Biol.* 1994). The estimated size of the major component is approximately 5000 nucleotides.

Figure 4:
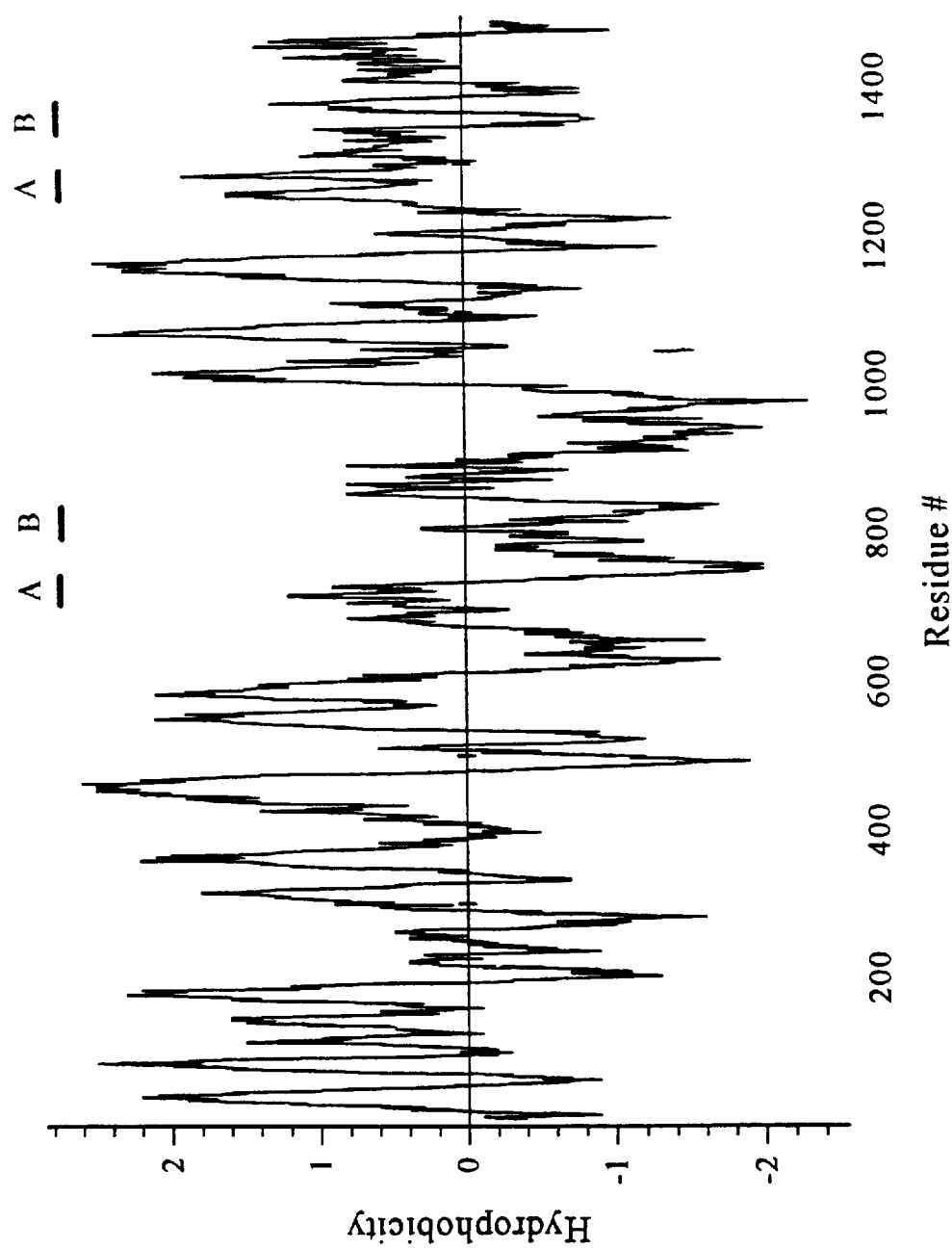

FIG. 4 displays a hydrophobicity profile of the Rat Sulfonylurea receptor. Hydrophobicity values were determined according to Kyte and Doolittle (Kyte et al. *J. Mol. Biol.* 1982 157:105–132) for 11-residue peptides and are plotted versus the amino acid number. The bars marked A and B are over the Walker A and B consensus sequences (Walker et al. *EMBO Jour.* 1982 1:945–951).

Figure 5:
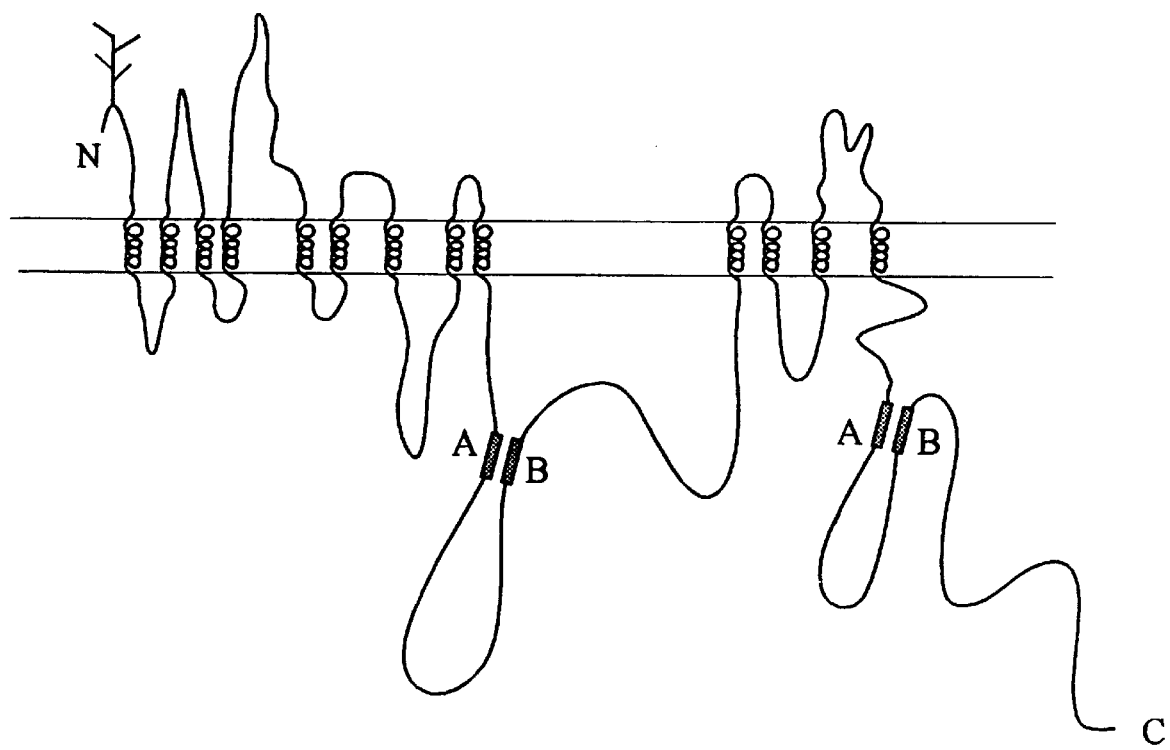

FIG. 5 shows a schematic model of the high affinity sulfonylurea receptor. The Walker A and B sites are marked within the two nucleotide binding folds. Based on the hydrophobicity and hydrophobic moment data there are nine transmembrane spanning domains before the first nucleotide binding fold and four transmembrane spanning domains between the two folds. The branched structure at the N-terminus of the mature receptor symbolizes glycosylation.

Figure 6A:
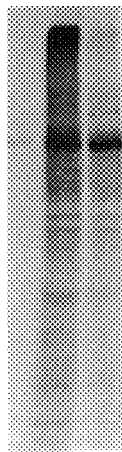

FIG. 6A reveals the results of in vitro translation of mRNA transcribed from the rat sulfonylurea cDNA. The cDNA was subcloned into pGEM4 (Promega, Inc., Madison, Wis.) and transcribed using the SP6 promoter and SP6 RNA polymerase following the manufacturer's directions. RNA was translated in rabbit reticulocyte lysate (Promega, Inc.) following the manufacturer's recommendations for $^{35}$S-methionine. Lane 1 is the HIT cell photolabeled receptor as a marker, lane 2 is the in vitro translation product resulting from addition of receptor mRNA and lane 3 is the result of no added RNA. The arrow marks the 140 kDa protein.

Figure 6B:
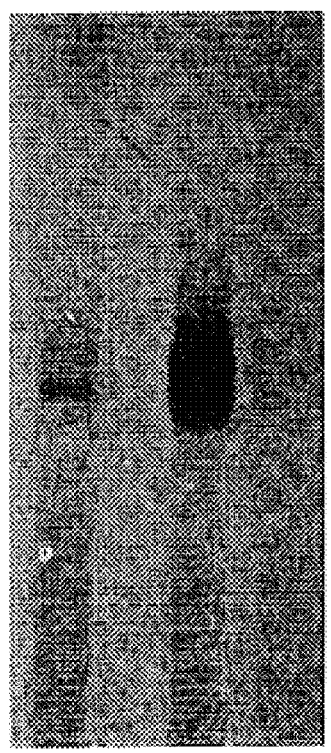

FIG. 6B displays a gel of the results of immunoprecipitation of the RIN cell sulfonylurea receptors with polyclonal antibodies directed against a nucleotide binding fold domain (NBF). Lane 1: 140 and 150 kDa receptors from soluble RIN cell membrane proteins, lane 2: immunoprecipitation with preimmune serum, lane 3: immune serum from rabbit immunized with NBF2, lane 4: immune serum+NBF2 fusion protein. Sulfonylurea receptor cDNA regions encoding the NBF2 domain were subcloned in frame into pMALc and expression of the proteins fused with maltose binding protein induced in *E. coli*. Fusion proteins were purified by electrophoresis and electroelution, and 200 μg amounts, with complete, or incomplete Freund's adjuvant, injected intradermally into rabbits using a standard 2–3 week regimen of bleeding and boosting.

Figure 7:
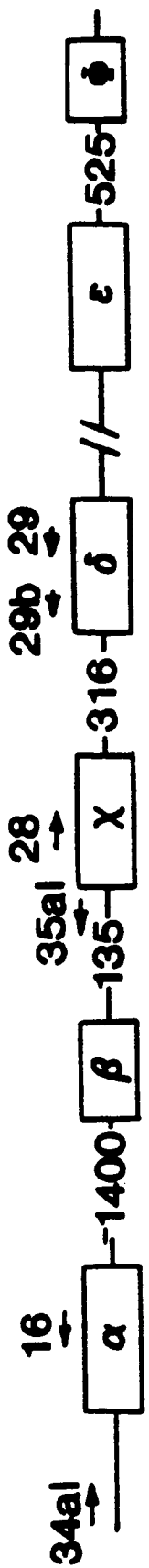

FIG. 7 displays the genomic organization and of the human sulfonylurea receptor (SUR) homologue in the second nucleotide binding fragment region (NBF-2). The sequence encoding NBF-2 is located within SEQ ID NO: 1, nucleic acid positions 524 to 1048. Solid rectangles represent exons which are labeled α-φ for identification. The numbers between rectangles represent intronic sizes. Primers used in mutational analysis are diagrammed and listed in the arrows as Primer 17=SEQ ID NO: 13; Primer 34a1=SEQ ID NO: 17; Primer 16=SEQ ID NO: 12; Primer 35 al=SEQ ID NO: 18; Primer 28 =SEQ ID NO: 14; Primer 29b=SEQ ID NO: 16; Primer 29=SEQ ID NO: 15.

Figures 8A, 8B:
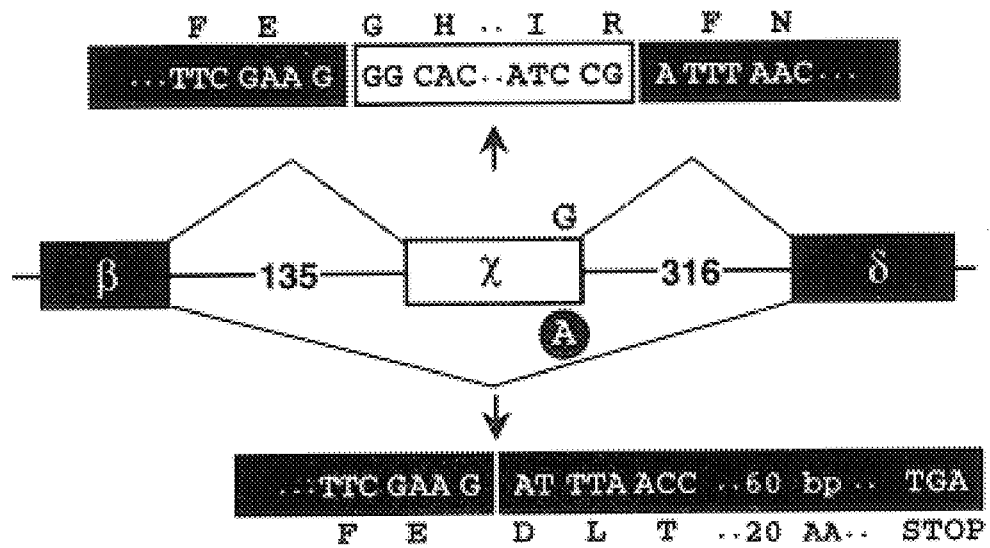
Figure 8C:
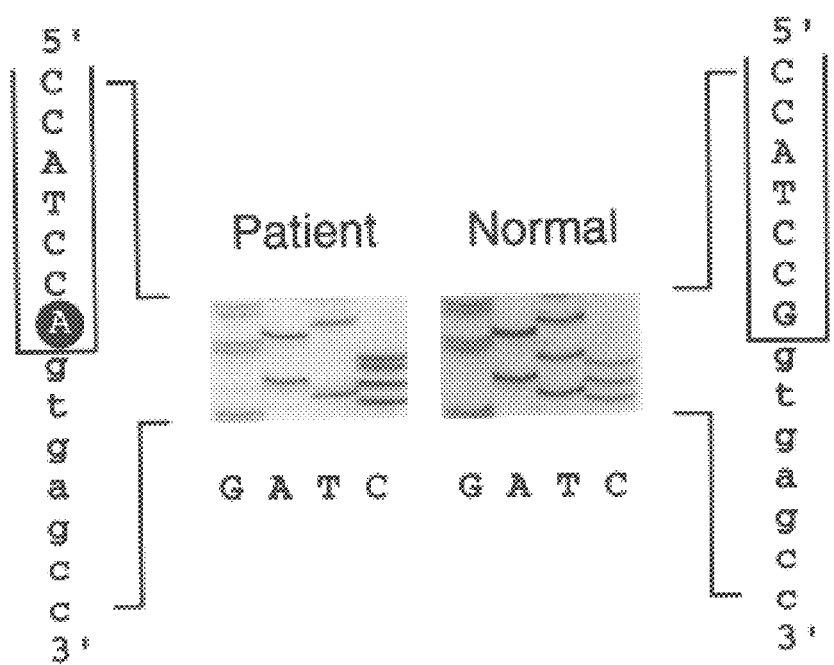
Figure 8D:
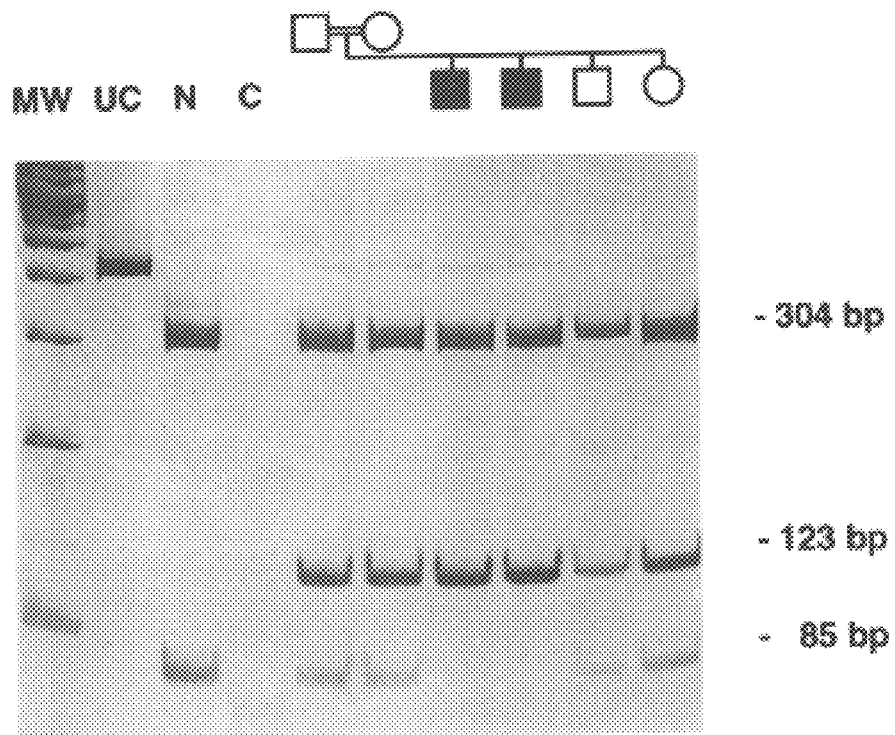

FIG. 8A–D display the exon mutation in the SUR NBF-2. FIG. 8A is a schematic representation of NBF-2 exons β, X, δ illustrating the normal (upper) and mutant (lower) RNA splicing patterns SEQ ID NOS: 40, 41, 42, and 43. FIG. 8B displays the sequence of a pancreatic cDNA product, and corresponding amino acid sequence, SEQ ID NOS: 44 and 45, respectively, from an affected child of Family 6, demonstrating the exon skipping event. Skipping of exon X results in a 109 bp deletion in the mRNA transcript, a frame shift and inclusion of a premature stop codon. Single upper case letters represent amino acids. FIG. 8C shows the sequence of genomic DNA from the affected patient in FIG. 8B which reveals a G to A point mutation at the 3' end of the exon, which exon is excised in mRNA, as compared to a normal sample of genomic DNA. Exonic sequence is in upper case and intronic sequence in lower case letters SEQ ID NO: 46. FIG. 8D shows MspI restriction enzyme analysis of PCR-amplified genomic DNA from members of Family 6, indicating affected individuals. The G to A mutation destroyed a restriction site for MspI (C/CGG). Normal PCR product is digested into 304 bp, 85 bp, and 38 bp fragments, while that containing the mutation is digested into 304 bp and 123 bp fragments. MW is 100 bp ladder (GIBCO-BRL, Gaithersburg, Md.), UC is an uncut sample, C is a control PCR reaction lacking template.

Figure 9A:
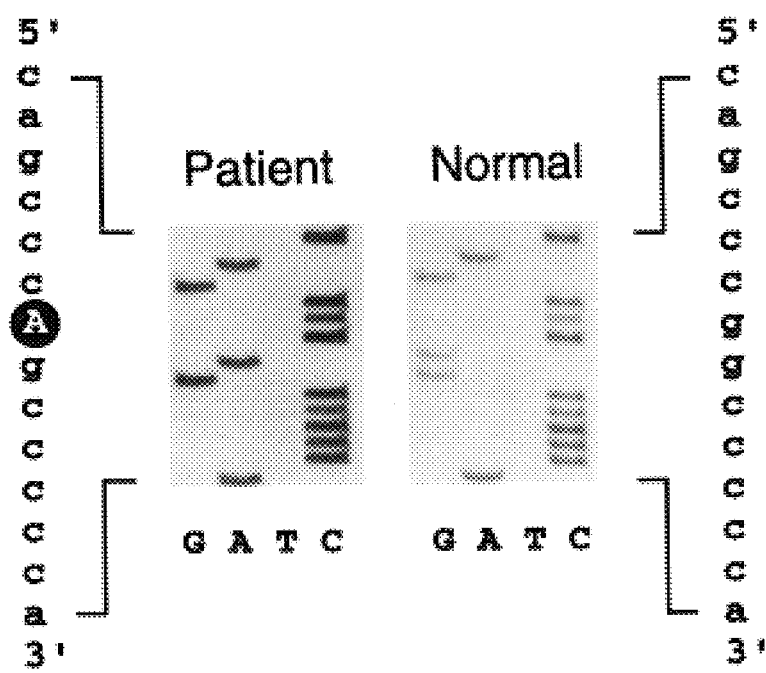
Figure 9B:
Figure 9B:
Figure 9C:
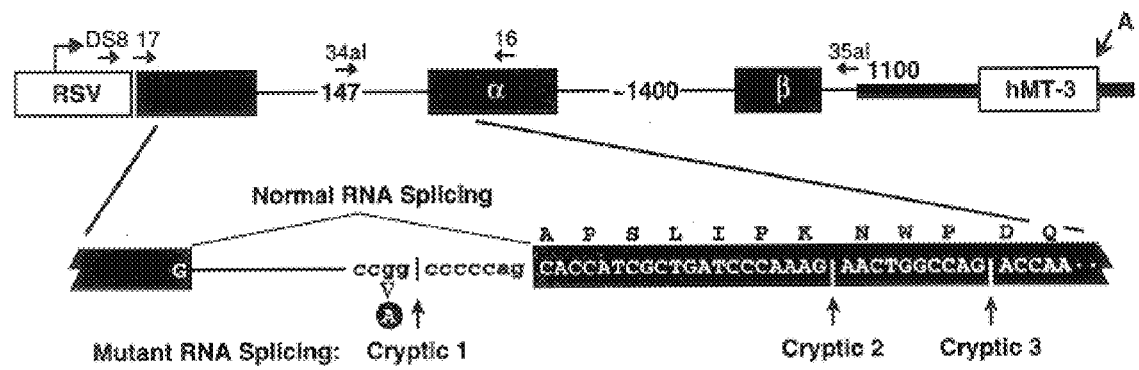
Figure 9D:
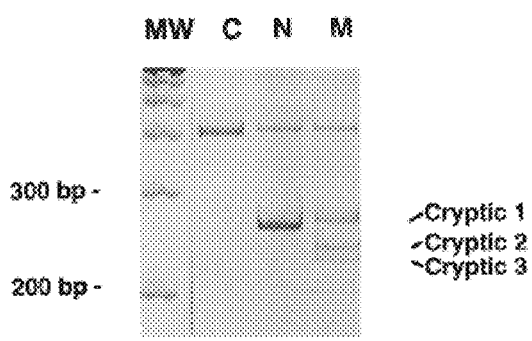

FIG. 9A–D reveal a mutation in the intron preceding NBF-2 exon α, which activates cryptic 3' splice site usage. FIG. 9A displays the sequence of genomic DNA from an affected member of Family 4 which revealed a G to A mutation in the splice site preceding the first exon of the NBF-2 SEQ ID NO 47. FIG. 9B shows NciI restriction enzyme analysis of genomic DNA from members of Family 4, indicating affected individuals. The G to A mutation destroys a restriction site for NciI (CC/(G/C)GG). Normal PCR product is digested into 71 bp and 75 bp fragments, while that containing the mutant sequence is not cut. MW is a molecular weight marker, UC is an uncut sample, C is a control reaction. By previous haplotype analysis, the unaffected sibling in this family had two wild type alleles, P. M. Thomas, G. J. Cote, D. M. Hallman, P. M. Mathew, *Am. J. Hum. Genet.*, supra. FIG. 9C illustrates the constructs used to examine RNA processing of exons within NBF-2. Solid rectangles and thin lines represent human SUR gene exonic and intronic sequences, respectively. The unmarked solid rectangle represents a portion of the exon which is 5' to exon α of the NBF-2 region. The rectangle labeled RSV represents the enhancer and promoter isolated from the rous sarcoma virus long terminal repeat. The thick line represents an intronic sequence derived from vector and the human metallothionine IIA gene, which also contains polyadenylation signals. Normal and mutant RNA splicing patterns, including the location of the three cryptic splice sites, are diagrammed in the lower portion along with SEQ ID NOS: 48 and 49. The open triangle marks the position of the mutated base within the splice site. FIG. 9D shows PCR amplification across splice site of normal (N) and mutant (M) cDNA transcripts, isolated 48 hours after transfection with the splicing constructs. Subcloning and sequencing of these products revealed their identity as diagrammed in FIG. 9C. The control (C) represents cDNA amplified from untransfected cells.

Figure 10:
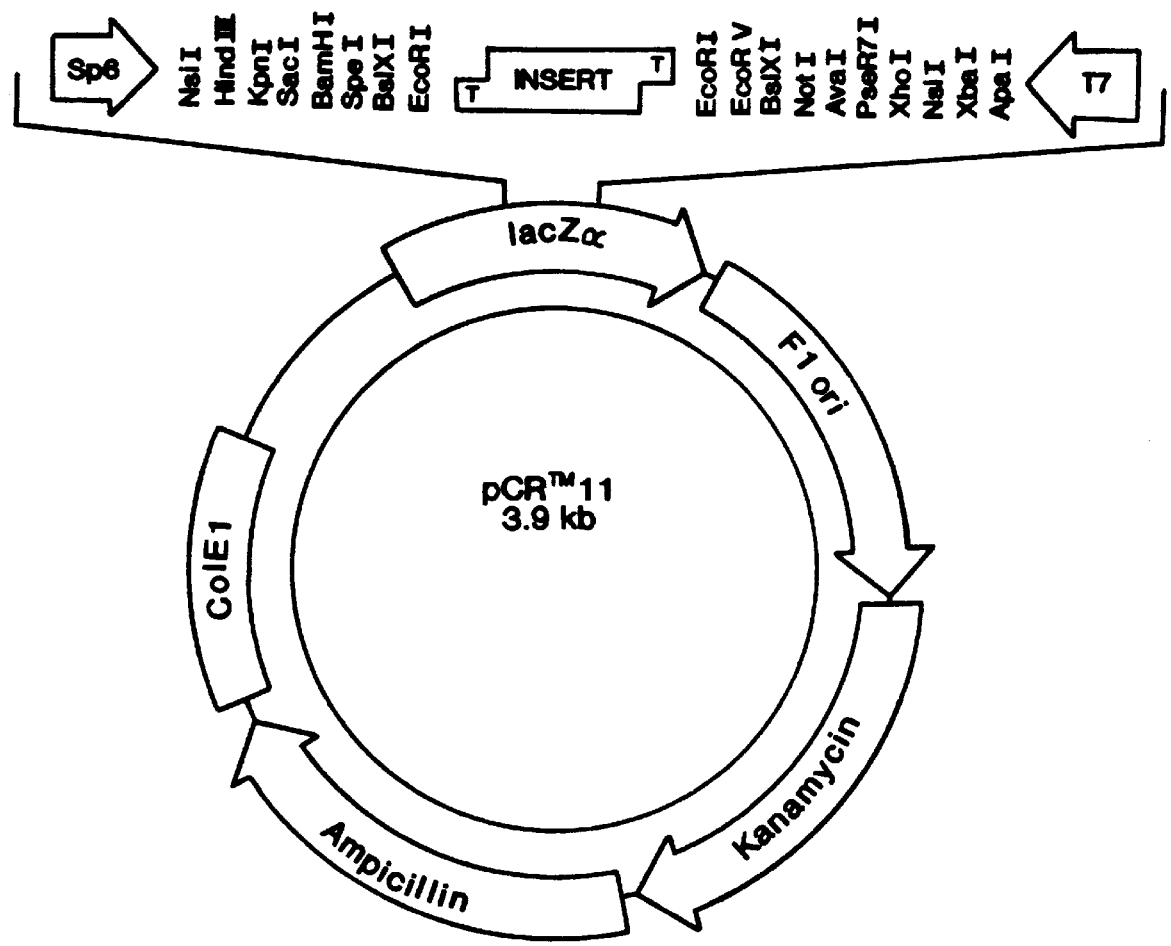

FIG. 10 depicts pCR™ 11 vector.

DETAILED DESCRIPTION OF THE INVENTION

The present invention is directed to the nucleic acid and protein sequences encoding a sulfonylurea receptor. The present invention provides nucleotide sequences of a sulfonylurea receptor, and SEQ ID NOS: 5, 8, and 27. Novel polypeptide sequences, SEQ ID NOS: 6, 9, 27, 28, and 29 coding for a sulfonylurea receptor are also included in the present invention. SEQ ID NOS: 1–3 provide the nucleic acid and amino acid sequences of the last 11 exons of the 3' end of human sulfonylurea receptor, hereinafter referred to, together with the rodent sequences for sulfonylurea receptor, as sequence for the sulfonylurea receptor.

SEQ ID NOS: 5 and 8 provide the cDNA sequences of rodent sulfonylurea receptor. SEQ ID NOS: 1 and 2 provide the human cDNA and genomic DNA sequence of sulfonylurea receptor, respectively. Nucleic acids within the scope of the present invention include cDNA, RNA, genomic DNA, sequences within these larger sequences, antisense oligonucleotides. Sequences encoding the sulfonylurea receptor also include amino acid, polypeptide, and protein sequences. Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, mismatches within the sequences identified herein, which achieve the methods of the invention, such that the mismatched sequences are substantially complementary to the sulfonylurea receptor sequences identified, are also considered within the scope of the present invention. Mismatches which permit substantial complementarity to the sulfonylurea receptor sequences, such as similarity in residues in hydrophobicity, will be known to those of skill in the art once armed with the present disclosure. In addition, the sequences of the present invention may be natural or synthetic.

A purified sulfonylurea receptor is also provided by the present invention. The purified sulfonylurea receptor may have an amino acid sequence as provided by SEQ ID NOS: 6, 9, 27, 28, and 29.

The present invention is directed to sulfonylurea receptor sequences obtained from mammals from the Order Rodentia, including and not limited to hamsters, rats, and mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

There are several transfection techniques by which a sulfonylurea receptor may be obtained. An appropriate RNA may be hybridized to a cDNA to obtain a sulfonylurea receptor nucleic acid sequence. A nucleic acid sequence encoding sulfonylurea receptor may be inserted into cells and the corresponding protein immunoprecipitated with an antibody. Labeled drugs known to bind sulfonylurea receptor protein may be added to cell culture to label the receptor. The drug labeling procedure may involve modifying cells such that the cell culture provides conditions similar to β cells, cells where sulfonylurea receptors naturally appear; and the sulfonylurea receptor may be part of a larger multisubunit ATP receptor channel, which may not be provided by the cells in culture.

Generally, the sequences of the invention may be produced in host cells transformed with an expression vector comprising a nucleic acid sequence encoding the sulfonylurea receptor. The transformed cells are cultured under conditions whereby the nucleic acid sequence coding for the sulfonylurea receptor is expressed. After a suitable amount of time for the protein to accumulate, the protein is purified from the transformed cells.

A gene coding for sulfonylurea receptor may be obtained from a cDNA library. Suitable libraries can be obtained from commercial sources such as Clontech, Palo Alto, Calif. Libraries may also be prepared using the following non-limiting examples hamster insulin-secreting tumor (HIT), mouse αTC-6, and rat insulinoma (RIN) cells. Positive clones are then subjected to DNA sequencing to determine the presence of a DNA sequence coding for sulfonylurea receptor. DNA sequencing is accomplished using the chain termination method of Sanger et al., *Proc. Nat'l. Acad. Sci, U.S.A.*, 1977, 74, 5463. The DNA sequence encoding sulfonylurea receptor is then inserted into an expression vector for later expression in a host cell.

Expression vectors and host cells are selected to form an expression system capable of synthesizing sulfonylurea receptor. Vectors including and not limited to baculovirus vectors may be used in the present invention. Host cells suitable for use in the invention include prokaryotic and eukaryotic cells that can be transformed to stably contain and express sulfonylurea receptor. For example, nucleic acid coding for the recombinant protein may be expressed in prokaryotic or eukaryotic host cells, including the most commonly used bacterial host cell for the production of recombinant proteins, *E. coli*. Other microbial strains may also be used, however, such as Bacillus subtilis, and other enterobacteriaceae such as *Salmonella typhimurium* or *Serratia marcescens*, various species of Pseudomonas, or other bacterial strains.

Commonly used eukaryotic systems include yeast, such as *Saccharomyces cerevisiae*; insect cells, such as *Spodoptera frugiperda*; chicken cells, such as E3C/O and SL-29; mammalian cells, such as HeLa, Chinese hamster ovary cells (CHO), COS-7 or MDCK cells and the like. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for sulfonylurea receptor, such as plasmid expression vectors and viral vectors. The selection of the expression vector is based on compatibility with the desired host cell such that expression of the nucleic acid encoding sulfonylurea receptor results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol or kanamycin resistance.

Suitable expression vectors, promoters, enhancers, and other expression control elements are known in the art and may be found in Sambrook et al., *Molecular Cloning: A Laboratory Manual*, second edition, Cold Spring Harbor Laboratory Press, Cold Spring Harbor, N.Y. (1989), incorporated herein by reference in its entirety.

Transformed host cells containing a DNA sequence encoding sulfonylurea receptor may then be grown in an appropriate medium for the host. The cells are then grown until product accumulation reaches desired levels at which time the cells are then harvested and the protein product purified in accordance with conventional techniques. Suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

Protein preparations, of purified or unpurified sulfonylurea receptor produced by host cells, are accordingly produced which comprise sulfonylurea receptor and other material such as host cell components and/or cell medium, depending on the degree of purification of the protein.

Antibodies, including and not limited to monoclonal, polyclonal, and chimeric, prepared and used against a sulfonylurea receptor are also within the scope of the present invention, and may be prepared by methods known to those of skill in the art such as and not limited to the methods of Kohler and Milstein, *Nature*, 256: 495–497 (1975), incorporated herein by reference in its entirety.

The invention also includes a transgenic non-human animal, including and not limited to mammals, such as and not limited to a mouse, rat, or hamster, whose germ cells and somatic cells contain a sequence encoding a sulfonylurea receptor introduced into the animal or an ancestor of the animal. The sequence may be wild-type or mutant and may be introduced into the animal at the embryonic or adult stage. The sequence is incorporated into the genome of an animal such that it is chromosomally incorporated into an activated state. Embryo cells may be transfected with the gene as it occurs naturally, and transgenic animals are selected in which the gene has integrated into the chromosome at a locus which results in activation. Other activation methods include modifying the gene or its control sequences prior to introduction into the embryo. The embryo may be transfected using a vector containing the gene.

In addition, a transgenic non-human animal may be engineered wherein the sulfonylurea receptor is suppressed. For purposes of the present invention, suppression of the sulfonylurea receptor includes, and is not limited to strategies which cause the sulfonylurea receptor not to be expressed. Such strategies may include and are not limited to inhibition of protein synthesis, pre-mRNA processing, or DNA replication. Each of the above strategies may be accomplished by antisense inhibition of sulfonylurea receptor gene expression. Many techniques for transfering antisense sequences into cells are known to those of skill, including and not limited to microinjection, viral-mediated transfer, somatic cell transformation, transgene integration, and the like, as set forth in Pinkert, Carl, *Transgenic Animal Technology*, 1994, Academic Press, Inc., San Diego, Calif., incorporated herein by reference in its entirety.

Further, a transgenic non-human animal may be prepared such that the sulfonylurea receptor gene is knocked out. For purposes of the present invention, a knock out includes and is not limited to disruption or rendering null the sulfonylurea receptor gene. A knock out may be accomplished, for example, with antisense sequences for the sulfonylurea receptor mutating the sequence for the sulfonylurea receptor. The sulfonylurea receptor gene may be knocked out by injection of an antisense sequence for all or part of the sulfonylurea receptor sequence such as an antisense sequence for all or part of SEQ ID NO: 2. Once the sulfonylurea receptor has been rendered null, correlation of the sulfonylurea receptor to persistent hyperinsulinemic hypoglycemia of infancy may be tested. Sequences encoding mutations affecting the sulfonylurea receptor may be inserted to test alterations in glucose homeostasis.

Also in transgenic non-human animals, the sulfonylurea receptor may be replaced by preparing a construct having an insulin promoter ligated to the sulfonylurea receptor gene. This experiment permits testing of mutant sulfonylurea receptors directly in the pancreas of the transgenic animal.

Transgenic non-human animals may also be useful for testing nucleic acid changes to identify nucleotides which are responsible for ADP and ATP modulation of the sulfonylurea receptor resulting in an increase or decrease in glucose sensitivity of insulin release.

The present invention is also directed to gene therapy wherein a mutant sulfonylurea receptor is replaced by a wild type sulonylurea receptor. A resulting transgenic non-human animal thus comprises a recombinant sulfonylurea receptor. In addition, gene therapy techniques may be used for individuals with persistent hyperinsulinemic hypoglycemia of infancy. For purposes of the present invention, gene therapy refers to the transfer and stable insertion of new genetic information into cells for the therapeutic treatment of diseases or disorders. The foreign gene is transferred into a cell that proliferates to spread the new gene throughout the cell population. Known methods of gene transfer include microinjection, electroporation, liposomes, chromosome transfer, transfection techniques, calcium-precipitation transfection techniques, and the like.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, M. J., 1985, Pharmac. Ther. 29:69–92, incorporated herein by reference in its entirety).

The term "purified", when used to describe the state of nucleic acid sequences of the invention, refers to nucleic acid sequences substantially free of nucleic acid not coding for sulfonylurea receptor or other materials normally associated with nucleic acid in non-recombinant cells, i.e., in its "native state."

The term "purified" or "in purified form" when used to describe the state of a sulfonylurea receptor, protein, polypeptide, or amino acid sequence, refers to sulfonylurea receptor sequences free, to at least some degree, of cellular material or other material normally associated with it in its native state. Preferably the sequence has a purity (homogeneity) of at least about 25% to about 100%. More preferably the purity is at least about 50%.

To begin to elucidate the relationship between the sulfonylurea receptor and $K_{ATP}$, the iodinated derivative of glyburide was used to identify, and subsequently to purify and obtain N-terminal amino acid sequence from the 140 kDa high affinity, hamster insulin-secreting tumor (HIT) cell sulfonylurea receptor. The peptide sequence data was used to clone full length cDNAs encoding the rat and hamster β-cell proteins of the present invention.

Another embodiment of the present invention is a method of detecting persistent hyperinsulinemic hypoglycemia of infancy comprising obtaining a sample comprising patient nucleic acids from a patient tissue sample; amplifying sulfonylurea receptor specific nucleic acids from said patient nucleic acids to produce a test fragment; obtaining a sample comprising control nucleic acids from a control tissue sample; amplifying control nucleic acids encoding wild type sulfonylurea receptor to produce a control fragment; comparing the test fragment with the control fragment to detect the presence of a sequence difference in the test fragment, wherein a difference in said test fragment indicates persistent hyperinsulinemic hypoglycemia of infancy is also an embodiment of the present invention.

Persistent hyperinsulinemic hypoglycemia of infancy (PHHI) is an autosomal recessive disorder which results in unregulated insulin secretion. The present invention revealed several different mutations in the sulfonylurea receptor in individuals with PHHI. These mutations include nucleic acid transition and restriction fragment length polymorphism, both defined herein as sequence differences. The nucleic acid sequence transition may be a G to A transition at nucleic acid position 750 in SEQ ID NO: 1 which results in PHHI. This transition was found to occur in nine affected children in nine different families of the families studied. The pancreatic cDNA from a child with this transition involved skipping an exon. Genomic DNA template was amplified to obtain the product for Msp I digestion for testing and confirmation of the mutation at position 750 in SEQ ID NO: 1. When cDNA is amplified, the Msp I restriction site is not present. Exon X of FIG. 7 was skipped resulting in an mRNA transcript having a 109 bp deletion, a frame shift, and the inclusion of a premature stop codon. This deletion may be seen by performing rtPCR on the child's mRNA. Amplification of SEQ ID NO: 1 with primer sequences of SEQ ID NOS: 18 and 20 resulted in a 427 base pair product for the normal as well as for the mutant cDNA. Digesting the normal and mutant products with MspI, however, resulted in three fragments (304 bp, 85 bp, and 38 bp) for the normal gene and two fragments (304 bp and 123 bp) for the mutant gene of affected children.

Another mutation involves a G to A transition in intron 11 of the human sulfonylurea receptor which gives rise to PHHI. The transition site corresponds to position 27 of SEQ ID NO: 31. The G to A transition destroys a restriction site for NciI. Both normal and mutant PCR products resulted in 146 bp. Digestion with NciI resulted in two fragments (71 bp and 75 bp) fragments for normal individuals, while the mutant sequence was not be cut by NciI and thus remained at 146 bp.

A method of detecting persistent hyperinsulinemic hypoglycemia of infancy comprising obtaining a sample comprising patient genomic DNA from a patient tissue sample; amplifying sulfonylurea receptor specific DNA from said patient genomic DNA to produce a test fragment; obtaining a sample comprising control nucleic acids from a control tissue sample; amplifying control DNA encoding wild type sulfonylurea receptor to produce a control fragment; comparing the test fragment with the control fragment to detect a test fragment having G to A transition at nucleic acid position 750 of SEQ ID NO: 1, or a G to A transition at nucleic acid position 27 of SEQ ID NO: 31, wherein said test fragment indicates persistent hyperinsulinemic hypoglycemia of infancy is also an embodiment of the present invention.

Also within the scope of the present invention is a method of detecting persistent hyperinsulinemic hypoglycemia of infancy comprising obtaining a sample comprising patient genomic DNA from a patient tissue sample; amplifying sulfonylurea receptor specific DNA from said patient genomic DNA to produce a test fragment; obtaining a sample comprising control nucleic acids from a control tissue sample; amplifying control DNA encoding wild type sulfonylurea receptor to produce a control fragment; digesting said test fragment and said control fragment with an endonuclease selected from the group consisting of NciI and MspI; and comparing the test fragment with the control fragment to detect a restriction fragment length polymorphism, wherein said restriction fragment length polymorphism indicates persistent hyperinsulinemic hypoglycemia of infancy.

The restriction fragment polymorphisms include test fragments of about 304 bp and about 123 bp as a result of MspI restriction and a test fragment of about 146 bp as a result of NciI restriction using primer sequences of SEQ ID NOS: 18 and 20. The test fragments thus indicate persistent hyperinsulinemic hypoglycemia of infancy.

In accordance with methods of the present invention, methods of detecting PHHI in a patient are provided comprising obtaining a patient tissue sample for testing. The tissue sample may be solid or liquid, a body fluid sample such as and not limited to blood, serum, saliva, sputum, mucus, bone marrow, urine, lymph, and a tear; and feces. In addition, a tissue sample such as pancreatic tissue may be provided for the detection of PHHI in accordance with the present invention.

A test fragment is defined herein as an amplified sample comprising sulfonylurea receptor specific nucleic acids from a patient suspected of having PHHI. A control fragment is an amplified sample comprising normal or wild type sulfonylurea receptor specific nucleic acids from an individual not suspected of having PHHI.

The method of amplifying nucleic acids may be the polymerase chain reaction using a pair of primers wherein at least one primer within the pair is selected from the group consisting of SEQ ID NO: 12–20. When the polymerase chain reaction is the amplification method of choice, a pair of primers may be used such that one primer of the pair is selected from the group consisting of SEQ ID NOS: 13, 14, 17, and 19 and the second primer of the pair is selected from the group consisting of SEQ ID NOS: 12, 15, 16, 18, and 20.

Nucleic acids, such as DNA (such as and not limited to genomic DNA and cDNA) and/or RNA (such as and not limited to mRNA), are obtained from the patient sample. Preferably RNA is obtained. A whole blood gradient may be performed to isolate nucleated cells and total RNA is extracted such as by the RNazole B method (Tel-Test Inc., Friendswood, Tex.) or by modification of any methods known in the art such as described in Sambrook et al., *Molecular Cloning: A Laboratory Manual,* 1989, Cold Spring Harbor Laboratory, Cold Spring Harbor, N.Y., incorporated herein by reference in its entirety.

Nucleic acid extraction is followed by amplification of the same by any technique known in the art. The amplification step includes the use of at least one primer sequence which is complementary to a portion of sulfonylurea receptor specific expressed nucleic acids or sequences. Primer sequences useful in the amplification methods include and are not limited to SEQ ID NOS: 12–20, which may be used in the amplification methods. Any primer sequence of about 10 nucleotides to about 35 nucleotides, more preferably about 15 nucleotides to about 30 nucleotides, even more preferably about 17 nucleotides to about 25 nucleotides may be useful in the amplification step of the methods of the present invention. In addition, mismatches within the sequences identified above, which achieve the methods of the invention, such that the mismatched sequences are substantially complementary and thus hybridizable to the sequence sought to be identified, are also considered within the scope of the disclosure. Mismatches which permit substantial similarity to SEQ ID NOS: 12–20, such as and not limited to sequences with similar hydrophobicity and hydrophilicity, will be known to those of skill in the art once armed with the present disclosure. The primers may also be unmodified or modified. Primers may be prepared by any method known in the art such as by standard phosphoramidite chemistry. See Sambrook et al., supra.

The method of amplifying nucleic acids may be the polymerase chain reaction using a pair of primers wherein at least one primer within the pair is selected from the group consisting of SEQ ID NO: 12–20. When the polymerase chain reaction is the amplification method of choice, a pair of primers may be used such that one primer of the pair is selected from the group consisting of SEQ ID NOS: 12–20.

Primers used in mutational analysis were SEQ ID NO: 12: CACGCTCAGGTTCTGGAT; SEQ ID NO: 13: TCAACTGGATGGTGAGGA; SEQ ID NO: 14: 5' TGA-CATCGCCAAACTGC; SEQ ID NO: 15: TCCTGGCAGT-GCCTTCA; SEQ ID NO: 16: TCCTCTCAGGGTCCAG-GTTA; SEQ ID NO: 17: ACAAGGAGCCTGGGGAT; SEQ ID NO: 18: TGCATGGGTCCCAGTGA; SEQ ID NO: 19: TTGACCATTCACCACATTGGTGTGC; and SEQ ID NO: 20: TCCTGGCAGTGCCTTCA.

When an amplification method includes the use of two primers, a first primer and a second primer, such as in the polymerase chain reaction, the first primer may be selected from the group consisting of SEQUENCE ID NOS: 13, 14, 17, and 19; and the second primer may be selected from the group consisting of SEQUENCE ID NOS: 12, 15, 16, 18, and 20. Any primer pairs which transcribe nucleic acids toward each other and which are specific for sulfonylurea receptor may be used in accordance with the methods of the present invention.

Total extraction of RNA is preferably carried out. As used herein, the term "amplification" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987)). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., *PCR Protocols*, Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Tag polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker, G. T., et al., *Proc. Natl. Acad, Sci.* (*U.S.A.*) 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

Sulfonylurea receptor specific nucleic acids can also be detected using a cyclic probe reaction (CPR). In CPR, a probe having a 3' and 5' sequences of non-sulfonylurea receptor specific DNA and middle sequence of sulfonylurea receptor specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to a sulfonylurea receptor specific expressed nucleic acid.

Still other amplification methods described in GB Application No. 2 202 328, and in PCT Application No. PCT/US89/01025, each of which is incorporated by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al., *Proc. Natl. Acad. Sci.* (*U.S.A.*) 1989, 86:1173, Gingeras T. R., et al., PCT Application WO 88/10315, each of which is incorporated herein by reference in its entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has sulfonylurea receptor specific sequences. Following polymerization, DNA/RNA hybrids are digested with RNase H while double stranded DNA molecules are heat denatured again. In either case the single stranded DNA is made fully double stranded by addition of second sulfonylurea receptor specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate sulfonylurea receptor specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA ("dsDNA") which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli.* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: *PCR Protocols: A Guide to Methods and Applications* 1990, Academic Press, New York) and "one-sided PCR" (Ohara, O., et al., *Proc. Natl. Acad. Sci.* (*U.S.A.*) 1989, 86:5673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., *Genomics* 1989, 4:560, incorporated herein by reference in its entirety), may also be used in the amplification step of the present invention.

Test fragment and control fragment may be amplified by any amplification methods known to those of skill in the art, including and not limited to the amplification methods set forth above. For purposes of the present invention, amplification of sequences encoding patient and wild type sulfonylurea receptor includes amplification of a portion of a sequence such as and not limited to a portion of the sulfonylurea receptor sequence of SEQ ID NO: 1, such as sequence of a length of about 10 nucleotides to about 1,000 nucleotides, more preferably about 10 nucleotides to about 100 nucleotides, or having at least 10 nucleotides occurring anywhere within the SEQ ID NO: 1, where sequence differences are known to occur within sulfonylurea receptor test fragments. Thus, for example, a portion of the sequence encoding the second nucleotide binding fragment (NBF-2) region of sulfonylurea receptor of a patient sample and a control sample may be amplified to detect sequence differences between these two sequences.

Following amplification of the test fragment and control fragment, comparison between the amplification products of the test fragment and control fragment is carried out. Sequence differences such as and not limited to nucleic acid transition and restriction digest pattern alterations may be detected by comparison of the test fragment with the control fragment. Nucleic acid transition includes and is not limited to a G to A transition at nucleic acid position 750 of SEQ ID NO: 1. Another nucleic acid transition involves a G to A transition at nucleic acid position 27 of SEQ ID NO: 31.

These nucleic acid transitions lead to restriction fragment length polymorphisms as exemplified by the altered results following MspI and NciI restriction digests set forth above. Accordingly, the restriction fragment length polymorphisms of test fragments may be compared to the restriction fragments of control fragments.

Alternatively, the presence or absence of the amplification product may be detected. The nucleic acids are fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labelled probe encoding a sulfonylurea mutation is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 500 nucleotides in length, and more preferably about 2,454 nucleotides in length. The preferred sequence of the probe is set forth in SEQ ID NO: 32. Mismatches which permit substantial similarity to SEQ ID NO: 32, such as and not limited to sequences with similar hydrophobicity and hydrophilicity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}$P labeling, and the like. Preferably, the product, such as the PCR product, may be run on an agarose gel and visualized using a stain such as ethidium bromide. See Sambrook et al., supra. The matrix may then be analyzed by autoradiography to locate particular fragments which hybridize to the probe. Yet another alternative is the sequencing of the test fragment and the control fragment to identify sequence differences. Methods of nucleic acid sequencing are known to those of skill in the art, including and not limited to the methods of Maxam and Gilbert, *Proc. Natl. Acad. Sci., USA* 1977, 74, 560–564 and Sanger, *Proc. Natl. Acad. Sci., USA* 1977, 74, 5463–5467.

A diagnostic kit for detecting PHHI comprising in one or more containers at least one primer which is complementary to a sulfonylurea receptor sequence and a means for visualizing amplified DNA is also within the scope of the present invention. Alternatively, the kit may comprise two primers. In either case, the primers may be selected from the group consisting of SEQ ID NOS: 12–20, for example. The diagnostic kit may comprise a pair of primers wherein one primer within said pair is complementary to a region of the sulfonylurea receptor gene, wherein one of said pair of primers is selected from the group consisting of SEQ ID NO: 12–20, a probe specific to the amplified product, and a means for visualizing amplified DNA, and optionally including one or more size markers, and positive and negative controls. The diagnostic kit of the present invention may comprise one or more of a fluorescent dye such as ethidium bromide stain, $^{32}$P, and biotin, as a means for visualizing or detecting amplified DNA. Optionally the kit may include one or more size markers, positive and negative controls, restriction enzymes such as and not limited to MspI and/or NciI, and/or a probe specific to the amplified product.

The following examples are illustrative but are not meant to be limiting of the invention.

EXAMPLES

Purification and Partial Characterization of the 140 kDa Receptor

HIT cell membranes were photolabeled using a radioiodinated derivative of the second generation hypoglycemic drug, glyburide, according to the methods of Nelson, D. A., et al., *JBC*, 1992, 267:14928, Aguilar-Bryan, L., et al., *JBC*, 1992, 267–14934, and Aguilar-Bryan, L., et al., *JBC*, 1990, 265:8218, the disclosures of which are hereby incorporated by reference in its entirety.

Glyburide (Kramer et al. *FEBS Lett.* 1988 229:355–359) and an iodinated derivative of glyburide (Aguilar-Bryan et al. *J. Biol. Chem.* 1990 265:8218–8224) are known to photolabel a 140 kDa polypeptide. The pharmacological characteristics of the photolabeling, a kD in the low nanomolar range, and appropriate rank order of displacement with other insulin-releasing sulfonylureas, are those expected from studies on glyburide-induced insulin release from islets (Panten et al. *Biochem. Pharm.* 1989 38:1217–1229) and βcell lines (Schmid-Antomarchi et al. *J. Biol. Chem.* 1987 262:15840–15844) and inhibition of $K_{ATP}$ channel activity. Glyburide was purchased from Sigma (St. Louis, Mo.) and prepared in stock solutions of 10 mM in dimethyl sulfoxide. Radioligand stocks were prepared by diluting high pressure liquid chromatography-purified 5-[$^{125}$I] iodo-2-hydroxyglyburide in dimethyl sulfoxide. Specific activity (cpm/mol) was measured on radioligand diluted 1/1000 into 10 mM Tris, 100 mM NaCl, 2 mM EDTA, pH 7.4, and the absorbance determined at 2.5 nm intervals in a UV-VIS Gilford spectrophotometer. Dimethylsulfoxide was diluted 1/1000 into the same buffer, and the absorbance of the buffer without drug was subtracted at each wavelength to generate the final absorbance profile.

HIT cells, passage 67–73, were seeded in roller bottles at 50×10$^6$ cells/bottle in 100 ml of Dulbecco's modified Eagle's medium plus 10% fetal bovine serum. Cells were fed with 200 ml of medium plus serum 4–5 times over a period of 2 weeks until the cells were confluent. After plating and each feeding, bottles were gassed with 5% $CO_2$ prior to capping.

The cells in confluent roller bottles were washed with phosphate-buffered saline (0.14 M NaCl, 3 mM KCl, 2 mM $KH_2PO_4$, 1 mM $Na_2HPO4$, pH 6.8) and then incubated at room temperature with 25 ml of phosphate-buffered saline plus 2 mM EDTA until cells detached from the sides of the bottles. Cells were pelleted at 900 xg for 10 minutes at 4° C.

All steps were carried out at 0–4° C. Cell pellets were resuspended in 5 mM Tris, 2 mM EDTA, 0.1 mM PMSF, pH 7.4, using approximately 5 ml of buffer for each roller bottle. Cells were placed on ice for 40 minutes to allow swelling and then homogenized with 10 strokes of a motorized glass-TEFLON™, insoluble, nonadhesive polymer; homogenizer (500 rpm). The homogenate was centrifuged at 1000 xg for 10 minutes to remove nuclei and cellular debris, and the supernatant transferred to 30 ml of Beckman polycarbonate, screw-cap ultracentrifuge tubes. Supernatants were centrifuged at 100,000 xg for 60 minutes in a Beckman 60 Ti rotor. The pellets were resuspended in membrane storage buffer (10 mM Tris, 100 mM NaCl, 2 mM EDTA, 20% glycerol, 0.1 mM PMSF, pH 7.4). 200 mg of membrane protein were typically obtained from 20 roller bottles.

Membranes were stored at −80° C. at 5 mg/ml protein in 10 mM Tris (pH 7.5), 0.1 M NaCl, 2 mM EDTA, 20% glycerol. To monitor receptor purification, an aliquot (5–20 ml) of the membranes was incubated with 1 nM [$^{125}$I]-iodo-2-hydroxyglyburide for 15 minutes and the sample photolabeled. Binding of 5-[$^{125}$I]-iodo-2-hydroxyglyburide (5–10 nM) to membranes was done for 30 minutes at 23° C. Aliquots were pipetted onto parafilm and irradiated at 23° C. in a UV cross-linker (Fisher Scientific). The energy settings for the UV cross-linker were factory calibrated at 254 nm. For cross-linking at 312 nm, a conversion factor was estimated by determining the time required for the UV cross-linker to deliver a specific amount of energy with each set of bulbs, and then multiplying by the ratio of these times.

All subsequent steps were performed at room temperature in the presence of 0.1 mM PMSF, 0.1 mM phenanthroline and 0.1 mM iodoacetamide. 20% (w/v) digitonin was freshly prepared by boiling in deionized water, then added to 200–400 mg thawed labeled membranes to a final concentration of 1%. Membranes were solubilized for 15 minutes then sedimented for 1 hr at 100,000 xg. The supernatant was divided into 4 ml aliquots and each aliquot was chromatographed over a 1 ml Concanavalin A-Sepharose column equilibrated with 25 mM Tris-HCl, pH 7.5,0.1 M NaCl, 2 mM EDTA, 1% digitonin. The solution was cycled through the column twice before washing the column with 8 ml of the equilibration buffer. Retained protein was eluted with 4 ml of the same buffer containing 0.5 M methyl α-D-mannopyranoside. The eluted protein was stored at −80° C. Three Con A eluates were combined, then cycled twice over a 1 ml column of reactive green 19-agarose equilibrated with 50 mM HEPES (pH 8.5), 2 mM EDTA, 0.2% digitonin. The column was washed with 8 ml of the equilibration buffer followed by 8 ml of the same buffer containing 0.4 M NaCl. The retained protein was eluted with 4 ml of the equilibration buffer containing 1.5 M NaCl. The two pooled eluates were diluted 1:1 with the HEPES equilibration buffer without NaCl and cycled twice over a 1 ml phenylboronate-10 agarose column. The column was washed with 8 ml of the HEPES buffer, followed by 2 ml of 0.1 M Tris-HCl, pH 7.5, 2 mM EDTA, 0.1% digitonin. Protein was eluted with 4 ml of 0.1 M Tris (pH 7.5), 2 mM EDTA, 0.1% SDS. The protein was concentrated to 0.5 ml using a 100,000 MW cutoff Amicon filter, pretreated with 5% Tween-20®, detergent, then loaded onto a single 5 cm wide lane of a 5.5% polyacrylamide SDS gel. After electrophoresis the gel was stained with Coomassie blue, destained, and the receptor band excised with a razor blade. The receptor was electroeluted into a 14,000 MW cutoff dialysis bag and concentrated by Amicon filtration.

Table 1 summarizes the yields and fold-purification in the scheme developed for receptor purification. The amount of receptor, yields, and fold-purification reported after each step are based on the radioactivity, determined by γ counting, in the 140 kDa band after electrophoresis relative to the total protein loaded on a gel lane (as determined using the BioRad protein assay). HIT cell membranes contain approximately 1.6 pmol of receptor per mg of membrane protein as determined by filtration binding (Aguilar-Bryan et al. *J. Biol. Chem.* 1990 265:8218–8224).

TABLE 1

Purification of the High Affinity 140 kDa Sulfonylurea Receptor from HIT cells

| Step | Total Volume ml | Total Protein mg | Receptor pmol | Receptor pmol/mg | Purification ~fold | Yield % |
|---|---|---|---|---|---|---|
| Crude Membranes | 90 | 200 | 320 | 1.6 | 1 | 100 |
| Supernatant | 90 | 150 | 240 | 1.6 | 1 | 75 |
| ConA-Sepharose | 48 | 10.2 | 80 | 7.8 | 4.9 | 25 |
| Reactive Green 19-agarose | 16 | 1.8 | 56 | 31.1 | 19.5 | 18 |
| Phenyl boronate agarose | 4 | 0.56 | 45 | 80.4 | 50.4 | 14 |
| SDS-PAGE electroelute | 0.2 | ~0.002 | 8 | 4000 | 2507 | 2.5 |

Figure 1A:
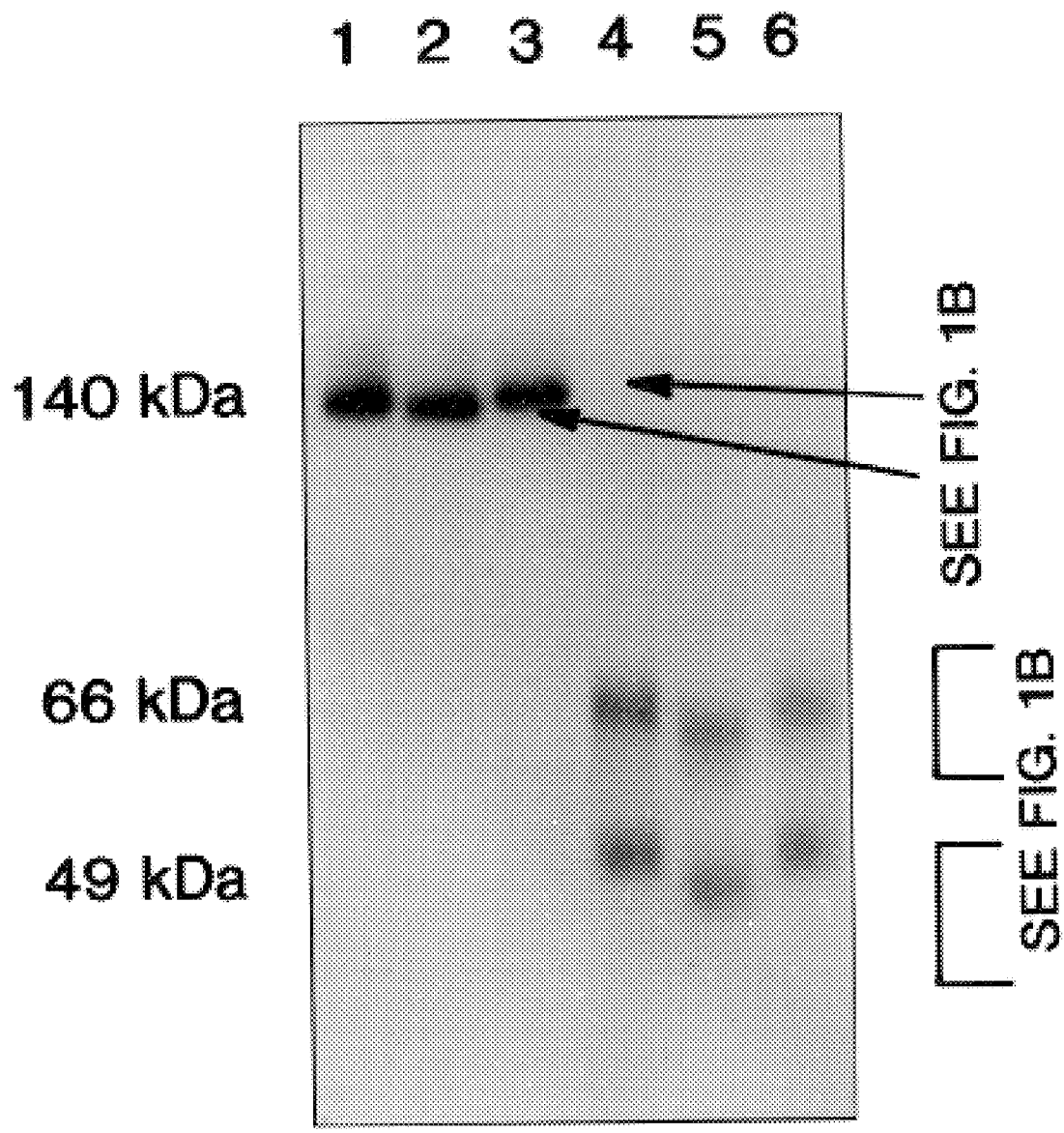

For the autoradiogram depicted in FIG. 1A, 1–2 μg of purified, radiolabeled receptor was made 1% in β-octylglucoside and divided into 6 aliquots. Lane 1 contained receptor kept on ice. The receptor was incubated in the presence (lane 2) and absence (lane 3) of Endo F for 30 min at 37° C. Aliquots of the samples for lanes 1–3 were further incubated with V8 protease (1 μg/10 μl) for 30 min at 37° C., yielding two radiolabeled peptides of 66 and 49 kDa (lanes 4 and 6), both of which are N-glycosylated as indicated by the mobility shift after endo F treatment (lane 5). To obtain N-terminal sequence from the intact receptor, 2 μg of protein was separated by electrophoresis on a single, 0.8 cm wide lane of a 5.5% gel. The receptor was transferred to ProBlot (Applied Biosystems) in 10 mM CAPS (pH 11), 10% MeOH, the filter stained for 10–20 seconds with Coomassie blue, destained, the band excised and microsequenced. To prepare receptor fragments for microsequencing, 10 μg of purified receptor was cleaved with V8, electrophoresed on a single lane and the fragments from the partial digest transferred to ProBlot. Fragments were prepared and sequenced multiple times as indicated in the figure. Gels used in the preparation of receptor and fragments for microsequencing were aged overnight, and the top tray buffer contained 0.1 mM thioglycolate.

Figure 1B:
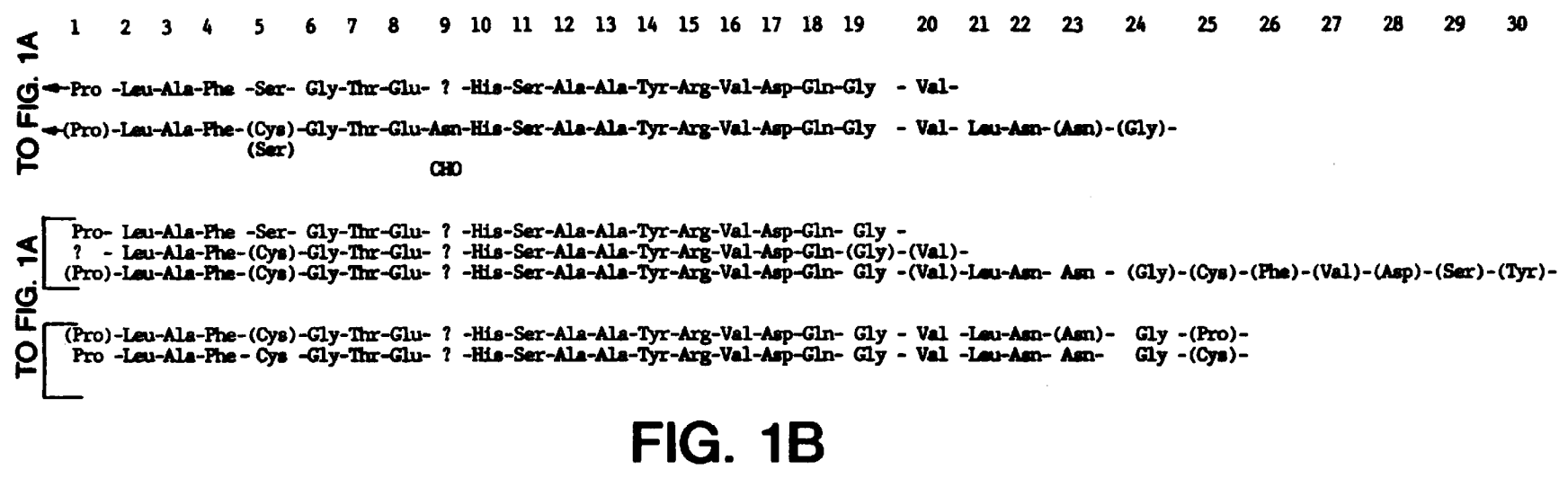

The purified receptor showed a small apparent molecular weight decrease ($\Delta M_r$~3000) following treatment with Endoglycosidase F/N-glycosidase F (Endo F) and yielded two bands following limited cleavage with V8 protease (FIGS. 1A and 1B). Each of the major labeled proteolytic fragments, $M_r$~69 and 49 kDa, shift mobility after digestion with Endo F. Identical N-terminal sequence, 15–25 residues, were recovered from each of the major labeled peptides. No residue was obtained at residue 9 when the glycosylated peptides were sequenced; an aspartic acid was identified at residue 9 in the deglycosylated receptor indicating this is an N-glycosylated asparagine. In addition, N-terminal sequences were recovered on two unlabeled V8 peptides and a third minor labeled peptide. The results indicate there is an N-linked glycosyl group at residue nine in the mature receptor, suggesting that the N terminus is extracellular, and that the sulfonylurea labeling site is within the first 50 kDa of the receptor.

Two multiple antipeptide antibodies (MAPs), directed against residues 1 through 8 and 10 through 20 both immunoprecipitate photolabeled 140 kDa receptors from HIT, mouse αTC-6, and rat insulinoma (RIN) cells. MAPs were prepared by synthetic protein sequencing (Perkin Elmer- ABI, 430 A Peptide Synthesizer, Foster City, Calif.) to obtain antibodies to M-P-L-A-F-C-G-T, SEQ ID NO: 10, residues 1–8 of SEQ ID NOS: 28 and 29. This process was repeated for residues 10–20 of SEQ ID NOS: 28 and 29, N-H-S-A-A-Y-R-V-D-Q-G, SEQ ID NO: 11. A purified sulfonylurea receptor protein was immunoprecipitated from HIT cells using the MAPs prepared as set forth above.

HIT cell membranes were incubated with 5-[$^{125}$I]iodo-2-hydroxyglyburide, photolabeled, solubilized with 1% digitonin, centrifuged at 100,000 xg and the supernatant incubated with 1/10 volume of preimmune serum, immune serum, immune serum+anti-MAP 10–20, or immune serum+ irrelevant MAP peptide. 50 μl of protein A-Sepharose was added and the mixture was incubated for 2 hours at room temperature, the beads washed with buffer, heated in the presence of pH 9 sample buffer, electrophoresed on a 6% polyacrylamide SDS gel, and an autoradiogram prepared.

Figure 2A:
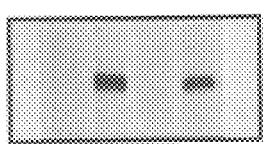
FIG. 2A shows that antibodies against residues 10–20 specifically recognize the 140 kDa polypeptide. Purified 140 kDa polypeptide was electrophoresed on a single lane of a 6% SDS gel and transferred to Immobilon P. The Immobilon P was placed in a miniblotter and the lanes incubated as follows: Lane 1—Preimmune serum. Lane 2—Immune serum. Lane 3—Immune serum+immunogen. Lane 4—immune serum+irrelevant MAP peptide. The filter was further incubated with a second antibody (goat anti-rabbit conjugated to alkaline phosphatase) and developed with the appropriate substrates.
Figure 2B:
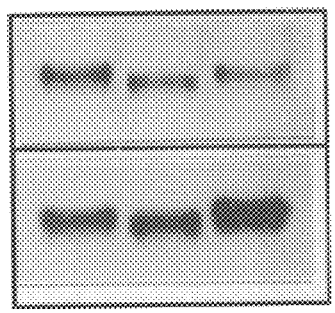
FIG. 2B displays antibodies which recognize a polypeptide with the appropriate mobility shift following Endo F treatment. Purified receptor (lane 1) was incubated for 30 min at 37° C. in the presence (lane 2), or absence (lane 3) of endoglycosidase F/N-glycosidase F, incubated with first (anti-MAP 10–20) and second antibody, and developed with substrate. The bottom panel shows the autoradiogram of the immunoblot in the top panel.
Figure 2C:
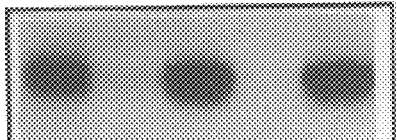
FIG. 2C shows antibodies which immunoprecipitate the photolabeled 140 kDa receptor. HIT cell membranes were incubated with $^{125}$I-kDa labeled iodoglyburide, photolabeled, solubilized with 1% digitonin, centrifuged at 100,000×g and the supernatant (lane 1) incubated with preimmune serum (lane 2), immune serum (lane 3), immune serum+anti-MAP 10–20 (lane 4) and immune serum+irrelevant MAP peptide (lane 5). Samples were co-incubated with protein A-SEPHAROSE®, beaded form of agarose polysaccharides, the beads washed with buffer, heated in the presence of pH 9 sample buffer, electrophoresed on a 6% polyacrylamide SDS gel, and an autoradiogram prepared. Results using antibodies against receptor residues 1–8 were the same as those using antibodies against residues 10–20.

The immunoprecipitation was competed using the immunizing peptide, but not the other MAPS (FIGS. 2A–C). The amino acid sequence is derived from the photolabeled protein and the N-terminal amino acid sequence is conserved between mouse, rat, and hamster.

Isolation and Characterization of cDNA Clones

Degenerate PCR primers with flanking restriction sites were designed based on the sequence obtained from the labeled peptides. The primers used were as follows: primer 1 (SEQ ID NO: 23):

5' GAGAGAAGCTT(T/C)TG(T/C)GG(T/C/G/A)GA(A/G) AA(T/C)CA-3' primer 2 (SEQ ID NO: 24):

5' GAGAGAGAATTCC(T/C)TG(A/G)TC(T/C/G/A)AC(T/ C/G/A)C(G/T)(A/G)TA-3',

The bases in parenthesis indicate the degeneracy at that position. The sequence in bold was derived from the peptide sequence obtained from the N-terminus of the sulfonylurea receptor. The remaining 5' sequence was added to facilitate subcloning. Primer 1 has a HindIII site at the 5' end; Primer 2 was engineered with an EcoRI site at the 5' end. These primers were used in a standard PCR reaction with a random primed cDNA library, constructed in λZAPII using mouse α-cell poly A+ mRNA, as template. The following cycle times and temperatures were employed: 94° C. for 10 minutes; 85° C. for 3 minutes, [50° C. for 2 minutes, 72° C. for 5 minutes, 94° C. for 2 minutes,] 50° C. for 2 minutes, 72° C. for 5 minutes.

The bracketed conditions were cycled 30 times. From the N-terminal peptide sequence of the receptor a 47 base pair coding region was expected to be amplified plus the 20 base pairs added to the primers to facilitate cloning yielding an expected 67 base pair product. The 47 base pair coding region was predicted to have 14 base pairs that were not present in the primers. The PCR product obtained was approximately 67 base pairs and was restricted with EcoRI and HindIII, subcloned into M13 and sequenced. The resulting sequence gave the expected 14 base pairs indicating the sequence was derived from the receptor. The 47 base pair oligonucleotide given below was synthesized based on the consensus sequence derived from nine M13 clones:

5'TTTTGCGGGACGGAGAATCACTCGGCCGCCTACC GCGTCGACCAAGG-3', (SEQ ID NO: 25). This oligonucleotide was used to screen the random primed mouse αTC-cell cDNA library.

A 1.1 kb cDNA was cloned which encoded 28 amino acids obtained from peptide sequencing. This cDNA fragment was used to screen RIN and HIT cell cDNA λ libraries to obtain full sequence.

The nucleotide sequence of a 4635 bp rat receptor cDNA includes an open reading frame that encodes a 1498 amino acid protein with a mass of 167,834 daltons, larger that predicted by SDS polyacrylamide gel electrophoresis. Aguilar-Bryan, L., et al., *JBC*, 1990, 265:8218. There is a single insertion of an asparagine at position 742 and a deletion of a threonine at position 831. The first difference between the hamster and rat sequences is in the same relative position, 21 residues C-terminal of the Walker consensus site, as the ΔF508 deletion seen in a common cystic fibrosis transconductance regulator (CFTR) mutation (Riordan et al. *Science* 1989 245:1066–1073). In addition to the insertion and deletion, the first nucleotide binding fold contains approximately a third (10/33) of all differences between the two species.

The mature rat protein, defined by peptide sequencing, begins with a proline following the methionine start site. In the RIN cell receptors the adjacent amino acid is a methionine. This is the initiating methionine based on the surrounding sequence which is a good fit to the consensus pattern for initiation, GCC(A/G)CCAUG(G) (SEQ ID NO: 26) (Kozak, M. *Cell* 1986 44:283), including the strongly conserved A at position −3. However, in the mouse receptor, an additional 35 amino acids is found preceding this proline which cannot eliminate the possibility that some forms of the hamster and rat receptors have similar leader sequences. Confirming the chemical sequence, residue 9 in the mature proteins is an asparagine within a consensus glycosylation site.

A Blast search of the National Center for Biotechnology Information (NCBI) nucleotide database with the receptor sequence produced matches with several members of the P-glycoprotein/multidrug resistance protein family. A similar search with the amino acid sequence indicated the sulfonylurea receptor is a member of the ATP-binding cassette superfamily with two putative nucleotide binding domains. The sulfonylurea receptor sequence revealed 29% similarity, to an ATP-binding cassette superfamily member, termed a multidrug resistance-associated protein (MRP), isolated from a small cell lung carcinoma cell line (H69AR) selected with doxorubicin (Cole et al. *Science* 1992 258:1650–1654). A cluster analysis of this molecule, dvhuar in the Protein Identification Resource (PIR) database, indicates it is related to the leishmania P-glycoprotein-related molecule (Lei/PgpA), the CFTRs (human (Hum/CFTR), bovine (Bov/CFTR), mouse (Mus/CFTR), and dogfish (Squ/ CFTR)) (Cole et al. *Science* 1992 258:1650–1654). A similar result was obtained for the sulfonylurea receptor with the additional inclusion of the Xenopus CFTR indicating the receptor is a member of this cluster.

The identification of the nucleotide binding domains goes beyond simply having Walker "A" and "B" consensus sequences. The receptor is similar to the 230–240 amino acid nucleotide binding domain(s) described by (Hyde et al. *Nature* 1990 346:362–365) and database searches find similarities to the nucleotide binding fold of ATP-binding proteins. The more conserved of the two receptor nucleotide binding folds, based on similarity with other ATP-binding proteins and the comparison of the rat and hamster sequences, is at the C-terminal end.

RNA Analysis

Northern blot analysis of poly A+ mRNA isolated from RIN, HIT and αTC-6 cells, previously shown to have the high affinity receptor by drug binding and photolabeling studies (Aguilar-Bryan et al *J. Cell. Biochem. Suppl.* 1994 18A:133) each have an approximately 5000 nucleotide transcript, see FIG. 3. A preliminary tissue distribution study shows the same size transcript is present in mouse brain and heart.

Predicted Protein Structure

Sequence similarities indicate the sulfonylurea receptor has two potential ATP binding folds. The size and additional sequence similarities with P-glycoproteins and CFTRs suggest the receptor has a similar structure. Hydrophobicity (FIG. 4) and hydrophobicity versus hydrophobic moment (Eisenberg et al. *J. Mol. Biol.* 1984 179:125) plots were used to generate a model for the receptor (FIG. 5). Two constraints were imposed on the model structure: the glycosylation site is on the external face of the membrane and both nucleotide binding domains are on the internal face. The 'classical' ATP-binding cassette superfamily model proposes duplication of a unit consisting of six transmembrane spanning helices followed by a nucleotide binding domain. The sulfonylurea receptor differs from this model and has at least nine potential transmembrane helices before the first nucleotide binding domain but only four between the two nucleotide binding domains (FIG. 5). The multidrug resistance-associated protein (MRP) is predicted to have 8 transmembrane spanning helices (Cole et al. *Science* 1992 258:1650–1654).

Phosphorylation has been implicated in regulation of $K_{ATP}$ channel activity (Schwanstecher et al. *J. Pharmacol. Exper. Ther.* 1992 262:495–502) and has been proposed to change the affinity of the sulfonylurea receptor for various ligands. There are 21 potential phosphorylation sites in the receptor sequence; 3 protein Kinase A (pKA) sites and 18 protein kinase C (pKC) sites. The pKA site at 278 is predicted to be on the external face of the membrane, while those at positions 1363 and 1417 are in the second nucleotide binding fold. Four of the pKC sites (positions 151, 200, 304 and 1213) are predicted to be extracellular or in a membrane spanning helix. Seven of the remaining 14 are in the nucleotide binding folds (NBF); 4 in NBF-1, and 3 in NBF-2. One of the latter sites, Thr 1297 in the Walker A consensus site, is expected to alter nucleotide binding if it is accessible for phosphorylation.

Functional Properties, In Vitro Translations mRNA, transcribed by SP6 RNA polymerase from the rat cDNA subcloned into pGEM4, was translated in vitro. Approximately 0.5 μg of mRNA was heated to 70° C. for 10 minutes, immediately cooled on ice then added to rabbit reticulocyte lysate (Promega, Madison, Wis.) supplemented with ribonuclease inhibitor, an amino acid mixture, and [$^{35}$S]methionine. The reaction mixture was incubated at 30° C. for 60 minutes then aliquots were subject to electrophoresis on SDS polyacrylamide gels using standard protocols. The gels were dried and autoradiographed.

The resulting protein was approximately 137 kDa, indicating the receptor behaves anonymously on SDS polyacrylamide gels having a faster than expected mobility, see FIG. 6A. A similar anomalous behavior has been reported for CFTRs (Gregory et al. *Nature* 1990 347:382–386).

Anti-Nucleotide Fold Antibodies Immunoprecipitate the Photolabeled 140 kDa Receptor Antibodies were produced against two fusion proteins containing the two nucleotide binding folds. Fragments of the receptor cDNA were subcloned in frame into pMALc (New England BioLabs, Boston, Mass.) at the C-terminal end of the DNA encoding the maltose binding protein (MBP). A plasmid expressing the first nucleotide binding fold fused to MBP was constructed by restricting pMALc with StuI and SalI and restricting the sulfonylurea receptor cDNA with PvuII plus XhoI. A unique 500 base pair fragment was gel purified from the receptor cDNA digest and subcloned into pMALc. The construction was verified by sequencing. The receptor segment expressed is leu708 to leu874. Expression was obtained in *E. coli* following transformation and induction by isopropylthiogalactoside per the manufacturer's directions. The expressed proteins were found to be in inclusion bodies which were solubilized in SDS and separated on SDS polyacrylamide gels, see FIG. 6B. The fusion protein was electroeluted, concentrated, and used as an immunogen. The solubilized protein in 200 μg amounts, with complete, or incomplete Freund's adjuvant, was injected interdermally into rabbits using a standard 2–3 week regimen of bleeding and boosting.

Injection of Xenopus Oocytes with Receptor mRNA mRNA, approximately 50 ng, transcribed as described above, was injected into Xenopus oocytes. The injected oocytes were assayed for K+ channel activity after 1–5 days using both two-electrode and patch clamp methods. New K+ currents in the injected oocytes were not detected. Similarly, co-injection of mRNAs transcribed from cDNAs encoding two small inward rectifiers, ROMK1 (Ho et al. *Nature* 1993 362:31–38) or a brain homolog of IRK1 (Kelly et al. *Biophysical J.* 1994 66(2):A109) failed to confer sulfonylurea sensitivity on these K+ channels. The results suggest that the 140 kDa receptor does not have intrinsic K+ channel activity, or that Xenopus oocytes are not an adequate background for their expression.

Transfection Experiments

The sulfonylurea receptor cDNA has been ligated into eukaryotic expression vectors containing SV40 virus, adenovirus and cytomegalovirus (CMV) promoters. These plasmids have been transfected into COS cells which do not have the high affinity sulfonylurea receptor as determined by filtration binding and photolabeling studies. To date experiments with the SV40 plasmid have shown that the transfected cells produce an mRNA of the appropriate size as determined by Northern blots with receptor cDNA. Metabolic labeling experiments with the SV40 plasmid where transfected and non-transfected cells were labeled with [$^{35}$S] methionine indicate that the transfected, but not the non-transfected cells, synthesize an appropriate sized protein which can be immunoprecipitated with the antinucleotide binding fold antibodies. The level of receptor synthesized by COS cells using this promoter has been low using SEQ ID NOS: 27 and 28. Expression levels are high using SEQ ID NOS: 4, 5, 7, and 8 from rat and hamster.

Chromosomal localization of the Sulfonylurea Receptor Gene

Chromosomal localization of the Sulfonylurea Receptor (SUR) gene to normal male human banded chromosomes was determined by utilization of the fluorescence in situ hybridization (FISH) technique by staining with 4,6-diamidino-2-phenylindole (DAPI). A metaphase spread showed the two chromosome 11 homologues which map the SUR cDNA to 11p15.1. Overlapping human SUR cDNA plasmids "mid" and "3", totaling 3.8 kb, were labeled with biotin-14-dATP (GIBCO) and hybridized in situ to standard metaphase spreads from normal male peripheral blood lymphocytes, according to the methods of P. Lichter et al., *Science* 247, 64 (1990), the disclosure of which is hereby incorporated by reference in its entirety. The biotin-labeled DNA was detected using Fluorescein-Avidin DCS (Vector Laboratories, Burlingame, Calif.). Chromosomes were identified by simultaneous DAPI staining, which produces a Q-banding pattern. Fifteen metaphases were analyzed. Digital images were obtained with a cooled charge-coupled device camera mounted on a standard epifluorescent microscope (Axioplan; Zeiss, Thronwood, N.Y.). Images were acquired using the software ISee (Inovision Co.) running on a Sun workstation. Fluorescein isothiocyanate and DAPI fluorescence were recorded separately as gray scale images and then merged using the software package NIH 1.55 (J. W. Ijdo, E. A. Lindsay, R. A. Wells, A. Baldini, *Genomics* 14, 1019 (1992)). Eighty-five per cent of metaphases analyzed showed specific hybridization signal on both chromatids of the two chromosomes 11 at 11p15.1.

Partial cDNA clones, comprising 3.8 kb of coding sequence of the human homologue of SUR, were obtained from a human pancreatic cDNA library (provided by Graeme Bell, University of Chicago, and commercial libraries of Clontech, Palo Alto, Calif. and Invitrogen, San Diego, Calif.). The library was produced in lambda gt10 phage (Bell RIN library) and screened with a 2294 bp hamster cDNA probe encoded by SEQ ID NO: 30.

The protocol for making the library is provided by Sambrook et al., supra. Poly A+ mRNA was isolated using an oligo dT column. Poly A+ mRNA was incubated with oligo dT and random hexamers plus reverse transcriptase (such as MMLV RT from Promega, Stratagene or NEBL) and dNTPs to produce single strand cDNA. The single strand cDNA is treated with *E. coli* DNA polymerase, RNAseH and dNTPs, then ligated to linkers that have EcoRI sites to produce double stranded DNA. The final product is restricted with EcoRI and ligated, using T4 DNA ligase, into lambda phage DNA that has been similarly restricted and dephosphorylated with alkaline phosphatase to prevent self ligation. The ligated product is packaged into phage using commercially available packaging extracts.

Screening involved plating and hybridizing at 55° C. or 65° C. in 5× or 6× SSC (according to the methods of Sambrook, et al.). 55° C. was used for cross species screens and 65° C. was employed for the same species. Two washes were carried out at room temperature using 2× SSC, then one at the hybridization temperature of 65° C. using 0.1× SSC.

Hybridizations and washes were done at reduced stringency (55° C.) using methods according to F. M. Ausubel et al., *Current Protocols in Molecular Biology* (Greene Publishing Associates, Inc, New York, N.Y., 1989), Chap. 6, the disclosures of which are hereby incorporated by reference in their entirety. Subsequent screening was done at higher stringency (65° C.), using a human cDNA of SEQ ID NO: 31 obtained from the first screen as a probe.

Characterization of these cDNA clones by sequence analysis revealed an overall homology of 95% with the rat SUR gene. A specific hybridization signal was detected at the band 11p15.1 in 85% of metaphases on both chromatids of the two chromosomes 11.

Detection of Sulfonylurea Receptor Mutations in PHHI Affected Individuals

Mutational analysis was performed on samples from 16 affected progeny of nine consanguineous matings. In each case, diagnosis of PHHI was based on criteria established by A. Aynsley-Green et al., supra., the disclosure of which is hereby incorporated by reference in its entirety. The parents in six families were first cousins, in two families second cousins, and in one family more distantly related. Eight families were of Saudi Arabian origin, recruited from the patient population of the Arabian American Oil Company Hospital Medical Services Organization, after institutional approval was received, and one was of Germanic origin. Family labels follow the form of Thomas et al., supra.

Studies indicated that no major insertions or deletions of the SUR locus had occurred in three of the families. The first region evaluated, by direct sequence analysis, was the second nucleotide binding fold (NBF-2) of the human SUR homologue (FIG. 7). This is the most highly conserved region of the SUR gene, and in other superfamily members it, as well as NBF-1, has functional importance for control of channel activity through interaction with cytosolic nucleotides. S. C. Hyde, *Nature* 346, 362 (1990) and M. J. Weish, A. E. Smith, *Cell* 73, 1251 (1993).

To obtain this genomic structure, a normal human lymphocyte genomic bacteriophage library (provided by Mary Beth Humphrey, Baylor College of Medicine) was screened, using standard methods according to F. M. Ausubel et al., supra., with a human partial SUR cDNA probe of SEQ ID NO: 31 (cDNA probe, "3prime").

The human genomic library was made in lambda FIX using materials supplied by Stratagene, Inc. Briefly, genomic DNA was partially digested with Sau3A, the fragments were precipitated with ethanol, resuspended with precut lambda FIX DNA which has compatible ends, ligated with T4 DNA ligase and packaged and screened.

Hybridizations and washes were done at reduced stringency (55° C.) using methods according to F. M. Ausubel et al., *Current Protocols in Molecular Biology* (Greene Publishing Associates, Inc, New York, N.Y., 1989), Chap. 6, the disclosures of which are hereby incorporated by reference in their entirety. The library was screened with a 1.2 kb hamster cDNA probe of SEQ ID NO: 32, which spans the SUR NBF2 sequence. Subsequent screening was done at higher stringency (65° C.), using a human cDNA.

Screening involved plating and hybridizing at 55° C. or 65° C. in 5× or 6× SSC (according to the methods of Sambrook, et al.) . 55° C. was used for cross species screens and 65° C. was employed for the same species. Two washes were carried out at room temperature using 2× SSC, then one at the hybridization temperature of 65° C. using 0.1× SSC.

Inserts in the bacteriophage clone λG4 were subcloned into pBluescript 11 (Stratagene, La Jolla, Calif.). Plasmids were purified using standard cesium chloride purified methods, restricted using the appropriate desired enzyme(s). The fragments were purified by electrophoresis on low melt agarose and cut out of the gel. A 1-to-5 microliter aliquot of the desired fragment and 1 microgram of the appropriately restricted plasmid carrying a selectable ampicillin resistance marker (such as pBluescript from Stratagene, Inc.) were melted at 65° C., mixed and diluted to 20 microliters with a buffer containing T4 DNA ligase and ATP, then incubated for 4–18 hours before transforming into *E. coli* and selecting on ampicillin plates.

Exon-intron boundaries were defined by comparing the nucleotide sequences of the human SUR gene and cDNA, which were obtained using the dideoxy chain termination method (Sequenase; U.S. Biochemicals, Cleveland, Ohio).

Because of the consanguineous matings and autosomal recessive inheritance pattern of this disorder, affected individuals are expected to be homozygous by descent at the disease gene locus. E. S. Lander and D. Botstein, *Science* 236, 1567 (1987), the disclosure of which is hereby incorporated by reference in its entirety. Direct sequencing of a pancreatic cDNA product, isolated from an affected child of Family 6, revealed a 109 bp deletion within the NBF-2 region which corresponded to skipping of an exon resulting in a cDNA product of about 2190 bp in length using primers of SEQ ID NOS: 16 and 17 as compared to mRNA of about 2080 bp in length. The effects of this skipping event are severe and include production of a frameshift, premature truncation of the protein due to inclusion of a stop 24 codons later, and disruption of the NBF-2 (FIG. 8A and 8B). The splice sites of the skipped exon were evaluated at the genomic DNA level and a homozygous G to A point mutation, located within the 5' splice site at the last base of the skipped exon, was found (FIG. 8C). A recognition site for the restriction endonuclease MspI is destroyed by this base change, providing a means to confirm and test for the presence of the mutation. mRNA was directly isolated using Oligotex (Qiagen Inc., Studio City, Calif.) from a fresh-frozen pancreatic tissue sample and reverse transcribed (RT), using random primers (Invitrogen, San Diego, Calif.), with Superscript 11 (GIBCO-BRL) into cDNA. For cloning of the NBF-2 region, an initial PCR amplification with SEQ ID NOS: 19 (primer 22 (located 5' of 17)) and 15 (primer 29) was followed by a second amplification of a portion of the reaction with SEQ ID NOS: 13 (primer 13) and 15 (primer 29) using conditions described by P. M. Thomas, G. J. Cote, D. M. Hallman, P. M. Mathew, *Am. J. Hum. Genet.*, in press, supra.

PCR products were amplified using hybridization at 60° C. for 1 minute, elongated at 72° C. for 1 minute and denatured at 93° C. for 1 minute for thirty cycles. Hybridization may be carried out at temperatures of between about 55° C. to about 65° C. The amplified product was cloned into pCR 11™ vector (Invitrogen, San Diego, Calif.) and sequenced, as above. pCR 11™ vector is set forth in FIG. 13. For detection of the mutation in genomic fragments, 100 ng of genomic DNA was amplified using SEQ ID NOS: 14 and 16, primers 28 and 29B, as above except in the presence of PCR buffer N (Invitrogen, San Diego, Calif.), and either directly PCR sequenced according to the methods of S. Khorana, R. F. Gagel, G. J. Cote, *Nucleic Acids Res.* 22, 3425 (1994), the disclosure of which is hereby incorporated herein by reference in its entirety, or cut with 5 U of Mspl (GIBCO-BRL) at 37° C. for 2 hours and run on a 10% polyacrylamide gel. Visualization of products was by silver staining. Both affected children of Family 6 were homozygous, while the parents and two unaffected siblings were found to be heterozygous, for the mutation (FIG. 8D). Preliminary semiquantitative analysis revealed markedly decreased expression of the mutant SUR message upon comparison of patient and age-matched normal control pancreatic samples, suggesting instability of the mutant message.

Thirteen additional affected children, from six families of Saudi Arabian origin and one family of German origin, were found to be homozygous for this mutation, as demonstrated by loss of the Mspl restriction enzyme recognition site. In all families, homozygous loss of the Mspl site cosegregated with disease phenotype, and in Families 1–3 and 5 genotype analysis for this mutation agreed with previously reported haplotype data, P. M. Thomas, G. J. Cote, D. M. Hallman, P. M. Mathew, *Am. J. Hum. Genet.*, in press, supra. Direct sequencing of PCR-amplified genomic DNA from a representative affected member of each family determined that all exhibited the homozygous G to A mutation.

Family 4 demonstrated a unique mutation in the 3' splice site sequence preceding the start of the NBF-2 (FIG. 9A). This G to A mutation destroys an Ncil restriction endonuclease site and homozygous loss of this site cosegregated with disease phenotype within the family. Again, genotype analysis of the members of this family supported previously reported haplotype data, P. M. Thomas, G. J. Cote, D. M. Hallman, P. M. Mathew, *Am. J. Hum. Genet.*, in press, supra.; both parents are heterozygotes for the mutation and the unaffected sibling is homozygous for the wild type allele (FIG. 9B). Since a pancreatic tissue sample from an affected individual in Family 4 was unavailable and we were unable to recover the SUR message from transformed lymphocytes, a chimeric construct was created to examine the effects of this mutation on the RNA splicing pathways according to the methods of R. Takahashi, et al., *Nature Genet.* 7, 79 (1994); I. Satokata, et al., *Proc, Natl. Acad. Sci.* 87 9908 (1990); H. Lou, G. J. Cote, R. F. Gagel, *Mol. Endo.* 8, 1618 (1994), the disclosure of each hereby incorporated by reference in its entirety.

Genomic DNA from affected and normal individuals was PCR-amplified using the SEQ ID NOS: 12 and 18 and cloned into pRSVhMT2A. Constructs were transfected into the human glioblastoma cell line SNB 19 using LIPO-FECTAMINE® transfection regent (Gibco-BRL, Gaithersburg, Md.). RT-PCR analysis was performed, with SEQ ID NOS:12 (primer 16) and 19 (primer DS8), as described by H. Lou, G. J. Cote, R. F. Gagel, *Mol. Endo.* 8, 1618 (1994), the disclosure of which is incorporated herein by reference in its entirety. The plasmids and their cDNA products were sequenced with SEQ ID NO: 17 (primer 34al). Genomic DNA fragments were PCR-amplified with SEQ ID NOS: 17 and 12 (primers 34al and 16) and digested with Ncil, as in FIG. 8. With the construct containing the mutation, no wild type splicing pattern occurred. Instead, use of three cryptic 3' splice sites was demonstrated resulting in a 7 bp addition, a 20 bp deletion, and a 30 bp deletion in the exon (FIG. 9D). A similar intronic 3' splice acceptor mutation, described in the disorder 21-hydroxylase deficiency, also resulted in lack of the wild type splicing pattern, produced several cryptic splice products, and abolished normal protein activity. Y. Higashi, et al., *Proc. Natl. Acad. Sci., USA* 85, 7486 (1988), the disclosure of which is incorporated herein by reference in its entirety.

All PCR products prepared from genomic DNA of 100 normal, unrelated individuals showed normal Mspi and Ncil restriction patterns, indicating that neither mutation is a common polymorphism. The data presented provides evidence that mutations in the SUR gene cause familial persistent hyperinsulinemic hypoglycemia of infancy.

Various modifications of the invention in addition to those shown and described herein will be apparent to those skilled in the art from the foregoing description. Such modifications are also intended to fall within the scope of the appended claims.

What is claimed is:

1. A purified nucleic acid sequence encoding a sulfonylurea receptor wherein said nucleic acid sequence is selected from the group consisting of SEQ ID NO: 1, SEQ ID NO: 4, and SEQ ID NO: 7.

2. A purified amino acid sequence selected from the group consisting of SEQ ID NO: 3, SEQ ID NO: 6 and SEQ ID NO: 9.

3. An expression vector comprising a nucleic acid sequence selected from the group consisting of SEQ ID NO: 1, SEQ ID NO: 4, and SEQ ID NO: 7.

4. A host cell expressing the nucleic acid sequence selected from the group consisting of SEQ ID NO: 1, SEQ ID NO: 4, and SEQ ID NO: 7.

5. A cell culture comprising cells that express a nucleic acid sequence encoding a sulfonylurea receptor protein comprising the amino acid sequence selected from the group consisting of SEQ ID NO: 3, SEQ ID NO: 6, and SEQ ID NO: 9.

6. A purified nucleic acid sequence encoding a sulfonylurea receptor, wherein said nucleic acid sequence comprises SEQ ID NO: 1.

7. An expression vector comprising a nucleic acid sequence of SEQ ID NO: 1.

8. An insolated host cell expressing the nucleic acid sequence of SEQ ID NO: 1.

9. A cell culture comprising cells that express a nucleic acid sequence encoding a sulfonylurea receptor comprising the amino acid sequence of SEQ ID NO: 28.

* * * * *

UNITED STATES PATENT AND TRADEMARK OFFICE
CERTIFICATE OF CORRECTION

PATENT NO.    : 6,054,313
DATED         : April 25, 2000
INVENTOR(S)   : Bryan et al.

It is certified that error appears in the above-identified patent and that said Letters Patent is hereby corrected as shown below:

Title page,
Item [56], References Cited, OTHER PUBLICATIONS,
Nelson et al., please delete "Sensive" and insert therefor -- sensitive --;
Nelson et al., please delete "sufonylurea" and insert therefor -- sulfonylurea --;

Column 2,
Line 18, please delete "G11" and insert therefor -- D11 --;

Column 6,
Line 10, please delete "and";

Column 10,
Line 39, please delete "sulonylurea" and insert therefor -- sulfonylurea --;

Column 18,
Line 32, please delete "βcell" and insert therefor -- β-cell --;
Line 67, please delete "of";

Column 19,
Line 51, please delete "Tween-20®" and isnert therefor -- TWEEN-20® --;

Column 27,
Line 10, delete "(primer 13)" and insert therefor -- (primer 17) --;

Column 129,
Line 25, please delete "A host" and insert therefor -- An isolated host --.

Signed and Sealed this

Eighteenth Day of June, 2002

Attest:

JAMES E. ROGAN
Attesting Officer           Director of the United States Patent and Trademark Office